United States Patent [19]
Knowles et al.

[11] Patent Number: 5,972,680
[45] Date of Patent: Oct. 26, 1999

[54] GLUCOSE TRANSPORTER VESICLE AMINOPEPTIDASE

[75] Inventors: William J. Knowles, Madison; Donna Guralski, Oxford; John T. Letsinger, West Haven; Wallace Haigh, Madison; John T. Hart, Wallingford; Kevin B. Clairmont, Cheshire, all of Conn.

[73] Assignee: Bayer Corporation, Pittsburgh, Pa.

[21] Appl. No.: 08/530,792

[22] Filed: Sep. 19, 1995

Related U.S. Application Data

[63] Continuation-in-part of application No. 08/309,232, Sep. 20, 1994, abandoned.

[51] Int. Cl.$^6$ ............................... C12N 9/50; C07H 21/04
[52] U.S. Cl. ..................... 435/219; 435/212; 435/226; 435/325; 435/252.3; 435/252.33; 435/320.1; 536/23.1; 536/23.2; 536/23.5
[58] Field of Search ..................... 435/219, 212, 435/226, 325, 320.1, 252.3, 252.33; 536/23.1, 23.2, 23.5

[56] References Cited

FOREIGN PATENT DOCUMENTS 9217575  10/1992  WIPO .

OTHER PUBLICATIONS

Kandror et al. "Identification and isolation of glycprotein that translocate to the cell surface from GLUT4–enriched vesicle in an insulin–dependent fashion" J. Biol. Chem. 269, 138–142, Jan. 1994.

Mastick et al. "Characterization of a major protein in GLUT4 vesicles" J. Biol. Chem. 269, 6089–6092, Feb. 1994.

Kandror et al. "gp160, a tissue–specific marker for insulin–activated gklucose transport" Proc. Natl. Acad. Sci. USA 91, 8017–8021, Aug. 1994.

Rogi et al. "Human placental leucine aminopeptidase/oxytocinase" J. Biol. Chem. 271, 56–61, Jan. 1996.

Keller et al. "Cloning and characterization of a novel insulin–regulated membrane aminopeptidase from Glut vesicles" J. Biol. Chem. 270, 23612–23618, Oct. 1995.

James, D., et al, *Letters to Nature,* 338, 83–87, (1989).

Verhey, K. et al, *J. Biol., Chem.,* 269, 2353–2356 (1994).

Tsujimoto, M. et al, *Archives of Biochem and BioPhys.* 292, 388–392 (1992).

Kandror, et al., "The Major Protein of GLUT4–containing Vesicles, gp160, Has Aminopeptidase Activity", J. Biol. Chem., 269:49, pp. 30777–30780 (Dec. 9, 1994).

*Primary Examiner*—Ponnathapura Achutamurthy
*Assistant Examiner*—Nashaat T. Nashed
*Attorney, Agent, or Firm*—Alice A. Brewer

[57] ABSTRACT

An aminopeptidase which is a component of GLUT4-containing vesicles in the natural state, and which cleaves insulin. The claimed protein has an apparent molecular weight of approximately 110 kD in its deglycosylated form and a predicted molecular weight of 117,239 Daltons. It includes the amino acid sequences Phe-Ala-Ala-Thr-Gln-Phe-Glu-Pro-Leu-Ala-Ala (SEQ ID NO: 1) and Ile-Leu-Gln-Asn-Gln-Ile-Gln-Gln-Gln-Thr-Arg-Thr-Asp-Glu-Gly-Xaa-Pro-Xaa-Met (SEQ ID NO: 2, and reacts with antibodies produced against the peptide identified as (SEQ ID NO: 1). It is encoded by the cDNA of FIG. 20 (SEQ. ID NOs. 15 and 16) and is essentially the protein sequence therein described. Modulators of the activity of the aminopeptidase and a method for treating syndromes of insulin resistance, including diabetes, by administration of such a modulator are also claimed.

6 Claims, 19 Drawing Sheets

TIME = 0

TIME = 3.5hrs

TIME = 22hrs

```
  1 CTCTCGGAGT AGAAAGCTTG GGGCGCTGGG CTGGTGAGGA CCCGCAGCGG GCGAAG ATG
                                                                 1►Met
 60 GAG ACC TTT ACC AAT GAT CGA CTT CAG CTT CCA AGG AAT ATG ATT GAA AAC
  2►Glu Thr Phe Thr Asn Asp Arg Leu Gln Leu Pro Arg Asn Met Ile Glu Asn
111 AGC ATG TTT GAA GAA GAG GAA CCA GAT GTA GAT GCC AAA GAA CCT TGT
 19►Ser Met Phe Glu Glu Glu Pro Asp Val Asp Ala Lys Glu Pro Cys
162 TTA CAT CCT CTG GAA CCT GAT GAA GTT GAA TAT GAG CCC CGA GGT TCG AGG
 36►Leu His Pro Leu Glu Pro Asp Glu Val Glu Tyr Glu Pro Arg Gly Ser Arg
213 CTT CTG AGA GGT CTT GGT CAT GAG GAT GAG GAA GAG GAT
 53►Leu Leu Arg Gly Leu Gly His Glu Asp Glu Glu Glu Asp
264 TAT GAG TCA TCT GCC AAG CTG CTG ATG TCC TTC ATG AAC AGA AGC TGT
 70►Tyr Glu Ser Ser Ala Lys Leu Leu Met Ser Phe Met Asn Arg Ser Cys
315 GGC CTT CGG AAC AGT GCA ACA GGC TAC CAG CAG AGT CCA GAT GGG ACT TGT
 87►Gly Leu Arg Asn Ser Ala Thr Gly Tyr Gln Gln Ser Pro Asp Gly Thr Cys
366 TCA GTA CCC TCT GCC AGG ACC TTA GTA ATC TGT GTT TTT GTC ATT GTG GTT
104►Ser Val Pro Ser Ala Arg Thr Leu Val Ile Cys Val Phe Val Ile Val Val
417 GCT GTC TCT GTA ATC ATG GTG TAT CTA CCT AGA TGT CCT ACC TTT ACC
121►Ala Val Ser Val Ile Met Val Tyr Leu Pro Arg Cys Pro Thr Phe Thr
468 AAA GAA GGC TGC CAC AAA AAC CAG GAA TCA GCA GAA CTC ATT CAG CCG ATT
138►Lys Glu Gly Cys His Lys Asn Gln Glu Ser Ala Glu Leu Ile Gln Pro Ile
519 GCT ACA AAC GGG AAA GTG TTT CCA GCA CAA ATT AGG CTT CCC ACT GCC
155►Ala Thr Asn Gly Lys Val Phe Pro Ala Gln Ile Arg Leu Pro Thr Ala
570 ATT ATT CCT CAA CGC TAT GAA CGC TAT AGC CAT CCA AAC CTA ACC ATG
172►Ile Ile Pro Gln Arg Tyr Glu Arg Tyr Ser His Pro Asn Leu Thr Ser Met
621 ACA TTC AGG GGT TCT GTG ACA TCA CTT CAG GCT CTT CAA GAT ACA CGG
189►Thr Phe Arg Gly Ser Val Thr Ser Leu Gln Ala Leu Gln Asp Thr Arg
```

FIG. 20A

| | | | | | | | | | |
|---|---|---|---|---|---|---|---|---|---|
| 672 | GAC | ATC | ATT | CTC | CAT | AGC | ACA | GGA | CAT | AAT | ATT | TCA | AGT | GTG | ACA | TTT | ATG |
| 206▶ | Asp | Ile | Ile | Leu | His | Ser | Thr | Gly | His | Asn | Ile | Ser | Ser | Val | Thr | Phe | Met |
| 723 | TCG | GCG | GTT | TCC | AGT | TCC | CAA | GTT | GAA | ATT | CTG | GAA | ATT | CTA | GAA | TAT | CCA | TAT |
| 223▶ | Ser | Ala | Val | Ser | Ser | Ser | Gln | Val | Glu | Ile | Leu | Glu | Ile | Leu | Glu | Tyr | Pro | Tyr |
| 774 | CAT | GAA | CAA | ATC | GCC | GTT | GCC | CCT | GAA | AGC | CTT | CTA | ACA | GGA | CAC | AAT |
| 240▶ | His | Glu | Gln | Ile | Ala | Val | Ala | Pro | Glu | Ser | Leu | Leu | Thr | Gly | His | Asn |
| 825 | TAT | ACC | TTG | AAG | ATA | GAA | TAT | TCA | GCA | AAT | ATA | TCT | AAC | TCT | TAC | TAT | GGG |
| 257▶ | Tyr | Thr | Leu | Lys | Ile | Glu | Tyr | Ser | Ala | Asn | Ile | Ser | Asn | Ser | Tyr | Tyr | Gly |
| 876 | TTT | TAT | GGC | ATC | ACC | TAC | ACA | GAT | AAA | AGT | AAT | GAG | AAA | AAG | AAC | TTT | GCA |
| 274▶ | Phe | Tyr | Gly | Ile | Thr | Tyr | Thr | Asp | Lys | Ser | Asn | Glu | Lys | Lys | Asn | Phe | Ala |
| 927 | GCA | ACT | CAG | TTT | GAA | CCT | TTG | GCA | GCA | AGA | TCT | GCT | TTT | CCT | TGT | TTT | GAT |
| 291▶ | Ala | Thr | Gln | Phe | Glu | Pro | Leu | Ala | Ala | Arg | Ser | Ala | Phe | Pro | Cys | Phe | Asp |
| 978 | GAA | CCA | GCA | TTT | AAG | GCC | ACA | ACA | ATC | ATC | ATC | AAG | ACA | AGG | GAT | GAG | CAC |
| 308▶ | Glu | Pro | Ala | Phe | Lys | Ala | Thr | Thr | Ile | Ile | Ile | Lys | Thr | Arg | Asp | Glu | His |
| 1029 | CAT | ACT | GCA | TTA | TCA | AAT | ATG | CCT | AAG | AAG | TCA | GTC | CCT | ACA | GAA | GAA |
| 325▶ | His | Thr | Ala | Leu | Ser | Asn | Met | Pro | Lys | Lys | Ser | Val | Pro | Thr | Glu | Glu |
| 1080 | GGA | CTT | ATT | CAA | GAT | GAG | TTT | TCT | GAA | AGT | GTG | AAA | ATG | AGC | ACA | TAC | CTG |
| 342▶ | Gly | Leu | Ile | Gln | Asp | Glu | Phe | Ser | Glu | Ser | Val | Lys | Met | Ser | Thr | Tyr | Leu |
| 1131 | GTT | GCT | ATT | TTC | ATT | GTA | GGG | GAG | ATG | CAG | AGT | CAG | GAT | GTA | AAC | GGG |
| 359▶ | Val | Ala | Ile | Phe | Ile | Val | Gly | Glu | Met | Arg | Asn | Leu | Ser | Gln | Asp | Val | Asn | Gly |
| 1182 | ACT | CTG | GTT | TCT | GTA | TAT | GCT | GTA | CCA | GAA | ATT | GAT | CAA | GTT | TAC | CAT |
| 376▶ | Thr | Leu | Val | Ser | Val | Tyr | Ala | Val | Pro | Glu | Ile | Asp | Gln | Val | Tyr | His |
| 1233 | GCC | TTG | GAC | ACT | GTA | AAG | CTC | CTT | GAG | TTT | TAT | CAA | AAT | TAC | TTT | GAA |
| 393▶ | Ala | Leu | Asp | Thr | Val | Lys | Leu | Leu | Glu | Phe | Tyr | Gln | Asn | Tyr | Phe | Glu |
| 1284 | ATT | CAA | TAC | CCA | CTA | AAG | AAA | TTG | GAT | CTG | GCC | ATT | CCT | GAC | TTT | GAA |
| 410▶ | Ile | Gln | Tyr | Pro | Leu | Lys | Lys | Leu | Asp | Leu | Ala | Ile | Pro | Asp | Phe | Glu |

FIG. 20B

```
1335 GCT GGA GCA ATG GAA AAT TGG GGC CTG CTT ACG TTC CGA GAA GAG ACT CTT
 427▶Ala Gly Ala Met Glu Asn Trp Gly Leu Leu Thr Phe Arg Glu Glu Thr Leu
1386 CTG TAT GAC AAT GCC ACT TCT TCA CAT GTA GCA GAT AGA AAA CTG GTC ACT AAA
 444▶Leu Tyr Asp Asn Ala Thr Ser Ser His Val Ala Asp Arg Lys Leu Val Thr Lys
1437 ATC ATC GCT CAC GAG CTG CTG CTG GCA TGG TTT GGT AAT CTG GTT ACA ATG
 461▶Ile Ile Ala His Glu Leu Leu Ala Trp Phe Gly Asn Leu Val Thr Met
1488 CAG TGG AAT GAC CTG TGG CTA AAC GAA GGG TTT GCC ACT TTC ATG GAG
 478▶Gln Trp Asn Asp Leu Trp Leu Asn Glu Gly Phe Ala Thr Phe Met Glu
1539 TAT TTC TCT GTG GAA ATA TTC AAA GAG CTC AAC TAT GAA GAC TTC
 495▶Tyr Phe Ser Val Glu Ile Phe Lys Glu Leu Asn Tyr Glu Asp Phe
1590 TTA GAT GCT CGA TTT AAA ACC ATG AGG AAG GAT TCC AAT TCG TCT CAT
 512▶Leu Asp Ala Arg Phe Lys Thr Met Arg Lys Asp Ser Leu Asn Ser Ser His
1641 CCA ATA TCA TCT GTT CAG TCA GAA CAA ATA GAA GAA ATG TTT GAT
 529▶Pro Ile Ser Ser Val Gln Ser Glu Gln Ile Glu Glu Met Phe Asp
1692 TCT CTT TCG TAT TTT AAG CAG GGA GCG TCT CTC TTG ATG TTG AAA AGT
 546▶Ser Leu Ser Tyr Phe Lys Gln Gly Ala Ser Leu Leu Met Leu Lys Ser
1743 TAC CTT AGT GAA GAC CAG TTT CAG CAT GCC ATT CTT TAC CTG CAC AAT
 563▶Tyr Leu Ser Glu Asp Gln Phe Gln His Ala Ile Leu Tyr Leu His Asn
1794 CAC AGC TAT GCA GCA ATT CAA GAT AGC GAT CTC TGG GAC AGC TTC AAT GAG
 580▶His Ser Tyr Ala Ala Ile Gln Asp Ser Asp Leu Trp Asp Ser Phe Asn Glu
1845 GTC ACA GGC AAA ACT GAT GTA AAG ATG AAA ACC TGG ACC CTA
 597▶Val Thr Gly Lys Thr Asp Val Lys Met Lys Thr Trp Thr Leu
1896 CAG AAA GGA TTC CCA ACC GTC CAG AGA GGG ACT GAG CTT CTT
 614▶Gln Lys Gly Phe Pro Thr Val Gln Arg Gly Thr Glu Leu Leu
1947 CTA CAA CAA GAA AGA TTT TTT CCA CAA ATG CAA GAA ATT CAG GAT TCA
 631▶Leu Gln Gln Glu Arg Phe Phe Pro Gln Met Gln Glu Ile Gln Asp Ser
```

```
2661  GCA AGA ACC GAG AAA GGC TGG TTG TTC CTC TTT AGC ATG TAC TCC ATG
 869▸ Ala Arg Thr Glu Lys Gly Trp Leu Phe Leu Phe Ser Met Tyr Ser Met
2712  GGC TCT GAA GCA GAG AAG GAT AAA ATA ATT CTT GAA GCC CTG TCA GCG
 886▸ Gly Ser Glu Ala Glu Lys Asp Lys Ile Ile Leu Glu Ala Leu Ser Ala
2763  GAT GCA CAT AAA CTT TAC TGG TTA ATG AAA AGT AGC CTT GAT GAT ATC
 903▸ Asp Ala His Lys Leu Tyr Trp Leu Met Lys Ser Ser Leu Asp Asp Ile
2814  ATT CGG ACA CAG AAG TTG TCA CTT ATC CTT ATT AGA GTG GGC AGA CAG TTT
 920▸ Ile Arg Thr Gln Lys Leu Ser Leu Ile Leu Ile Arg Val Gly Arg Gln Phe
2865  CCT GGA CAT TTG CTG GCA TGG GAT TTT GTT AAG AAC TGG AAT AAG CTT
 937▸ Pro Gly His Leu Leu Ala Trp Asp Phe Val Lys Asn Trp Asn Lys Leu
2916  GTA CAT AAG TTC CAT CTG GGC TCC TAT ACC ATT CAA AGC ATT GTT GCT GGA
 954▸ Val His Lys Phe His Leu Gly Ser Tyr Thr Ile Gln Ser Ile Val Ala Gly
2967  TCT ACT CAC TTA TTT TCA ACG AAG ACA CAT TTA TCT GAG GTC CAG GAA TTC
 971▸ Ser Thr His Leu Phe Ser Thr Lys Thr His Leu Ser Glu Val Gln Glu Phe
3018  TTC GAA AAT CAG TCA GAG GCA ACC TTG CAG CTT CGG TGT GTT CAG GAG GCC
 988▸ Phe Glu Asn Gln Ser Glu Ala Thr Leu Gln Leu Arg Cys Val Gln Glu Ala
3069  TTC GAA GTG ATT GAG GAG CTG AAT ATC CAG TGG ATG AGG AAT CTG AAA ACT
1005▸ Phe Glu Val Ile Glu Glu Leu Asn Ile Gln Trp Met Ala Arg Asn Leu Lys Thr
3120  CTG ACA CTG TGG CTG TAG CCCTCACAGC TGATCTTCCG GTGCCCATGG CTCTGCTGCT
1022▸ Leu Thr Leu Trp Leu •••
3178  TTTGCAAAGG TTGAGTGAAG GCCGGCCTGC TACTGAGTTG TTTGCACTGT TAGGATCTAG
3238  TTAGCTCAGG GCCCAATTGT ATTTTCATA TCTTTTCTGA AATGTCCTTA GGCGGGTAGTT
3298  ATTTATTACA AAATTATATT CACCTGTACG TCAACCATCT ACAATAACAG TGAAGACCTG
3358  CCCGCGCGGC CGCTCGAGCC CTATAGTGAG T
```

```
His    Acidic/Proline                              Tyr Glu              Ser          Basic              Leu Leu
  ⎧  ⎧ Leu Pro Asp Glu Val Glu ⎫  Tyr Glu    ⎧ Pro Arg Gly Ser ⎫       ⎧ Arg ⎫                ⎧ Leu Leu ⎫  (SEQ ID NO: 17)
His⎨  ⎨ Met Asp Glu Asp Glu Asp ⎬  Tyr Glu    ⎨     Ser Ser Ser ⎬  Ala  ⎨ Lys ⎬                ⎨ Leu Leu ⎬  (SEQ ID NO: 18)
  ⎩  ⎩ Asn Glu Asp Pro Gly Leu ⎭  Tyr Glu    ⎩     Leu Glu Thr Ser ⎭ Pro ⎩ Lys Val Glu Gln Glu ⎭ Leu Leu ⎭  (SEQ ID NO: 19*)

X¹aa Xaa  (X¹aa)₃  (Xaa)₂₋₃  Tyr Glu  (Xaa)₁₋₃  Ser  (Xaa)₀₋₁  X²aa  (Xaa)₀₋₄  Leu Leu  (SEQ ID NO: 20)

reverse consensus sequence:
Leu Leu (Xaa)₀₋₄ X²aa (Xaa)₀₋₁ Ser (Xaa)₁₋₃ Glu Tyr (Xaa)₂₋₃ (X¹aa)₃ Xaa X¹aa (SEQ ID NO: 21*)
```

FIG. 21

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 11 amino acids
        (B) TYPE: amino acid
        (D) TOPOLOGY: linear

```
        (ii) MOLECULE TYPE: protein fragment
             (A) DESCRIPTION: tryptic digest polypeptide from full
                 length protein (v) FRAGMENT TYPE: internal fragment (vi) ORIGINAL SOURCE: affinity purified protein from-
             (A) ORGANISM: Rattus norvegicus
             (B) STRAIN:Sprague-Dawley
             (F) TISSUE TYPE: adipose (ix) FEATURE:
             (A) NAME/KEY: GTVap fragment p94
             (C) IDENTIFICATION METHOD: protein sequencing (xi) SEQUENCE DESCRIPTION: SEQ ID NO: 1:

Phe Ala Ala Thr Gln Phe Glu Pro Leu Ala Ala
                 5                  10

(2) INFORMATION FOR SEQ ID NO: 2:

(i) SEQUENCE CHARACTERISTICS:
             (A) LENGTH: 19 amino acids
             (B) TYPE: amino acid
             (D) TOPOLOGY: linear (ii) MOLECULE TYPE: protein fragment
             (A) DESCRIPTION: tryptic digest polypeptide from full
                 length protein (v) FRAGMENT TYPE: internal fragment (vi) ORIGINAL SOURCE: affinity purified protein from-
             (A) ORGANISM: Rattus norvegicus
             (B) STRAIN: Sprague-Dawley
             (F) TISSUE TYPE: adipose (ix) FEATURE:
             (A) NAME/KEY: GTVap fragment p85
             (C) IDENTIFICATION METHOD: protein sequencing
             (D) OTHER INFORMATION:  GeneSeq patent database partial match
                 (accession # GSP:R28142; EP 0 535 241 A1) identified as
                 leucine aminopeptidase from placental origin (xi) SEQUENCE DESCRIPTION: SEQ ID NO: 2:

Ile Leu Gln Asn Gln Ile Gln Gln Gln Thr Arg Thr Asp Glu Gly Xaa
                 5                  10                  15

Pro Xaa Met (2) INFORMATION FOR SEQ ID NO: 3:

(i) SEQUENCE CHARACTERISTICS:
             (A) LENGTH: 33 nucleotides
             (B) TYPE: nucleic acid
             (C) STRANDEDNESS: single
             (D) TOPOLOGY: linear (ii) MOLECULE TYPE: Other nucleic Acid: synthetic oligonucleotide
             probe based on peptide sequence (iii) HYPOTHETICAL: yes (iv) ANTI-SENSE: no (xi) SEQUENCE DESCRIPTION: SEQ ID NO: 3:

TTYGCNGCNA CNCARTTYGA RCCNYTNGCN GCN                                33

(2) INFORMATION FOR SEQ ID NO: 4:

(i) SEQUENCE CHARACTERISTICS:
             (A) LENGTH: 33 nucleotides
             (B) TYPE: nucleic acid
```

(C) STRANDEDNESS: single
(D) TOPOLOGY: linear (ii) MOLECULE TYPE: Other nucleic Acid: synthetic
    oligonucleotide probe based on peptide sequence (iii) HYPOTHETICAL: yes (iv) ANTI-SENSE: yes (xi) SEQUENCE DESCRIPTION: SEQ ID NO: 4:

NGCNGCNARN GGYTCRAAYT GNGTNGCNGC RAA                    33

(2) INFORMATION FOR SEQ ID NO: 5:

(i) SEQUENCE CHARACTERISTICS:
        (A) LENGTH: 15 amino acids
        (B) TYPE: amino acid
        (D) TOPOLOGY: linear (ii) MOLECULE TYPE: protein fragment
        (A) DESCRIPTION: tryptic digest polypeptide from full
            length protein (v) FRAGMENT TYPE: internal fragment (vi) ORIGINAL SOURCE:
        (A) ORGANISM: Rattus norvegicus
        (B) STRAIN: Sprague-Dawley
        (F) TISSUE TYPE: adipose (ix) FEATURE:
        (A) NAME/KEY: GTVap fragment p85
        (C) IDENTIFICATION METHOD: protein sequencing
        (D) OTHER INFORMATION: positively identified amino acids in
            GTVap protein sequence; used for the design of
            oligonucleotide probes (xi) SEQUENCE DESCRIPTION: SEQ ID NO: 5:

Ile Leu Gln Asn Gln Ile Gln Gln Gln Thr Arg Thr Asp Glu Gly
              5                  10                  15

(2) INFORMATION FOR SEQ ID NO: 6:

(i) SEQUENCE CHARACTERISTICS:
        (A) LENGTH: 45 nucleotides
        (B) TYPE: nucleic acid
        (C) STRANDEDNESS: single
        (D) TOPOLOGY: linear (ii) MOLECULE TYPE: Other nucleic Acid: synthetic oligonucleotide
        probe based on peptide sequence (iii) HYPOTHETICAL: yes (iv) ANTI-SENSE: no (xi) SEQUENCE DESCRIPTION: SEQ ID NO: 6:

ATHYTNCARA AYCARATHCA RCARCARACN MGNACNGAYG ARGGN        45

(2) INFORMATION FOR SEQ ID NO: 7:

(i) SEQUENCE CHARACTERISTICS:
        (A) LENGTH: 45 nucleotides
        (B) TYPE: nucleic acid
        (C) STRANDEDNESS: single
        (D) TOPOLOGY: linear (ii) MOLECULE TYPE: Other nucleic Acid: synthetic oligonucleotide
        probe based on peptide sequence (iii) HYPOTHETICAL: yes (iv) ANTI-SENSE: yes (xi) SEQUENCE DESCRIPTION: SEQ ID NO: 7:

NCCYTCRTCN GTNCKNGTYT GYTGYTGDAT YTGRTTYTGN ARDAT          45

(2) INFORMATION FOR SEQ ID NO: 8:

(i) SEQUENCE CHARACTERISTICS:
        (A) LENGTH: 12 amino acids
        (B) TYPE: amino acid
        (D) TOPOLOGY: linear (ii) MOLECULE TYPE: synthetic peptide
        (A) DESCRIPTION: synthetic peptide designed from GTVap p94
            fragment and modified with a carboxyl terminal cysteine (xi) SEQUENCE DESCRIPTION: SEQ ID NO: 8:

Phe Ala Ala Thr Gln Phe Glu Pro Leu Ala Ala Cys
                 5                   10

(2) INFORMATION FOR SEQ ID NO: 9:

(i) SEQUENCE CHARACTERISTICS:
        (A) LENGTH: 16 amino acids
        (B) TYPE: amino acid
        (D) TOPOLOGY: linear (ii) MOLECULE TYPE: synthetic peptide
        (A) DESCRIPTION: synthetic peptide designed from GLUT4
            protein sequence amino acids 495-509 and modified
            with an amino terminal cysteine (xi) SEQUENCE DESCRIPTION: SEQ ID NO: 9:

Cys Lys Pro Ser Thr Glu Leu Glu Tyr Leu Gly Pro Asp Glu Asn Asp
                 5                   10                  15

(2) INFORMATION FOR SEQ ID NO: 10:

(i) SEQUENCE CHARACTERISTICS:
        (A) LENGTH: 8 amino acids
        (B) TYPE: amino acid
        (D) TOPOLOGY: linear (ii) MOLECULE TYPE: synthetic peptide
        (A) DESCRIPTION: synthetic peptide designed from GLUT4 protein
            sequence amino acids 495-501 and modified with a carboxyl
            terminal cysteine (xi) SEQUENCE DESCRIPTION: SEQ ID NO: 10:

Lys Pro Ser Thr Glu Leu Glu Cys
                 5

(2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear (ii) MOLECULE TYPE: synthetic peptide
        (A) DESCRIPTION: synthetic peptide designed from GLUT4 protein
            sequence amino acids 498-503 and modified with a
            carboxyl terminal cysteine (xi) SEQUENCE DESCRIPTION: SEQ ID NO: 11:

Thr Glu Leu Glu Tyr Leu Cys
                 5

(2) INFORMATION FOR SEQ ID NO: 12:

(i) SEQUENCE CHARACTERISTICS:

(A) LENGTH: 7 amino acids
            (B) TYPE: amino acid
            (D) TOPOLOGY: linear (ii) MOLECULE TYPE: synthetic peptide
            (A) DESCRIPTION: synthetic peptide designed from GLUT4
                protein sequence amino acids 504-509 and modified
                with an amino terminal cysteine (xi) SEQUENCE DESCRIPTION: SEQ ID NO: 12:

Cys Gly Pro Asp Glu Asn Asp
                5

(2) INFORMATION FOR SEQ ID NO: 13:

(i) SEQUENCE CHARACTERISTICS:
            (A) LENGTH: 12 amino acids
            (B) TYPE: amino acid
            (D) TOPOLOGY: linear (ii) MOLECULE TYPE: protein fragment
            (A) DESCRIPTION: tryptic digest polypeptide from full length
                protein (v) FRAGMENT TYPE: internal fragment (vi) ORIGINAL SOURCE:
            (A) ORGANISM: Rattus norvegicus
            (B) STRAIN: Sprague-Dawley
            (F) TISSUE TYPE: adipose (ix) FEATURE:
            (C) IDENTIFICATION METHOD: protein sequencing
            (D) OTHER INFORMATION: GTVap1 peptide sequence including
                residues assigned with less than full confidence (xi) SEQUENCE DESCRIPTION: SEQ ID NO: 13:

Phe Ala Ala Thr Gln Phe Glu Pro Leu Ala Ala Arg
                5                   10

(2) INFORMATION FOR SEQ ID NO: 14:

(i) SEQUENCE CHARACTERISTICS:
            (A) LENGTH: 19 amino acids
            (B) TYPE: amino acid
            (D) TOPOLOGY: linear (ii) MOLECULE TYPE: protein fragment
            (A) DESCRIPTION: tryptic digest polypeptide from full length
                protein (v) FRAGMENT TYPE: internal fragment (vi) ORIGINAL SOURCE:
            (A) ORGANISM: Rattus norvegicus
            (B) STRAIN: Sprague-Dawley
            (F) TISSUE TYPE: adipose (ix) FEATURE:
            (C) IDENTIFICATION METHOD: protein sequencing
            (D) OTHER INFORMATION: GTVap2 sequence including residues
                assigned with less than full confidence; see
                OTHER INFORMATION on SEQ ID NO: 2

(xi) SEQUENCE DESCRIPTION: SEQ ID NO: 14:

Ile Leu Gln Asn Gln Ile Gln Gln Gln Thr Arg Thr Asp Glu Gly Thr
                5                   10                  15
Pro Asn Met (2) INFORMATION FOR SEQ ID NO: 15:

(i) SEQUENCE CHARACTERISTICS:
            (A) LENGTH: 3388 base pairs (B) TYPE: nucleic acid
(C) STRANDEDNESS: single
(D) TOPOLOGY: linear (ii) MOLECULE TYPE: cDNA to mRNA;

(vi) ORIGINAL SOURCE:
(A) ORGANISM: Rattus norvegicus
(B) STRAIN: Sprague-Dawley
(D) DEVELOPMENTAL STAGE: adult
(F) TISSUE TYPE: skeletal muscle (vii) IMMEDIATE SOURCE:
(A) LIBRARY: Clontech rat skeletal muscle cDNA library in lambda gt11 and mRNA isolated from rat skeletal muscle
(B) CLONE: 5.3 (from lambda gt11 library), PCR product clones 5, 334, and KC44.

(ix) FEATURE:
(A) NAME/KEY: cDNA includes complete coding region for GTVap, long version
(C) IDENTIFICATION METHOD: nucleic acid hybridization (xi) SEQUENCE DESCRIPTION: SEQ ID NO: 15:

```
CTCTCGGAGT AGAAAGCTTG GGGCGCTGGG CTGGTGAGGA CCCGCAGCGG GCGAAG ATG          59
                                                               Met
                                                                1

GAG ACC TTT ACC AAT GAT CGA CTT CAG CTT CCA AGG AAT ATG ATT GAA           107
Glu Thr Phe Thr Asn Asp Arg Leu Gln Leu Pro Arg Asn Met Ile Glu
             5                  10                  15

AAC AGC ATG TTT GAA GAA GAA CCA GAT GTG GTA GAT TTA GCC AAA GAA           155
Asn Ser Met Phe Glu Glu Glu Pro Asp Val Val Asp Leu Ala Lys Glu
         20                  25                  30

CCT TGT TTA CAT CCT CTG GAA CCT GAT GAA GTT GAA TAT GAG CCC CGA           203
Pro Cys Leu His Pro Leu Glu Pro Asp Glu Val Glu Tyr Glu Pro Arg
     35                  40                  45

GGT TCG AGG CTT CTG GTG AGA GGT CTT GGT GAG CAT GAG ATG GAT GAG           251
Gly Ser Arg Leu Leu Val Arg Gly Leu Gly Glu His Glu Met Asp Glu
 50                  55                  60                  65

GAT GAA GAG GAT TAT GAG TCA TCT GCC AAG CTG CTG GGC ATG TCC TTC           299
Asp Glu Glu Asp Tyr Glu Ser Ser Ala Lys Leu Leu Gly Met Ser Phe
                 70                  75                  80

ATG AAC AGA AGC TCA GGC CTT CGG AAC AGT GCA ACA GGC TAC AGG CAG           347
Met Asn Arg Ser Ser Gly Leu Arg Asn Ser Ala Thr Gly Tyr Arg Gln
             85                  90                  95

AGT CCA GAT GGG ACT TGT TCA GTA CCC TCT GCC AGG ACC TTA GTA ATC           395
Ser Pro Asp Gly Thr Cys Ser Val Pro Ser Ala Arg Thr Leu Val Ile
        100                 105                 110

TGT GTT TTT GTC ATT GTG GTT GCT GTC TCT GTA ATC ATG GTG ATT TAT           443
Cys Val Phe Val Ile Val Val Ala Val Ser Val Ile Met Val Ile Tyr
    115                 120                 125

CTA CTG CCT AGA TGT ACC TTT ACC AAA GAA GGC TGC CAC AAA ACA AAC           491
Leu Leu Pro Arg Cys Thr Phe Thr Lys Glu Gly Cys His Lys Thr Asn
130                 135                 140                 145

CAG TCA GCA GAA CTC ATT CAG CCG ATT GCT ACA AAC GGG AAA GTG TTT           539
Gln Ser Ala Glu Leu Ile Gln Pro Ile Ala Thr Asn Gly Lys Val Phe
                150                 155                 160

CCA TGG GCA CAA ATT AGG CTT CCC ACT GCC ATT ATT CCT CAA CGC TAT           587
Pro Trp Ala Gln Ile Arg Leu Pro Thr Ala Ile Ile Pro Gln Arg Tyr
            165                 170                 175

GAA CTT AGC CTA CAT CCA AAC CTA ACC TCA ATG ACA TTC AGG GGT TCT           635
Glu Leu Ser Leu His Pro Asn Leu Thr Ser Met Thr Phe Arg Gly Ser
        180                 185                 190

GTG ACA ATT TCA CTT CAG GCT CTT CAA GAT ACA CGG GAC ATC ATT CTC           683
Val Thr Ile Ser Leu Gln Ala Leu Gln Asp Thr Arg Asp Ile Ile Leu
    195                 200                 205
```

-continued

```
CAT AGC ACA GGA CAT AAT ATT TCA AGT GTG ACA TTT ATG TCG GCG GTT      731
His Ser Thr Gly His Asn Ile Ser Ser Val Thr Phe Met Ser Ala Val
210             215                 220                 225

TCC AGT CAA GAA AAA CAA GTT GAA ATT CTG GAA TAT CCA TAT CAT GAA      779
Ser Ser Gln Glu Lys Gln Val Glu Ile Leu Glu Tyr Pro Tyr His Glu
                230                 235                 240

CAA ATC GCC GTT GTT GCC CCT GAA AGC CTT CTA ACA GGA CAC AAT TAT      827
Gln Ile Ala Val Val Ala Pro Glu Ser Leu Leu Thr Gly His Asn Tyr
            245                 250                 255

ACC TTG AAG ATA GAA TAT TCA GCA AAT ATA TCT AAC TCT TAC TAT GGG      875
Thr Leu Lys Ile Glu Tyr Ser Ala Asn Ile Ser Asn Ser Tyr Tyr Gly
        260                 265                 270

TTT TAT GGC ATC ACC TAC ACA GAT AAA AGT AAT GAG AAA AAG AAC TTT      923
Phe Tyr Gly Ile Thr Tyr Thr Asp Lys Ser Asn Glu Lys Lys Asn Phe
275                 280                 285

GCA GCA ACT CAG TTT GAA CCT TTG GCA GCA AGA TCT GCT TTT CCT TGT      971
Ala Ala Thr Gln Phe Glu Pro Leu Ala Ala Arg Ser Ala Phe Pro Cys
290                 295                 300                 305

TTT GAT GAA CCA GCA TTT AAG GCC ACA TTT ATC ATC AAG ATC ACA AGG     1019
Phe Asp Glu Pro Ala Phe Lys Ala Thr Phe Ile Ile Lys Ile Thr Arg
                310                 315                 320

GAT GAG CAC CAT ACT GCA TTA TCA AAT ATG CCT AAG AAG TCA TCA GTC     1067
Asp Glu His His Thr Ala Leu Ser Asn Met Pro Lys Lys Ser Ser Val
            325                 330                 335

CCT ACA GAA GAA GGA CTT ATT CAA GAT GAG TTT TCT GAA AGT GTG AAA     1115
Pro Thr Glu Glu Gly Leu Ile Gln Asp Glu Phe Ser Glu Ser Val Lys
        340                 345                 350

ATG AGC ACA TAC CTG GTT GCT TTC ATT GTA GGG GAG ATG AGG AAC CTG     1163
Met Ser Thr Tyr Leu Val Ala Phe Ile Val Gly Glu Met Arg Asn Leu
355                 360                 365

AGT CAG GAT GTA AAC GGG ACT CTG GTT TCT GTA TAT GCT GTA CCA GAA     1211
Ser Gln Asp Val Asn Gly Thr Leu Val Ser Val Tyr Ala Val Pro Glu
370                 375                 380                 385

AAA ATT GAT CAA GTT TAC CAT GCC TTG GAC ACA ACT GTA AAG CTC CTT     1259
Lys Ile Asp Gln Val Tyr His Ala Leu Asp Thr Thr Val Lys Leu Leu
                390                 395                 400

GAG TTT TAT CAA AAT TAC TTT GAA ATT CAA TAC CCA CTA AAG AAA TTG     1307
Glu Phe Tyr Gln Asn Tyr Phe Glu Ile Gln Tyr Pro Leu Lys Lys Leu
            405                 410                 415

GAT CTG GTG GCC ATT CCT GAC TTT GAA GCA GGA GCA ATG GAA AAT TGG     1355
Asp Leu Val Ala Ile Pro Asp Phe Glu Ala Gly Ala Met Glu Asn Trp
        420                 425                 430

GGC CTG CTT ACG TTC CGA GAA GAG ACT CTT CTG TAT GAC AAT GCC ACT     1403
Gly Leu Leu Thr Phe Arg Glu Glu Thr Leu Leu Tyr Asp Asn Ala Thr
435                 440                 445

TCT TCA GTA GCA GAT AGA AAA CTG GTC ACT AAA ATC ATC GCT CAC GAG     1451
Ser Ser Val Ala Asp Arg Lys Leu Val Thr Lys Ile Ile Ala His Glu
450                 455                 460                 465

CTG GCA CAT CAG TGG TTT GGT AAT CTG GTT ACA ATG CAG TGG TGG AAT     1499
Leu Ala His Gln Trp Phe Gly Asn Leu Val Thr Met Gln Trp Trp Asn
                470                 475                 480

GAC CTG TGG CTA AAC GAA GGC TTT GCC ACT TTC ATG GAG TAT TTC TCT     1547
Asp Leu Trp Leu Asn Glu Gly Phe Ala Thr Phe Met Glu Tyr Phe Ser
            485                 490                 495

GTG GAA AAA ATA TTC AAA GAG CTC AAC AGT TAT GAA GAC TTC TTA GAT     1595
Val Glu Lys Ile Phe Lys Glu Leu Asn Ser Tyr Glu Asp Phe Leu Asp
        500                 505                 510

GCT CGA TTT AAA ACC ATG AGG AAA GAT TCC TTG AAT TCG TCT CAT CCA     1643
Ala Arg Phe Lys Thr Met Arg Lys Asp Ser Leu Asn Ser Ser His Pro
515                 520                 525
```

```
ATA TCA TCA TCT GTT CAG TCA TCA GAA CAA ATA GAA GAA ATG TTT GAT    1691
Ile Ser Ser Ser Val Gln Ser Ser Glu Gln Ile Glu Glu Met Phe Asp
530             535                 540                 545

TCT CTT TCG TAT TTT AAG CAG GGA GCG TCT CTC TTG TTG ATG TTG AAA    1739
Ser Leu Ser Tyr Phe Lys Gln Gly Ala Ser Leu Leu Leu Met Leu Lys
                550                 555                 560

AGT TAC CTT AGT GAA GAC GTG TTT CAG CAT GCC ATC ATT CTT TAC CTG    1787
Ser Tyr Leu Ser Glu Asp Val Phe Gln His Ala Ile Ile Leu Tyr Leu
            565                 570                 575

CAC AAT CAC AGC TAT GCA GCA ATT CAA AGC GAT GAC CTC TGG GAC AGC    1835
His Asn His Ser Tyr Ala Ala Ile Gln Ser Asp Asp Leu Trp Asp Ser
        580                 585                 590

TTC AAT GAG GTC ACA GGC AAA ACT CTA GAT GTA AAG AAA ATG ATG AAA    1883
Phe Asn Glu Val Thr Gly Lys Thr Leu Asp Val Lys Lys Met Met Lys
595             600                 605

ACC TGG ACC CTA CAG AAA GGA TTC CCA TTA GTG ACC GTC CAG AGA AAG    1931
Thr Trp Thr Leu Gln Lys Gly Phe Pro Leu Val Thr Val Gln Arg Lys
610             615                 620                 625

GGG ACT GAG CTT CTT CTA CAA CAA GAA AGA TTT TTT CCA AGC ATG CAA    1979
Gly Thr Glu Leu Leu Leu Gln Gln Glu Arg Phe Phe Pro Ser Met Gln
                630                 635                 640

CCA GAA ATT CAG GAT TCA GAT ACA AGC CAC CTT TGG CAT ATT CCA ATA    2027
Pro Glu Ile Gln Asp Ser Asp Thr Ser His Leu Trp His Ile Pro Ile
                645                 650                 655

TCC TAT GTC ACT GAT GGA AGA AAC TAT TCA GAA TAT CGA TCA GTT TCA    2075
Ser Tyr Val Thr Asp Gly Arg Asn Tyr Ser Glu Tyr Arg Ser Val Ser
            660                 665                 670

CTA CTG GAC AAG AAA TCA GAT GTC ATC AAT CTT ACA GAA CAA GTA CAA    2123
Leu Leu Asp Lys Lys Ser Asp Val Ile Asn Leu Thr Glu Gln Val Gln
675             680                 685

TGG GTC AAA GTC AAT ACA AAC ATG ACG GGC TAC TAC ATT GTT CAC TAT    2171
Trp Val Lys Val Asn Thr Asn Met Thr Gly Tyr Tyr Ile Val His Tyr
690             695                 700                 705

GCT CAT GAT GGC TGG GCA GCT CTA ATC AAC CAG TTA AAA AGA AAT CCC    2219
Ala His Asp Gly Trp Ala Ala Leu Ile Asn Gln Leu Lys Arg Asn Pro
            710                 715                 720

TAT GTT CTG AGT GAC AAA GAC CGA GCC AAC CTG ATC AAT AAC ATC TTT    2267
Tyr Val Leu Ser Asp Lys Asp Arg Ala Asn Leu Ile Asn Asn Ile Phe
        725                 730                 735

GAA CTT GCA GGC CTT GGC AAA GTG CCT CTT CAG ATG GCA TTC GAT TTG    2315
Glu Leu Ala Gly Leu Gly Lys Val Pro Leu Gln Met Ala Phe Asp Leu
    740                 745                 750

ATT GAC TAC CTT AGA AAT GAG ACC CAC ACT GCA CCT ATC ACT GAA GCC    2363
Ile Asp Tyr Leu Arg Asn Glu Thr His Thr Ala Pro Ile Thr Glu Ala
755             760                 765

CTG TTC CAG ACT GAC CTC ATC TAT AAT CTC CTG GAA AAA CTG GGA CAC    2411
Leu Phe Gln Thr Asp Leu Ile Tyr Asn Leu Leu Glu Lys Leu Gly His
770             775                 780                 785

ATG GAC CTG TCC TCA AGA TTA GTG ACC AGA GTA CAT AAA TTG CTC CAG    2459
Met Asp Leu Ser Ser Arg Leu Val Thr Arg Val His Lys Leu Leu Gln
                790                 795                 800

AAC CAA ATC CAG CAG CAG ACA TGG ACA GAT GAA GGC ACA CCA TCC ATG    2507
Asn Gln Ile Gln Gln Gln Thr Trp Thr Asp Glu Gly Thr Pro Ser Met
                805                 810                 815

CGA GAG CTT CGG TCA GCC TTG CTG GAA TTT GCC TGC GCC CAC AGC CTA    2555
Arg Glu Leu Arg Ser Ala Leu Leu Glu Phe Ala Cys Ala His Ser Leu
            820                 825                 830

GAG AAC TGT ACC ACT ATG GCC ACA AAG CTG TTT GAT GGT TGG ATG GCA    2603
Glu Asn Cys Thr Thr Met Ala Thr Lys Leu Phe Asp Gly Trp Met Ala
        835                 840                 845
```

-continued

```
TCA AAT GGA ACT CAG AGC CTG CCG ACT GAC GTC ATG ACC ACT GTG TTC    2651
Ser Asn Gly Thr Gln Ser Leu Pro Thr Asp Val Met Thr Thr Val Phe
850                 855                 860                 865

AAA GTT GGA GCA AGA ACC GAG AAA GGC TGG TTG TTC CTC TTT AGC ATG    2699
Lys Val Gly Ala Arg Thr Glu Lys Gly Trp Leu Phe Leu Phe Ser Met
            870                 875                 885

TAC TCC TCC ATG GGC TCT GAA GCA GAG AAG GAT AAA ATA CTT GAA GCC    2747
Tyr Ser Ser Met Gly Ser Glu Ala Glu Lys Asp Lys Ile Leu Glu Ala
                890                 880                 895

CTG GCC AGC TCA GCG GAT GCA CAT AAA CTT TAC TGG TTA ATG AAA AGT    2795
Leu Ala Ser Ser Ala Asp Ala His Lys Leu Tyr Trp Leu Met Lys Ser
            900                 905                 910

AGC CTT GAT GGT GAT ATC ATT CGG ACA CAG AAG TTG TCA CTT ATC ATT    2843
Ser Leu Asp Gly Asp Ile Ile Arg Thr Gln Lys Leu Ser Leu Ile Ile
            915                 920                 925

AGA ACA GTG GGC AGA CAG TTT CCT GGA CAT TTG CTG GCA TGG GAT TTT    2891
Arg Thr Val Gly Arg Gln Phe Pro Gly His Leu Leu Ala Trp Asp Phe
930                 935                 940                 945

GTT AAG GAA AAC TGG AAT AAG CTT GTA CAT AAG TTC CAT CTG GGC TCC    2939
Val Lys Glu Asn Trp Asn Lys Leu Val His Lys Phe His Leu Gly Ser
            950                 955                 960

TAT ACC ATT CAA AGC ATT GTT GCT GGA TCT ACT CAC TTA TTT TCA ACG    2987
Tyr Thr Ile Gln Ser Ile Val Ala Gly Ser Thr His Leu Phe Ser Thr
            965                 970                 975

AAG ACA CAT TTA TCT GAG GTC CAG GAA TTC TTC GAA AAT CAG TCA GAG    3035
Lys Thr His Leu Ser Glu Val Gln Glu Phe Phe Glu Asn Gln Ser Glu
            980                 985                 990

GCA ACC TTG CAG CTT CGG TGT GTT CAG GAG GCC TTC GAA GTG ATT GAG    3083
Ala Thr Leu Gln Leu Arg Cys Val Gln Glu Ala Phe Glu Val Ile Glu
            995                 1000                1005

CTG AAT ATC CAG TGG ATG GCC AGG AAT CTG AAA ACT CTG ACA CTG TGG    3131
Leu Asn Ile Gln Trp Met Ala Arg Asn Leu Lys Thr Leu Thr Leu Trp
1010                1015                1020

CTG TAGCCCTCAC AGCTGATCTT CCGGTGCCCA TGGCTCTGCT GCTTTTGCAA         3184
Leu

AGGTTGAGTG AAGGCCGGCC TGCTACTGAG TTGTTTGCAC TGTTAGGATC TAGTTAGCTC  3244

AGGGCCCAAT TGTATTTTTC ATATCTTTTC TGAAATGTCC TTAGGCGGTA GTTATTTATT  3304

ACAAAATTAT ATTCACCTGT ACGTCAACCA TCTACAATAA CAGTGAAGAC CTGCCCGCGC  3364

GGCCGCTCGA GCCCTATAGT GAGT                                         3388
```

(2) INFORMATION FOR SEQ ID NO: 16:

(i) SEQUENCE CHARACTERISTICS:
        (A) LENGTH: 3385 base pairs
        (B) TYPE: nucleic acid
        (C) STRANDEDNESS: single
        (D) TOPOLOGY: linear (ii) MOLECULE TYPE: cDNA to mRNA;

(vi) ORIGINAL SOURCE:
        (A) ORGANISM: Rattus norvegicus
        (B) STRAIN: Sprague-Dawley
        (D) DEVELOPMENTAL STAGE: adult
        (F) TISSUE TYPE: skeletal muscle (vii) IMMEDIATE SOURCE:
        (A) LIBRARY: Clontech rat skeletal muscle cDNA library in
            lambda gt11 and mRNA isolated from rat skeletal muscle
        (B) CLONE: 12.1 (from lambda gt11 library), PCR product
            clones 5, 334, and KC44.

(ix) FEATURE:

(A) NAME/KEY: cDNA includes complete coding region for GTVap,
           shor version
       (C) IDENTIFICATION METHOD: nucleic acid hybridization (xi) SEQUENCE DESCRIPTION: SEQ ID NO: 16:

CTCTCGGAGT AGAAAGCTTG GGGCGCTGGG CTGGTGAGGA CCCGCAGCGG GCGAAG ATG        59
                                                                Met
                                                                 1

GAG ACC TTT ACC AAT GAT CGA CTT CAG CTT CCA AGG AAT ATG ATT GAA         107
Glu Thr Phe Thr Asn Asp Arg Leu Gln Leu Pro Arg Asn Met Ile Glu
            5                  10                  15

AAC AGC ATG TTT GAA GAA GAA CCA GAT GTG GTA GAT TTA GCC AAA GAA         155
Asn Ser Met Phe Glu Glu Glu Pro Asp Val Val Asp Leu Ala Lys Glu
         20                  25                  30

CCT TGT TTA CAT CCT CTG GAA CCT GAT GAA GTT GAA TAT GAG CCC CGA         203
Pro Cys Leu His Pro Leu Glu Pro Asp Glu Val Glu Tyr Glu Pro Arg
     35                  40                  45

GGT TCG AGG CTT CTG GTG AGA GGT CTT GGT GAG CAT GAG ATG GAT GAG         251
Gly Ser Arg Leu Leu Val Arg Gly Leu Gly Glu His Glu Met Asp Glu
 50                  55                  60                  65

GAT GAA GAG GAT TAT GAG TCA TCT GCC AAG CTG CTG GGC ATG TCC TTC         299
Asp Glu Glu Asp Tyr Glu Ser Ser Ala Lys Leu Leu Gly Met Ser Phe
                 70                  75                  80

ATG AAC AGA AGC TCA GGC CTT CGG AAC AGT GCA ACA GGC TAC AGG CAG         347
Met Asn Arg Ser Ser Gly Leu Arg Asn Ser Ala Thr Gly Tyr Arg Gln
             85                  90                  95

AGT CCA GAT GGG ACT TGT TCA GTA CCC TCT GCC AGG ACC TTA GTA ATC         395
Ser Pro Asp Gly Thr Cys Ser Val Pro Ser Ala Arg Thr Leu Val Ile
         100                 105                 110

TGT GTT TTT GTC ATT GTG GTT GCT GTC TCT GTA ATC ATG GTG ATT TAT         443
Cys Val Phe Val Ile Val Val Ala Val Ser Val Ile Met Val Ile Tyr
     115                 120                 125

CTA CTG CCT AGA TGT ACC TTT ACC AAA GAA GGC TGC CAC AAA ACA AAC         491
Leu Leu Pro Arg Cys Thr Phe Thr Lys Glu Gly Cys His Lys Thr Asn
130                 135                 140                 145

CAG TCA GCA GAA CTC ATT CAG CCG ATT GCT ACA AAC GGG AAA GTG TTT         539
Gln Ser Ala Glu Leu Ile Gln Pro Ile Ala Thr Asn Gly Lys Val Phe
                 150                 155                 160

CCA TGG GCA CAA ATT AGG CTT CCC ACT GCC ATT ATT CCT CAA CGC TAT         587
Pro Trp Ala Gln Ile Arg Leu Pro Thr Ala Ile Ile Pro Gln Arg Tyr
             165                 170                 175

GAA CTT AGC CTA CAT CCA AAC CTA ACC TCA ATG ACA TTC AGG GGT TCT         635
Glu Leu Ser Leu His Pro Asn Leu Thr Ser Met Thr Phe Arg Gly Ser
         180                 185                 190

GTG ACA ATT TCA CTT CAG GCT CTT CAA GAT ACA CGG GAC ATC ATT CTC         683
Val Thr Ile Ser Leu Gln Ala Leu Gln Asp Thr Arg Asp Ile Ile Leu
     195                 200                 205

CAT AGC ACA GGA CAT AAT ATT TCA AGT GTG ACA TTT ATG TCG GCG GTT         731
His Ser Thr Gly His Asn Ile Ser Ser Val Thr Phe Met Ser Ala Val
210                 215                 220                 225

TCC AGT CAA GAA AAA CAA GTT GAA ATT CTG GAA TAT CCA TAT CAT GAA         779
Ser Ser Gln Glu Lys Gln Val Glu Ile Leu Glu Tyr Pro Tyr His Glu
                 230                 235                 240

CAA ATC GCC GTT GTT GCC CCT GAA AGC CTT CTA ACA GGA CAC AAT TAT         827
Gln Ile Ala Val Val Ala Pro Glu Ser Leu Leu Thr Gly His Asn Tyr
             245                 250                 255

ACC TTG AAG ATA GAA TAT TCA GCA AAT ATA TCT AAC TCT TAC TAT GGG         875
Thr Leu Lys Ile Glu Tyr Ser Ala Asn Ile Ser Asn Ser Tyr Tyr Gly
         260                 265                 270

TTT TAT GGC ATC ACC TAC ACA GAT AAA AGT AAT GAG AAA AAG AAC TTT         923
Phe Tyr Gly Ile Thr Tyr Thr Asp Lys Ser Asn Glu Lys Lys Asn Phe

-continued

| | | | | |
|---|---|---|---|---|
| 275 | | 280 | | 285 |

GCA GCA ACT CAG TTT GAA CCT TTG GCA GCA AGA TCT GCT TTT CCT TGT    971
Ala Ala Thr Gln Phe Glu Pro Leu Ala Ala Arg Ser Ala Phe Pro Cys
290                     295                 300                 305

TTT GAT GAA CCA GCA TTT AAG GCC ACA TTT ATC ATC AAG ATC ACA AGG   1019
Phe Asp Glu Pro Ala Phe Lys Ala Thr Phe Ile Ile Lys Ile Thr Arg
        310                 315                 320

GAT GAG CAC CAT ACT GCA TTA TCA AAT ATG CCT AAG AAG TCA TCA GTC   1067
Asp Glu His His Thr Ala Leu Ser Asn Met Pro Lys Lys Ser Ser Val
                325                 330                 335

CCT ACA GAA GAA GGA CTT ATT CAA GAT GAG TTT TCT GAA AGT GTG AAA   1115
Pro Thr Glu Glu Gly Leu Ile Gln Asp Glu Phe Ser Glu Ser Val Lys
        340                 345                 350

ATG AGC ACA TAC CTG GTT GCT TTC ATT GTA GGG GAG ATG AGG AAC CTG   1163
Met Ser Thr Tyr Leu Val Ala Phe Ile Val Gly Glu Met Arg Asn Leu
355                 360                 365

AGT CAG GAT GTA AAC GGG ACT CTG GTT TCT GTA TAT GCT GTA CCA GAA   1211
Ser Gln Asp Val Asn Gly Thr Leu Val Ser Val Tyr Ala Val Pro Glu
370                 375                 380                 385

AAA ATT GAT CAA GTT TAC CAT GCC TTG GAC ACA ACT GTA AAG CTC CTT   1259
Lys Ile Asp Gln Val Tyr His Ala Leu Asp Thr Thr Val Lys Leu Leu
        390                 395                 400

GAG TTT TAT CAA AAT TAC TTT GAA ATT CAA TAC CCA CTA AAG AAA TTG   1307
Glu Phe Tyr Gln Asn Tyr Phe Glu Ile Gln Tyr Pro Leu Lys Lys Leu
        405                 410                 415

GAT CTG GTG GCC ATT CCT GAC TTT GAA GCA GGA GCA ATG GAA AAT TGG   1355
Asp Leu Val Ala Ile Pro Asp Phe Glu Ala Gly Ala Met Glu Asn Trp
        420                 425                 430

GGC CTG CTT ACG TTC CGA GAA GAG ACT CTT CTG TAT GAC AAT GCC ACT   1403
Gly Leu Leu Thr Phe Arg Glu Glu Thr Leu Leu Tyr Asp Asn Ala Thr
435                 440                 445

TCT TCA GTA GCA GAT AGA AAA CTG GTC ACT AAA ATC ATC GCT CAC GAG   1451
Ser Ser Val Ala Asp Arg Lys Leu Val Thr Lys Ile Ile Ala His Glu
450                 455                 460                 465

CTG GCA CAT CAG TGG TTT GGT AAT CTG GTT ACA ATG CAG TGG TGG AAT   1499
Leu Ala His Gln Trp Phe Gly Asn Leu Val Thr Met Gln Trp Trp Asn
                470                 475                 480

GAC CTG TGG CTA AAC GAA GGC TTT GCC ACT TTC ATG GAG TAT TTC TCT   1547
Asp Leu Trp Leu Asn Glu Gly Phe Ala Thr Phe Met Glu Tyr Phe Ser
        485                 490                 495

GTG GAA AAA ATA TTC AAA GAG CTC AAC AGT TAT GAA GAC TTC TTA GAT   1595
Val Glu Lys Ile Phe Lys Glu Leu Asn Ser Tyr Glu Asp Phe Leu Asp
        500                 505                 510

GCT CGA TTT AAA ACC ATG AGG AAA GAT TCC TTG AAT TCG TCT CAT CCA   1643
Ala Arg Phe Lys Thr Met Arg Lys Asp Ser Leu Asn Ser Ser His Pro
515                 520                 525

ATA TCA TCA TCT GTT CAG TCA TCA GAA CAA ATA GAA GAA ATG TTT GAT   1691
Ile Ser Ser Ser Val Gln Ser Ser Glu Gln Ile Glu Glu Met Phe Asp
530                 535                 540                 545

TCT CTT TCG TAT TTT AAG GGA GCG TCT CTC TTG TTG ATG TTG AAA AGT   1739
Ser Leu Ser Tyr Phe Lys Gly Ala Ser Leu Leu Leu Met Leu Lys Ser
                550                 555                 560

TAC CTT AGT GAA GAC GTG TTT CAG CAT GCC ATC ATT CTT TAC CTG CAC   1787
Tyr Leu Ser Glu Asp Val Phe Gln His Ala Ile Ile Leu Tyr Leu His
        565                 570                 575

AAT CAC AGC TAT GCA GCA ATT CAA AGC GAT GAC CTC TGG GAC AGC TTC   1835
Asn His Ser Tyr Ala Ala Ile Gln Ser Asp Asp Leu Trp Asp Ser Phe
        580                 585                 590

AAT GAG GTC ACA GGC AAA ACT CTA GAT GTA AAG AAA ATG ATG AAA ACC   1883
Asn Glu Val Thr Gly Lys Thr Leu Asp Val Lys Lys Met Met Lys Thr

```
                    595                      600                      605
TGG ACC CTA CAG AAA GGA TTC CCA TTA GTG ACC GTC CAG AGA AAG GGG          1931
Trp Thr Leu Gln Lys Gly Phe Pro Leu Val Thr Val Gln Arg Lys Gly
610                 615                      620                      625

ACT GAG CTT CTT CTA CAA CAA GAA AGA TTT TTT CCA AGC ATG CAA CCA          1979
Thr Glu Leu Leu Leu Gln Gln Glu Arg Phe Phe Pro Ser Met Gln Pro
                    630                      635                      640

GAA ATT CAG GAT TCA GAT ACA AGC CAC CTT TGG CAT ATT CCA ATA TCC          2027
Glu Ile Gln Asp Ser Asp Thr Ser His Leu Trp His Ile Pro Ile Ser
                        645                      650                      655

TAT GTC ACT GAT GGA AGA AAC TAT TCA GAA TAT CGA TCA GTT TCA CTA          2075
Tyr Val Thr Asp Gly Arg Asn Tyr Ser Glu Tyr Arg Ser Val Ser Leu
                660                      665                      670

CTG GAC AAG AAA TCA GAT GTC ATC AAT CTT ACA GAA CAA GTA CAA TGG          2123
Leu Asp Lys Lys Ser Asp Val Ile Asn Leu Thr Glu Gln Val Gln Trp
            675                      680                      685

GTC AAA GTC AAT ACA AAC ATG ACG GGC TAC TAC ATT GTT CAC TAT GCT          2171
Val Lys Val Asn Thr Asn Met Thr Gly Tyr Tyr Ile Val His Tyr Ala
690                      695                      700                      705

CAT GAT GGC TGG GCA GCT CTA ATC AAC CAG TTA AAA AGA AAT CCC TAT          2219
His Asp Gly Trp Ala Ala Leu Ile Asn Gln Leu Lys Arg Asn Pro Tyr
                    710                      715                      720

GTT CTG AGT GAC AAA GAC CGA GCC AAC CTG ATC AAT AAC ATC TTT GAA          2267
Val Leu Ser Asp Lys Asp Arg Ala Asn Leu Ile Asn Asn Ile Phe Glu
                725                      730                      735

CTT GCA GGC CTT GGC AAA GTG CCT CTT CAG ATG GCA TTC GAT TTG ATT          2315
Leu Ala Gly Leu Gly Lys Val Pro Leu Gln Met Ala Phe Asp Leu Ile
            740                      745                      750

GAC TAC CTT AGA AAT GAG ACC CAC ACT GCA CCT ATC ACT GAA GCC CTG          2363
Asp Tyr Leu Arg Asn Glu Thr His Thr Ala Pro Ile Thr Glu Ala Leu
755                      760                      765

TTC CAG ACT GAC CTC ATC TAT AAT CTC CTG GAA AAA CTG GGA CAC ATG          2411
Phe Gln Thr Asp Leu Ile Tyr Asn Leu Leu Glu Lys Leu Gly His Met
770                      775                      780                      785

GAC CTG TCC TCA AGA TTA GTG ACC AGA GTA CAT AAA TTG CTC CAG AAC          2459
Asp Leu Ser Ser Arg Leu Val Thr Arg Val His Lys Leu Leu Gln Asn
                    790                      795                      800

CAA ATC CAG CAG CAG ACA TGG ACA GAT GAA GGC ACA CCA TCC ATG CGA          2507
Gln Ile Gln Gln Gln Thr Trp Thr Asp Glu Gly Thr Pro Ser Met Arg
                805                      810                      815

GAG CTT CGG TCA GCC TTG CTG GAA TTT GCC TGC GCC CAC AGC CTA GAG          2555
Glu Leu Arg Ser Ala Leu Leu Glu Phe Ala Cys Ala His Ser Leu Glu
            820                      825                      830

AAC TGT ACC ACT ATG GCC ACA AAG CTG TTT GAT GGT TGG ATG GCA TCA          2603
Asn Cys Thr Thr Met Ala Thr Lys Leu Phe Asp Gly Trp Met Ala Ser
835                      840                      845

AAT GGA ACT CAG AGC CTG CCG ACT GAC GTC ATG ACC ACT GTG TTC AAA          2651
Asn Gly Thr Gln Ser Leu Pro Thr Asp Val Met Thr Thr Val Phe Lys
850                      855                      860                      865

GTT GGA GCA AGA ACC GAG AAA GGC TGG TTG TTC CTC TTT AGC ATG TAC          2699
Val Gly Ala Arg Thr Glu Lys Gly Trp Leu Phe Leu Phe Ser Met Tyr
                    870                      875                      880

TCC TCC ATG GGC TCT GAA GCA GAG AAG GAT AAA ATA CTT GAA GCC CTG          2747
Ser Ser Met Gly Ser Glu Ala Glu Lys Asp Lys Ile Leu Glu Ala Leu
                885                      890                      895

GCC AGC TCA GCG GAT GCA CAT AAA CTT TAC TGG TTA ATG AAA AGT AGC          2795
Ala Ser Ser Ala Asp Ala His Lys Leu Tyr Trp Leu Met Lys Ser Ser
            900                      905                      910

CTT GAT GGT GAT ATC ATT CGG ACA CAG AAG TTG TCA CTT ATC ATT AGA          2843
Leu Asp Gly Asp Ile Ile Arg Thr Gln Lys Leu Ser Leu Ile Ile Arg
```

```
                915                 920                 925
ACA GTG GGC AGA CAG TTT CCT GGA CAT TTG CTG GCA TGG GAT TTT GTT        2891
Thr Val Gly Arg Gln Phe Pro Gly His Leu Leu Ala Trp Asp Phe Val
930                 935                 940                 945

AAG GAA AAC TGG AAT AAG CTT GTA CAT AAG TTC CAT CTG GGC TCC TAT        2939
Lys Glu Asn Trp Asn Lys Leu Val His Lys Phe His Leu Gly Ser Tyr
                950                 955                 960

ACC ATT CAA AGC ATT GTT GCT GGA TCT ACT CAC TTA TTT TCA ACG AAG        2987
Thr Ile Gln Ser Ile Val Ala Gly Ser Thr His Leu Phe Ser Thr Lys
                965                 970                 975

ACA CAT TTA TCT GAG GTC CAG GAA TTC TTC GAA AAT CAG TCA GAG GCA        3035
Thr His Leu Ser Glu Val Gln Glu Phe Phe Glu Asn Gln Ser Glu Ala
                980                 985                 990

ACC TTG CAG CTT CGG TGT GTT CAG GAG GCC TTC GAA GTG ATT GAG CTG        3083
Thr Leu Gln Leu Arg Cys Val Gln Glu Ala Phe Glu Val Ile Glu Leu
995                 1000                1005

AAT ATC CAG TGG ATG GCC AGG AAT CTG AAA ACT CTG ACA CTG TGG CTG        3131
Asn Ile Gln Trp Met Ala Arg Asn Leu Lys Thr Leu Thr Leu Trp Leu
1010                1015                1020                1025

TAGCCCTCAC AGCTGATCTT CCGGTGCCCA TGGCTCTGCT GCTTTTGCAA AGGTTGAGTG      3191

AAGGCCGGCC TGCTACTGAG TTGTTTGCAC TGTTAGGATC TAGTTAGCTC AGGGCCCAAT      3251

TGTATTTTTC ATATCTTTTC TGAAATGTCC TTAGGCGGTA GTTATTTATT ACAAAATTAT      3311

ATTCACCTGT ACGTCAACCA TCTACAATAA CAGTGAAGAC CTGCCCGCGC GGCCGCTCGA      3371

GCCCTATAGT GAGT                                                        3385

(2) INFORMATION FOR SEQ ID NO: 17:

(i) SEQUENCE CHARACTERISTICS:
        (A) LENGTH: 18 amino acids
        (B) TYPE: amino acid
        (D) TOPOLOGY: linear (ii) MOLECULE TYPE:
        (A) DESCRIPTION: peptide fragment of GTVap with homology
            to second repeat in GTVap (Seq ID No 18) and Glut4
            (Seq ID No. 19) and which is likely involved in retention
            and sorting to an insulin sensitive compartment.

(iii) HYPOTHETICAL: yes (ix) FEATURE:
        (A) NAME/KEY: Retention signal to insulin sensitive compartment
        (C) IDENTIFICATION METHOD: similarity to other sequence in
            GTVap and sequence in Glut4

(xi) SEQ (ix) FEATURE:
        (A) NAME/KEY: Retention signal to insulin sensitive
            compartment
        (C) IDENTIFICATION METHOD: similarity to other sequence
            in GTVap and sequence in Glut4

(xi) SEQUENCE DESCRIPTION: SEQ ID NO: 18:

His Glu Met Asp Glu Asp Glu Asp Tyr Glu Ser Ser Ala Lys Leu
                5                  10                  15

Leu (2) INFORMATION FOR SEQ ID NO: 19:

(i) SEQUENCE CHARACTERISTICS:
        (A) LENGTH: 21 amino acids
        (B) TYPE: amino acid
        (D) TOPOLOGY: linear (ii) MOLECULE TYPE:
        (A) DESCRIPTION: peptide fragment of Glut4 with homology to
            two repeats in GTVap (Seq ID Nos 17 and 18) and which
            is likely involved in retention and sorting to an insulin
            sensitive compartment.

(iii) HYPOTHETICAL: yes (ix) FEATURE:
        (A) NAME/KEY: Retention signal to insulin sensitive compartment
        (C) IDENTIFICATION METHOD: similarity to sequences in GTVap (xi) SEQUENCE DESCRIPTION: SEQ ID NO: 19:

Leu Leu Glu Gln Glu Val Lys Pro Ser Thr Glu Leu Glu Tyr Leu Gly
                5                  10                  15

Pro Asp Glu Asn Asp
        20

(2) INFORMATION FOR SEQ ID NO: 20:

(i) SEQUENCE CHARACTERISTICS:
        (A) LENGTH: 22 amino acids
        (B) TYPE: amino acid
        (D) TOPOLOGY: linear (ii) MOLECULE TYPE:
        (A) DESCRIPTION: peptide (iii) HYPOTHETICAL: yes (ix) FEATURE:
        (A) NAME/KEY: forward consensus of insulin sensitive
            retention sequence common to GTVap and GLUT4
        (D) OTHER INFORMATION: some amino acids may not be indicated;
            a total of 14-22 amino acids are possible (ix) FEATURE:
        (A) NAME/KEY: other
        (B) LOCATION: 1
        (D) OTHER INFORMATION: Pro, Glu, or Asp (ix) FEATURE:
        (A) NAME/KEY: other
        (B) LOCATION: 2
        (D) OTHER INFORMATION: any amino acid residue (ix) FEATURE:
        (A) NAME/KEY: other
        (B) LOCATION: 3, 4, and 5
        (D) OTHER INFORMATION: Pro, Glu, or Asp (ix) FEATURE:
        (A) NAME/KEY: other
        (B) LOCATION: 6, 7, and 8
        (D) OTHER INFORMATION: any amino acid residue

```
       (ix) FEATURE:
            (A) NAME/KEY: other
            (B) LOCATION: 11, 12, and 13
            (D) OTHER INFORMATION: any amino acid residue (ix) FEATURE:
            (A) NAME/KEY: other
            (B) LOCATION: 15
            (D) OTHER INFORMATION: any amino acid residue (ix) FEATURE:
            (A) NAME/KEY: other
            (B) LOCATION: 16
            (D) OTHER INFORMATION: Arg or Lys (ix) FEATURE:
            (A) NAME/KEY: other
            (B) LOCATION: 17, 18, 19, and 20
            (D) OTHER INFORMATION: any amino acid residue (xi) SEQUENCE DESCRIPTION: SEQ ID NO: 20:

Xaa Xaa Xaa Xaa Xaa Xaa Xaa Xaa Tyr Glu Xaa Xaa Xaa Ser Xaa
                 5                  10                  15

Xaa Xaa Xaa Xaa Xaa Leu Leu
            20

(2) INFORMATION FOR SEQ ID NO: 21:

(i) SEQUENCE CHARACTERISTICS:
         (A) LENGTH: 22 amino acids
         (B) TYPE: amino acid
         (D) TOPOLOGY: linear (ii) MOLECULE TYPE:
         (A) DESCRIPTION: peptide (iii) HYPOTHETICAL: yes (ix) FEATURE:
         (A) NAME/KEY: reverse consensus of insulin sensitive
             retention sequence common to GTVap and GLUT4
         (D) OTHER INFORMATION: some (D) OTHER INFORMATION:   any amino acid residue (ix) FEATURE:
            (A) NAME/KEY:  other
            (B) LOCATION:  22
            (D) OTHER INFORMATION:   Pro, Glu, or Asp (xi) SEQUENCE DESCRIPTION: SEQ ID NO: 21:

Leu Leu Xaa Xaa Xaa Xaa Xaa Ser Xaa Xaa Xaa Glu Tyr Xaa
            5                   10                  15

Xaa Xaa Xaa Xaa Xaa Xaa Xaa
            20

(2) INFORMATION FOR SEQ ID NO:22:

(i) SEQUENCE CHARACTERISTICS:
            (A) LENGTH: 1026 amino acids
            (B) TYPE: amino acid
            (C) STRANDEDNESS: single
            (D) TOPOLOGY: linear (ii) MOLECULE TYPE: protein (vi) ORIGINAL SOURCE:
            (A) ORGANISM: Rattus norvegicus
            (B) STRAIN: Sprague-Dawley
            (D) DEVELOPMENTAL STAGE: adult
            (F) TISSUE TYPE: skeletal muscle (vii) IMMEDIATE SOURCE:
            (A) LIBRARY: Clontech rat skeletal muscle cDNA library in
                lambda gt11 and mRNA isolated from rat skeletal muscle
            (B) CLONE: 5.3 (from lambda gt11 library), PCR product clones
                5, 334, and KC44.

(ix) FEATURE:
            (A) NAME/KEY: complete amino acid sequence for GTVap, short
                version
            (C) IDENTIFICATION METHOD: translation from cDNA (xi) SEQUENCE DESCRIPTION: SEQ ID NO: 22:

Met
                                                        1

Glu Thr Phe Thr Asn Asp Arg Leu Gln Leu Pro Arg Asn Met Ile Glu
        5                   10                  15

Asn Ser Met Phe Glu Glu Glu Pro Asp Val Val Asp Leu Ala Lys Glu
        20                  25                  30

Pro Cys Leu His Pro Leu Glu Pro Asp Glu Val Glu Tyr Glu Pro Arg
    35                  40                  45

Gly Ser Arg Leu Leu Val Arg Gly Leu Gly His Glu Met Asp Glu
50                  55                  60                  65

Asp Glu Glu Asp Tyr Glu Ser Ser Ala Lys Leu Leu Gly Met Ser Phe
                70                  75                  80

Met Asn Arg Ser Ser Gly Leu Arg Asn Ser Ala Thr Gly Tyr Arg Gln
                85                  90                  95

Ser Pro Asp Gly Thr Cys Ser Val Pro Ser Ala Arg Thr Leu Val Ile
            100                 105                 110

Cys Val Phe Val Ile Val Val Ala Val Ser Val Ile Met Val Ile Tyr
            115                 120                 125

Leu Leu Pro Arg Cys Thr Phe Thr Lys Glu Gly Cys His Lys Thr Asn
130                 135                 140                 145

Gln Ser Ala Glu Leu Ile Gln Pro Ile Ala Thr Asn Gly Lys Val Phe
                150                 155                 160

Pro Trp Ala Gln Ile Arg Leu Pro Thr Ala Ile Ile Pro Gln Arg Tyr
                165                 170                 175

```
Glu Leu Ser Leu His Pro Asn Leu Thr Ser Met Thr Phe Arg Gly Ser
        180                 185                 190

Val Thr Ile Ser Leu Gln Ala Leu Gln Asp Thr Arg Asp Ile Ile Leu
        195                 200             205

His Ser Thr Gly His Asn Ile Ser Ser Val Thr Phe Met Ser Ala Val
210                     215                 220                 225

Ser Ser Gln Glu Lys Gln Val Glu Ile Leu Glu Tyr Pro Tyr His Glu
                230                 235                 240

Gln Ile Ala Val Val Ala Pro Glu Ser Leu Leu Thr Gly His Asn Tyr
                245                 250                 255

Thr Leu Lys Ile Glu Tyr Ser Ala Asn Ile Ser Asn Ser Tyr Tyr Gly
        260                 265                 270

Phe Tyr Gly Ile Thr Tyr Thr Asp Lys Ser Asn Glu Lys Lys Asn Phe
275                 280                 285

Ala Ala Thr Gln Phe Glu Pro Leu Ala Ala Arg Ser Ala Phe Pro Cys
290                 295                 300                 305

Phe Asp Glu Pro Ala Phe Lys Ala Thr Phe Ile Ile Lys Ile Thr Arg
                310                 315                 320

Asp Glu His His Thr Ala Leu Ser Asn Met Pro Lys Lys Ser Ser Val
                325                 330                 335

Pro Thr Glu Glu Gly Leu Ile Gln Asp Glu Phe Ser Glu Ser Val Lys
        340                 345                 350

Met Ser Thr Tyr Leu Val Ala Phe Ile Val Gly Glu Met Arg Asn Leu
        355                 360                 365

Ser Gln Asp Val Asn Gly Thr Leu Val Ser Val Tyr Ala Val Pro Glu
370                 375                 380                 385

Lys Ile Asp Gln Val Tyr His Ala Leu Asp Thr Thr Val Lys Leu Leu
                390                 395                 400

Glu Phe Tyr Gln Asn Tyr Phe Glu Ile Gln Tyr Pro Leu Lys Lys Leu
                405                 410                 415

Asp Leu Val Ala Ile Pro Asp Phe Glu Ala Gly Ala Met Glu Asn Trp
        420                 425                 430

Gly Leu Leu Thr Phe Arg Glu Glu Thr Leu Leu Tyr Asp Asn Ala Thr
        435                 440                 445

Ser Ser Val Ala Asp Arg Lys Leu Val Thr Lys Ile Ile Ala His Glu
450                 455                 460                 465

Leu Ala His Gln Trp Phe Gly Asn Leu Val Thr Met Gln Trp Trp Asn
                470                 475                 480

Asp Leu Trp Leu Asn Glu Gly Phe Ala Thr Phe Met Glu Tyr Phe Ser
                485                 490                 495

Val Glu Lys Ile Phe Lys Glu Leu Asn Ser Tyr Glu Asp Phe Leu Asp
                500                 505                 510

Ala Arg Phe Lys Thr Met Arg Lys Asp Ser Leu Asn Ser Ser His Pro
515                 520                 525

Ile Ser Ser Ser Val Gln Ser Ser Glu Gln Ile Glu Glu Met Phe Asp
530                 535                 540                 545

Ser Leu Ser Tyr Phe Lys Gln Gly Ala Ser Leu Leu Met Leu Leu Lys
                550                 555                 560

Ser Tyr Leu Ser Glu Asp Val Phe Gln His Ala Ile Ile Leu Tyr Leu
                565                 570                 575

His Asn His Ser Tyr Ala Ala Ile Gln Ser Asp Asp Leu Trp Asp Ser
                580                 585                 590

Phe Asn Glu Val Thr Gly Lys Thr Leu Asp Val Lys Lys Met Met Lys
595                 600                 605
```

```
Thr Trp Thr Leu Gln Lys Gly Phe Pro Leu Val Thr Val Gln Arg Lys
610                 615                 620                 625

Gly Thr Glu Leu Leu Gln Gln Glu Arg Phe Phe Pro Ser Met Gln
            630                 635                 640

Pro Glu Ile Gln Asp Ser Asp Thr Ser His Leu Trp His Ile Pro Ile
            645                 650                 655

Ser Tyr Val Thr Asp Gly Arg Asn Tyr Ser Glu Tyr Arg Ser Val Ser
            660                 665                 670

Leu Leu Asp Lys Lys Ser Asp Val Ile Asn Leu Thr Glu Gln Val Gln
            675                 680                 685

Trp Val Lys Val Asn Thr Asn Met Thr Gly Tyr Tyr Ile Val His Tyr
690                 695                 700                 705

Ala His Asp Gly Trp Ala Ala Leu Ile Asn Gln Leu Lys Arg Asn Pro
                710                 715                 720

Tyr Val Leu Ser Asp Lys Asp Arg Ala Asn Leu Ile Asn Asn Ile Phe
                725                 730                 735

Glu Leu Ala Gly Leu Gly Lys Val Pro Leu Gln Met Ala Phe Asp Leu
                740                 745                 750

Ile Asp Tyr Leu Arg Asn Glu Thr His Thr Ala Pro Ile Thr Glu Ala
755                 760                 765

Leu Phe Gln Thr Asp Leu Ile Tyr Asn Leu Leu Glu Lys Leu Gly His
770                 775                 780                 785

Met Asp Leu Ser Ser Arg Leu Val Thr Arg Val His Lys Leu Leu Gln
                790                 795                 800

Asn Gln Ile Gln Gln Thr Trp Thr Asp Glu Gly Thr Pro Ser Met
            805                 810                 815

Arg Glu Leu Arg Ser Ala Leu Leu Glu Phe Ala Cys Ala His Ser Leu
            820                 825                 830

Glu Asn Cys Thr Thr Met Ala Thr Lys Leu Phe Asp Gly Trp Met Ala
            835                 840                 845

Ser Asn Gly Thr Gln Ser Leu Pro Thr Asp Val Met Thr Thr Val Phe
850                 855                 860                 865

Lys Val Gly Ala Arg Thr Glu Lys Gly Trp Leu Phe Leu Phe Ser Met
                870                 875                 880

Tyr Ser Ser Met Gly Ser Glu Ala Glu Lys Asp Lys Ile Leu Glu Ala
                885                 890                 895

Leu Ala Ser Ser Ala Asp Ala His Lys Leu Tyr Trp Leu Met Lys Ser
                900                 905                 910

Ser Leu Asp Gly Asp Ile Ile Arg Thr Gln Lys Leu Ser Leu Ile Ile
            915                 920                 925

Arg Thr Val Gly Arg Gln Phe Pro Gly His Leu Leu Ala Trp Asp Phe
930                 935                 940                 945

Val Lys Glu Asn Trp Asn Lys Leu Val Lys Phe His Leu Gly Ser
                950                 955                 960

Tyr Thr Ile Gln Ser Ile Val Ala Gly Ser Thr His Leu Phe Ser Thr
                965                 970                 975

Lys Thr His Leu Ser Glu Val Gln Glu Phe Phe Glu Asn Gln Ser Glu
            980                 985                 990

Ala Thr Leu Gln Leu Arg Cys Val Gln Glu Ala Phe Glu Val Ile Glu
            995                 1000                1005

Leu Asn Ile Gln Trp Met Ala Arg Asn Leu Lys Thr Leu Thr Leu Trp
1010                1015                1020                1025

Leu
```

(2) INFORMATION FOR SEQ ID NO: 23:

(i) SEQUENCE CHARACTERISTICS:
        (A) LENGTH: 1025 amino acids
        (B) TYPE: amino acid
        (C) STRANDEDNESS: single
        (D) TOPOLOGY: linear (ii) MOLECULE TYPE: protein;

(vi) ORIGINAL SOURCE:
        (A) ORGANISM: Rattus norvegicus
        (B) STRAIN: Sprague-Dawley
        (D) DEVELOPMENTAL STAGE: adult
        (F) TISSUE TYPE: skeletal muscle (vii) IMMEDIATE SOURCE:
        (A) LIBRARY: Clontech rat skeletal muscle cDNA library in
            lambda gt11 and mRNA isolated from rat skeletal muscle
        (B) CLONE: 12.1 (from lambda gt11 library), PCR product
            clones 5, 334, and KC44.

(ix) FEATURE:
        (A) NAME/KEY: complete amino acid sequence for GTVap, long
            version
        (C) IDENTIFICATION METHOD: translation from cDNA (xi) SEQUENCE DESCRIPTION: SEQ ID NO: 23:

```
                                                            Met
                                                             1

Glu Thr Phe Thr Asn Asp Arg Leu Gln Leu Pro Arg Asn Met Ile Glu
          5                  10                  15

Asn Ser Met Phe Glu Glu Pro Asp Val Val Asp Leu Ala Lys Glu
         20                  25                  30

Pro Cys Leu His Pro Leu Glu Pro Asp Glu Val Glu Tyr Glu Pro Arg
 35                  40                  45

Gly Ser Arg Leu Leu Val Arg Gly Leu Gly Glu His Glu Met Asp Glu
 50                  55                  60                  65

Asp Glu Glu Asp Tyr Glu Ser Ser Ala Lys Leu Leu Gly Met Ser Phe
                 70                  75                  80

Met Asn Arg Ser Ser Gly Leu Arg Asn Ser Ala Thr Gly Tyr Arg Gln
                 85                  90                  95

Ser Pro Asp Gly Thr Cys Ser Val Pro Ser Ala Arg Thr Leu Val Ile
                100                 105                 110

Cys Val Phe Val Ile Val Val Ala Val Ser Val Ile Met Val Ile Tyr
                115                 120                 125

Leu Leu Pro Arg Cys Thr Phe Thr Lys Glu Gly Cys His Lys Thr Asn
130                 135                 140                 145

Gln Ser Ala Glu Leu Ile Gln Pro Ile Ala Thr Asn Gly Lys Val Phe
                150                 155                 160

Pro Trp Ala Gln Ile Arg Leu Pro Thr Ala Ile Ile Pro Gln Arg Tyr
                165                 170                 175

Glu Leu Ser Leu His Pro Asn Leu Thr Ser Met Thr Phe Arg Gly Ser
                180                 185                 190

Val Thr Ile Ser Leu Gln Ala Leu Gln Asp Thr Arg Asp Ile Ile Leu
         195                 200                 205

His Ser Thr Gly His Asn Ile Ser Ser Val Thr Phe Met Ser Ala Val
210                 215                 220                 225

Ser Ser Gln Glu Lys Gln Val Glu Ile Leu Glu Tyr Pro Tyr His Glu
                230                 235                 240

Gln Ile Ala Val Val Ala Pro Glu Ser Leu Leu Thr Gly His Asn Tyr
                245                 250                 255
```

-continued

```
Thr Leu Lys Ile Glu Tyr Ser Ala Asn Ile Ser Asn Ser Tyr Tyr Gly
        260                 265                 270

Phe Tyr Gly Ile Thr Tyr Thr Asp Lys Ser Asn Glu Lys Lys Asn Phe
        275                 280                 285

Ala Ala Thr Gln Phe Glu Pro Leu Ala Ala Arg Ser Ala Phe Pro Cys
290                 295                 300                 305

Phe Asp Glu Pro Ala Phe Lys Ala Thr Phe Ile Ile Lys Ile Thr Arg
                310                 315                 320

Asp Glu His His Thr Ala Leu Ser Asn Met Pro Lys Lys Ser Ser Val
            325                 330                 335

Pro Thr Glu Glu Gly Leu Ile Gln Asp Glu Phe Ser Glu Ser Val Lys
            340                 345                 350

Met Ser Thr Tyr Leu Val Ala Phe Ile Val Gly Glu Met Arg Asn Leu
        355                 360                 365

Ser Gln Asp Val Asn Gly Thr Leu Val Ser Val Tyr Ala Val Pro Glu
370                 375                 380                 385

Lys Ile Asp Gln Val Tyr His Ala Leu Asp Thr Thr Val Lys Leu Leu
                390                 395                 400

Glu Phe Tyr Gln Asn Tyr Phe Glu Ile Gln Tyr Pro Leu Lys Lys Leu
            405                 410                 415

Asp Leu Val Ala Ile Pro Asp Phe Glu Ala Gly Ala Met Glu Asn Trp
        420                 425                 430

Gly Leu Leu Thr Phe Arg Glu Glu Thr Leu Leu Tyr Asp Asn Ala Thr
    435                 440                 445

Ser Ser Val Ala Asp Arg Lys Leu Val Thr Lys Ile Ile Ala His Glu
450                 455                 460                 465

Leu Ala His Gln Trp Phe Gly Asn Leu Val Thr Met Gln Trp Trp Asn
                470                 475                 480

Asp Leu Trp Leu Asn Glu Gly Phe Ala Thr Phe Met Glu Tyr Phe Ser
            485                 490                 495

Val Glu Lys Ile Phe Lys Glu Leu Asn Ser Tyr Glu Asp Phe Leu Asp
        500                 505                 510

Ala Arg Phe Lys Thr Met Arg Lys Asp Ser Leu Asn Ser Ser His Pro
    515                 520                 525

Ile Ser Ser Ser Val Gln Ser Ser Glu Gln Ile Glu Glu Met Phe Asp
530                 535                 540                 545

Ser Leu Ser Tyr Phe Lys Gly Ala Ser Leu Leu Leu Met Leu Lys Ser
                550                 555                 560

Tyr Leu Ser Glu Asp Val Phe Gln His Ala Ile Ile Leu Tyr Leu His
            565                 570                 575

Asn His Ser Tyr Ala Ala Ile Gln Ser Asp Asp Leu Trp Asp Ser Phe
        580                 585                 590

Asn Glu Val Thr Gly Lys Thr Leu Asp Val Lys Lys Met Met Lys Thr
    595                 600                 605

Trp Thr Leu Gln Lys Gly Phe Pro Leu Val Thr Val Gln Arg Lys Gly
610                 615                 620                 625

Thr Glu Leu Leu Leu Gln Gln Glu Arg Phe Phe Pro Ser Met Gln Pro
                630                 635                 640

Glu Ile Gln Asp Ser Asp Thr Ser His Leu Trp His Ile Pro Ile Ser
            645                 650                 655

Tyr Val Thr Asp Gly Arg Asn Tyr Ser Glu Tyr Arg Ser Val Ser Leu
        660                 665                 670

Leu Asp Lys Lys Ser Asp Val Ile Asn Leu Thr Glu Gln Val Gln Trp
```

-continued

```
              675                 680                 685
Val Lys Val Asn Thr Asn Met Thr Gly Tyr Tyr Ile Val His Tyr Ala
690                 695                 700                 705

His Asp Gly Trp Ala Ala Leu Ile Asn Gln Leu Lys Arg Asn Pro Tyr
                710                 715                 720

Val Leu Ser Asp Lys Asp Arg Ala Asn Leu Ile Asn Asn Ile Phe Glu
                725                 730                 735

Leu Ala Gly Leu Gly Lys Val Pro Leu Gln Met Ala Phe Asp Leu Ile
                740                 745                 750

Asp Tyr Leu Arg Asn Glu Thr His Thr Ala Pro Ile Thr Glu Ala Leu
        755                 760                 765

Phe Gln Thr Asp Leu Ile Tyr Asn Leu Leu Glu Lys Leu Gly His Met
770                 775                 780                 785

Asp Leu Ser Ser Arg Leu Val Thr Arg Val His Lys Leu Leu Gln Asn
                790                 795                 800

Gln Ile Gln Gln Gln Thr Trp Thr Asp Glu Gly Thr Pro Ser Met Arg
                805                 810                 815

Glu Leu Arg Ser Ala Leu Leu Glu Phe Ala Cys Ala His Ser Leu Glu
                820                 825                 830

Asn Cys Thr Thr Met Ala Thr Lys Leu Phe Asp Gly Trp Met Ala Ser
        835                 840                 845

Asn Gly Thr Gln Ser Leu Pro Thr Asp Val Met Thr Thr Val Phe Lys
850                 855                 860                 865

Val Gly Ala Arg Thr Glu Lys Gly Trp Leu Phe Leu Phe Ser Met Tyr
                870                 875                 880

Ser Ser Met Gly Ser Glu Ala Glu Lys Asp Lys Ile Leu Glu Ala Leu
                885                 890                 895

Ala Ser Ser Ala Asp Ala His Lys Leu Tyr Trp Leu Met Lys Ser Ser
        900                 905                 910

Leu Asp Gly Asp Ile Ile Arg Thr Gln Lys Leu Ser Leu Ile Ile Arg
        915                 920                 925

Thr Val Gly Arg Gln Phe Pro Gly His Leu Leu Ala Trp Asp Phe Val
930                 935                 940                 945

Lys Glu Asn Trp Asn Lys Leu Val His Lys Phe His Leu Gly Ser Tyr
                950                 955                 960

Thr Ile Gln Ser Ile Val Ala Gly Ser Thr His Leu Phe Ser Thr Lys
                965                 970                 975

Thr His Leu Ser Glu Val Gln Glu Phe Phe Glu Asn Gln Ser Glu Ala
        980                 985                 990

Thr Leu Gln Leu Arg Cys Val Gln Glu Ala Phe Glu Val Ile Glu Leu
        995                 1000                1005

Asn Ile Gln Trp Met Ala Arg Asn Leu Lys Thr Leu Thr Leu Trp Leu
1010                1015                1020                1025
```

GLUCOSE TRANSPORTER VESICLE AMINOPEPTIDASE

This application is a continuation-in-part of application Ser. No. 08/309,232 filed on Sep. 20, 1994, now abandoned.

This application relates to biochemistry of diabetes, and more particularly, to an aminopeptidase which is involved in insulin regulation.

BACKGROUND

Adipocytes and myocytes contain intracellular GLUT4-containing vesicles which fuse to the plasma membrane upon insulin stimulation. The resulting increase in plasma membrane GLUT4 is responsible for the 10 to 20-fold increase in glucose transport in the insulin-stimulated state. GLUT4-containing vesicle movement from the cytoplasm to fusion with the plasma membrane, a process termed translocation, is believed to be abnormal in both insulin resistance and non-insulin dependent diabetes mellitus (NIDDM) (B. Kahn, J. Clin. Invest., 89, 1367–1374, (1992)).

The normal molecular mechanisms of insulin-stimulated translocation of GLUT4-containing vesicles to the plasma membrane and the concomitant increase in glucose uptake by the affected cells are still largely unknown. Proposed mechanisms include both GLUT4-containing vesicle docking and fusion with the plasma membrane.

The GLUT4-containing vesicles are only a minor fraction of the total intracellular vesicle population within adipocytes (James et al, J. Biol. Chem., 262, 11817–11824, (1987)). These GLUT4 vesicles can be isolated from the low density microsomal fraction using immunoaffinity methods with antibodies to the cytoplasmic-oriented C-terminus of GLUT4 (James, et al, J. Biol. Chem., 262, 11817–11824, (1987); Thoidis, et al, J. Biol. Chem., 268, 11691–11696, (1993)). GLUT4-enriched vesicles have been shown to contain several synaptic vesicle-like proteins including vesicle associated membrane protein (VAMP) (Cain et al, J. Biol. Chem., 267, 11681–11684, (1992)), secretory carrier associated membrane protein (SCAMP) (Laurie et al, J. Biol. Chem., 268, 19110–19117, (1993)), and certain ras analog proteins originally identified in brain (Rab proteins) (Cormont, et al, J. Biol. Chem., 268, 19491–19497, (1993)).

Presently the pharmacologic therapy for NIDDM may not target the insulin resistance which is the key pathophysiological abnormality of the disease. The existing therapies are 1) diet and exercise; 2) sulfonylureas, which stimulate insulin secretion; 3) α-glucosidase inhibitors, which inhibit the enzymatic digestion of complex carbohydrates and thereby slow the postprandial absorption of glucose; 4) metformin, whose mechanism likely includes improvement of hepatic insulin sensitivity, and 5) insulin injections.

A therapeutic agent which targets insulin resistance and improves insulin sensitivity would have significant advantages over the therapies listed above. Such a therapeutic agent is the subject of the present invention. It is an objective of this invention to increase insulin sensitivity by modulating the aminopeptidase associated with GLUT4 vesicles.

SUMMARY

The present invention relates to a novel aminopeptidase, herein designated GTVap, which is a component of GLUT4-containing vesicles and is involved in the insulin-signalling pathway. It also relates to the use of therapeutic modulators of this protein to treat diabetes. Additional aspects of the invention will be discussed below.

Down-regulation of peptide signalling molecules is important to maintain normal homeostasis. More particularly, down-regulation or removal of active insulin is important for prevention of hyperinsulinemia with resulting hypoglycemia in nondiabetic individuals. Current dogma is that all circulating insulin is degraded after binding to the insulin receptor, internalization, and eventual intracellular proteolysis by a previously characterized insulin degrading enzyme (IDE).

Data presented herein indicate that an additional mechanism for insulin degradation exists, namely, that adipocyte cell surface GTVap removes the N-terminal amino acids from the insulin molecule, altering its physiological activity. Although this may be a normal mechanism of insulin processing, the increased level of enzyme present in obese individuals or in conditions of increased enzyme activity leads to conditions in which plasma insulin has been partially inactivated. This explains the association of obesity with insulin resistance and NIDDM.

Another indication that GTVap may be important in the insulin signalling pathway is the fact that GTVap is found primarily in insulin-sensitive tissues which also contain the GLUT4 protein.

It is known that obesity is associated with a variety of clinical manifestations, as well as with increased body fat with a concomitant increase of GTVap. The increased body fat and GTVap may result in inappropriate inactivation or activation of other important circulating polypeptides besides insulin. Accordingly, pharmacological and genetic manipulation of GTVap constitutes a new therapeutic target for amelioration of insulin resistance, NIDDM, and obesity.

The present invention relates to a protein which is a component of GLUT4-containing vesicles in the natural state. This protein has aminopeptidase activity; a molecular weight of approximately 165 kD, 155 kD, or 120 kD depending upon its degree of glycosylation, and approximately 110 kD in its deglycosylated form. It includes the amino acid sequences Phe-Ala-Ala-Thr-Gln-Phe-Glu-Pro-Leu-Ala-Ala (SEQ ID NO: 1) and Ile-Leu-Gln-Asn-Gln-Ile-Gln-Gln-Gln-Thr-Arg-Thr-Asp-Glu-Gly-Xaa-Pro-Xaa-Met (SEQ ID NO: 2), and reacts with antibodies produced against the peptide identified as (SEQ ID NO: 1). It is encoded by the cDNA which encodes the full length sequence of GTVap (SEQ ID NOs: 15 and 16) and its amino acid sequence is essentially identical to that predicted for GTVap (SEQ ID NOs:15 and 16). The present invention also relates to muteins of this protein.

The present invention also relates to the cDNA encoding the full length sequence of GTVap and the predicted protein sequence (SEQ. ID NOs: 15 and 16).

The invention further relates to a method of treating syndromes of insulin resistance, comprising administering to a subject exhibiting a syndrome of insulin resistance an effective amount of a modulator of GTVap in a pharmaceutically acceptable carrier.

Other aspects of the invention will be discussed in the detailed description below.

DESCRIPTION OF THE DRAWING

The invention will be more completely understood from a consideration of the following detailed description and glossary of terms, taken in conjunction with the drawing, in which:

FIG. 20 shows the cDNA sequences of GTVap and the protein sequences predicted from those cDNAs (SEQ. ID. Numbers 15 and 16).

FIG. 21 shows the GTVap and GLUT4 retention and sorting consensus sequence (SEQ ID NO: 20), the reverse retention and sorting consensus sequence (SEQ ID NO: 21), and the respective segments of the GTVap (in N to C orientation; (SEQ ID NOs 17 and 18)) and GLUT4 (in C to N orientation; (SEQ ID NO. 19)) from which they were derived. The asterisk indicates the sequence is written in the nonconventional C to N direction. Xaa stands for any amino acid; $X^1$aa stands for Pro, Glu, or Asp; and $X^2$aa stands for Arg or Lys.

DETAILED DESCRIPTION

Figure 1:
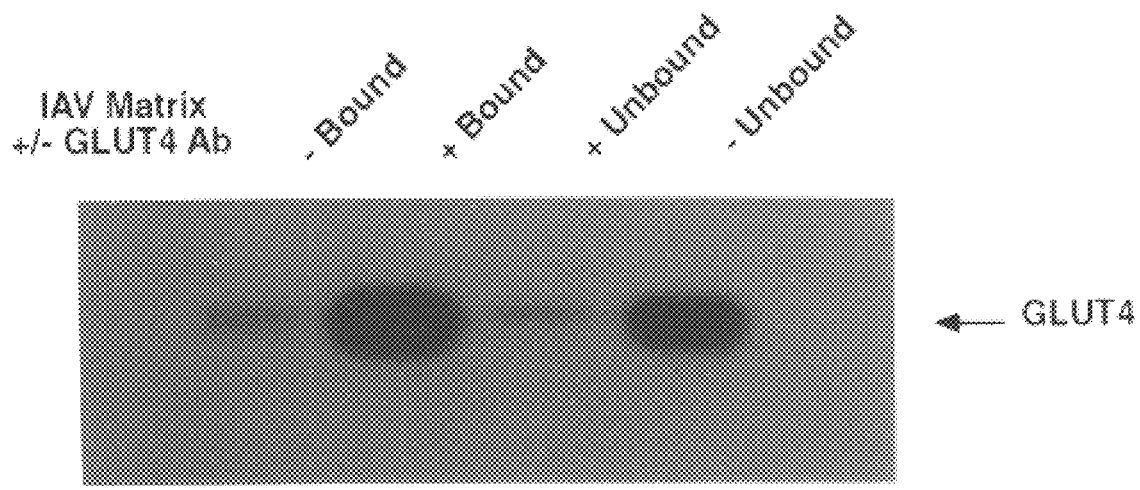
FIG. 1 is a Western blot showing the immunoaffinity purification of GLUT4 vesicles.

GLUT4-containing LDM vesicles from rat adipocytes have been purified by an immunoaffinity procedure and their protein composition has been compared to LDM vesicles lacking GLUT4. The hypothesis has been that the GLUT4 vesicle proteins are involved in the insulin-induced translocation of the vesicles, which includes movement from their resident intracellular compartment, docking with and fusion with the plasma membrane, and re-uptake or endocytosis from the plasma membrane upon termination of the insulin signal. The present purification strategy resulted in the identification of several unique proteins with molecular weights in the vicinity of 160 kD.

Two of the proteins identified as being unique to GLUT4-containing vesicles have molecular weights of approximately 165 kD and 155 kD, respectively. Initial attempts at N-terminal sequencing indicated that the N-terminus of each was blocked. Digestion of both the 165 kD and 155 kD proteins followed by microbore HPLC separation of the peptide fragments indicated that these proteins are closely related, as the HPLC-UV profiles of the digests are quite similar. One peptide sequence had 100% homology to a previously published 15 amino acid peptide claimed to be a fragment of a pregnancy-related plasma aminopeptidase. None of the remaining peptide sequences have any homology to the placental or any other known aminopeptidase.

Experiments with a variety of synthetic and natural aminopeptidase substrates have shown that the 165 kD, 155 kD, and 120 kD proteins within the adipocyte are aminopeptidases and are glycosylated since they bind to wheat germ lectin affinity resins. The 165 kD and 155 kD materials can be deglycosylated using N-glycosidase F and result in a protein of 110 kD. The 120 kD material is related to the 165 kD and 155 kD aminopeptidases since antibodies reactive with the 165 kD and 155 kD forms also react with the 120 kD aminopeptidase. In the text below, each aminopeptidase from the GLUT4-containing vesicles will be referred to as a Glucose Transporter Vesicle aminopeptidase (GTVap), with the molecular weight in kD being appended to the designation.

Although one peptide sequence of GTVap 165 kD had 100% homology to a known pregnancy-related aminopeptidase of placental origin, the two aminopeptidases have significantly different properties and are presumably members of a larger family of aminopeptidases. The GTVap enzyme activity and immunoreactivity have also been found in rat muscle, human fat, and the adipocyte cell line 3T3-L1. High levels of immunoreactivity can also be found in spleen with lower amounts in other tissues.

Regarding the isolated and purified aminopeptidase which is a component of GLUT4-containing vesicles in the natural state, the aminopeptidase activity, molecular weight, certain amino acid sequences, and its reactivity with antibodies produced against the peptide identified as [SEQ ID NO: 1] have been summarized above. This protein is useful for identification of modulators which may have utility in the treatment of diabetes. The protein is further characterized in that it possesses optimal activity at neutral pH; its relative activity toward synthetic amino acid p-nitroanilide substrates is: leucine>>proline, alanine>valine, glycine; its relative activity toward synthetic amino acid napthylamide substrates is leucine>lysine>arginine>methionine>alanine>phenylalanine; its activity is modulated by divalent ions of Co, Zn, Mg, Mn, and Ca; the minimum temperature of inactivation is between 40° C. and 50° C.; its activity is stabilized by ions of Ca; its activity is reduced by phenanthroline, dipyridyl, leuthiol, amastatin, actinonin, and bestatin; and it has at least three glycosylated forms having molecular weights of approximately 165 kD, 155 kD, and 120 kD, respectively. These characteristics are developed in the experimental section below.

In a second aspect, the invention relates to a method for purifying GTVap and separating glycosylated species thereof, comprising the following steps: (a) extracting the GTVap from at least one source; (b) contacting the resulting GTVap extract with lectin affinity resin to absorb glycosylated GTVap; (c) eluting the glycosylated GTVap from the lectin affinity resin; (d) contacting the eluate from the lectin affinity resin with a chelation chromatography resin which includes a metal ion which interacts simultaneously with the resin and with GTVap; (e) collecting unbound material from the chelation chromatography resin; (f) eluting bound material from the chelation chromatography resin; (g) separately contacting the unbound and the eluted GTVap-containing fractions from the chelation chromatography resin with anion exchange resin; (h) eluting bound GTVap species from the anion exchange resin; and (i) detecting separated GTVap species from the anion exchange resin.

In the claimed method of purifying GTVap and separating glycosylated species thereof, the step of extracting GTVap from at least one biological source of origin is preferably carried out using a mixture of at least one metal ion stabilizer and a detergent. As shown in the experimental section below, the activity of the enzyme decreases with time and in the absence of stabilizing agents. It has now been found that calcium ion, preferably at a concentration of 2 mM, serves as one of a potentially larger number of metal ions which serve to stabilize the activity of the protein. A variety of different detergents may be employed, non-ionic detergents such as Triton X-100 being preferred. The step of contacting the GTVap extract with lectin affinity resin to absorb glycosylated GTVap is carried out using any of a number of commercially available lectins known to those skilled in the art for their ability to absorb glycoproteins. These include Concanavalin A, wheat germ, Helix, Lens culinaris, and Limulus lectins. Although wheat germ lectin was employed in this invention, others could have been used. Elution of the glycosylated GTVap from the lectin affinity resin is accomplished using any of a variety of procedures to disrupt the lectin-carbohydrate binding. Examples include use of a competing carbohydrate ligand, and varying the conditions of pH. The chelation chromatography step is conducted by contacting the eluate from the lectin affinity resin with a chelation chromatography resin comprising a metal ion which interacts simultaneously with the resin and with GTVap. There are a number of suitable commercially available chelation chromatography resins. These resins are typically loaded with metal ions which can interact with the protein or glycoprotein being purified, and with the resin. In the present invention, it is preferable to use zinc as the metal ion, as this can interact with the GTVap and with the iminodiacetate resin used. Elution of bound material from the chelation chromatography resin typically is accomplished by adding a chelating agent such as EDTA or by changing the pH. Preferably, conditions which do not alter the intrinsic activity of the enzyme are employed. The step of separately contacting the unbound and the eluted GTVap-containing fractions from the chelation chromatography resin with anion exchange resin can be accomplished using a variety of different supports containing functionally active ligands known to those skilled in the art. The process of this invention preferably uses a resin such as Resource Q which has a high resolution capacity and excellent flow rates when run using fast liquid chromatographic procedures. Elution of bound GTVap species from the anion exchange resin is preferably accomplished by use of an increasing salt gradient, or alternatively, by changing the buffer pH. The step of detecting separated GTVap species from the anion exchange resin is carried out by measuring enzyme activity. The GTVap activity can be detected using any of a number of substrates, including the amino acid p-nitroanilide or β-napthylamide derivatives as well as native protein substrates such as insulin. Other substrates could also be employed. This procedure is useful for purification of the enzyme, which in turn permits its further characterization, as well as preparation of antibodies to the enzyme, and identification of modulators of the enzyme's activity.

In a third aspect, the invention relates to a method for identifying modulators of GTVap activity, comprising the following steps: (a) providing GTVap or GTVap-containing material having an assayable amount of enzymatic activity; (b) incubating the GTVap or GTVap-containing material with a test substance to be assayed for ability to modulate GTVap activity; (c) adding a GTVap substrate; (d) monitoring GTVap activity as a function of time; and (e) determining the modulatory effect of the test substance on GTVap.

Regarding the method for identifying modulators of GTVap activity, the step of providing GTVap or GTVap-containing material having an assayable amount of enzymatic activity involves the use of biological tissues including but not limited to adipose tissue, skeletal muscle tissue, cardiac muscle, spleen tissue, cell lines derived from these materials, or recombinant sources made using methods known to those skilled in the art. Such tissue would typically be of human or rodent origin, though GTVap also can be derived from other species. Preferably, the human source of the enzyme is used.

A recombinant source would be, for instance, insertion of the gene encoding GTVap into a prokaryotic or eukaryotic cell line capable of transcribing the inserted gene, resulting in the expression of an enzymatically active GTVap molecule. Such procedures are understood by those skilled in the art. In the step of incubating the GTVap or GTVap-containing material with a test substance to be assayed for ability to modulate GTVap activity the possible test substances would include analogs of known aminopeptidase inhibitors, and synthetic and naturally occurring test substances with no known previous activity. The step of adding a GTVap substrate would typically involve use of a synthetic aminopeptidase substrate such as leucine p-nitroanilide, or a synthetic or naturally occurring polypeptide substrate in which the N-terminal amino acids could be removed by the particular enzyme. Two examples of suitable polypeptides are insulin and synthetic insulin. The step of monitoring GTVap activity as a function of time is generally carried out by monitoring disappearance of substrate or appearance of the product of enzymatic activity upon the substrate. This is typically accomplished by spectroscopic or chromatographic means, though a wide variety of other techniques have been employed for the purpose, depending on the individual cases. The step of determining the modulatory effect of said test substance on GTVap is carried out by comparing the rate of cleavage of the GTVap substrate in the presence and absence of the test substance.

In a fourth aspect the invention relates to an antibody specific for GTVap, produced using substantially pure GTVap or a fragment thereof.

The antibody specific for GTVap may be produced as follows. Polyclonal antisera is produced against GTVap by injecting intact GTVap or fragments thereof into any of a variety of host animals such as rabbits, mice, goats, and sheep. The antibodies produced in such host animals will be polyclonal in nature, in which case the specific antibodies can be partially purified by procedures known to those skilled in the art. Furthermore, monoclonal antibodies may be produced by fusion of immunocompetent spleen cells with myeloma cells to yield a hybrid cell line that produces essentially monoclonal immunoglobulin. Under the current state of that art, such animals include mice and rats. The antibodies would find use in the detection and quantitation of GTVap in biological materials. Additionally, such antibodies could be used for the purification of GTVap using immunoaffinity methods known to those skilled in the art.

In a fifth aspect the invention relates to a method for preparing proteins and peptides truncated at the aminoterminus, comprising the step of incubating a protein or peptide with GTVap.

Regarding the method for preparing truncated proteins and peptides, the process is carried out by incubating the subject protein under conditions which enhance GTVap activity, i.e., under conditions of neutral pH and in the presence of ions which increase or stabilize the activity of the GTVap. The truncated product is isolated from the reaction by any suitable separating procedure. The material being truncated is insulin or any polypeptide with an amino terminus capable of being cleaved by GTVap. The method of preparing truncated peptides and proteins is used to derive new pharmacologically active polypeptides.

In a sixth aspect the invention relates to a method for determining GTVap in biological material, comprising the following steps: (a) preparing a specimen of biological material to optimally expose immunoreactive epitopes; (b) incubating this specimen or an extract thereof with GTVap specific antibody; (c) removing unbound antibodies from the specimen; and (d) quantifying antibodies bound to GTVap in the specimen.

Regarding the method for determining GTVap in biological material, the step of preparing a specimen of biological material to optimally expose immunoreactive epitopes is carried out by washing with buffer or treating under more chaotropic conditions which will expose epitopes that are buried in the native conformation of the protein. Such chaotropes would include acetone- or alcohol-containing solutions, SDS, and other denaturants with similar properties. These preparative methods allow detection of either native or denatured GTVap. The step of incubating the specimen or an extract thereof with GTVap specific antibody is carried out in the normal manner, and preferably employs the GTVap1 antibody of the present invention. The GTVap-specific antibody can be labeled directly, with fluorophors, biotin, a radioisotope, or an enzyme such as alkaline phosphatase or horseradish peroxidase. The quantification of antibodies bound to GTVap in the specimen is carried out by identifying the aforementioned labels. Alternatively, bound antibody can be detected using secondary antibodies which are themselves labeled and which will bind specifically to the primary antibody, which is in turn bound to GTVap.

In an seventh aspect the invention relates to an oligonucleotide probe specific for a nucleic acid sequence encoding a segment of GTVap.

Examples of oligonucleotide probes specific for a nucleic acid sequence encoding a segment of GTVap are the following materials, which are shown below in conjunction with the amino acid sequences identified in GTVap, referred to in Table I:

```
Peptide:
    Phe-Ala-Ala-Thr-Gln-Phe-Glu-Pro-Leu-Ala-Ala
    (SEQ ID NO: 1)

Corresponding "Sense" oligonucleotide:
 5' TTY GCN GCN ACN CAR TTY GAR CCN YTN GCN GCN 3'
 (SEQ ID NO: 3)

Corresponding "Antisense" oligonucleotide:
 5' NGC NGC NAR NGG YTC RAA YTG NGT NGC NGC RAA 3'
 (SEQ ID NO: 4)

Peptide:
    Ile-Leu-Gln-Asn-Gln-Ile-Gln-Gln-Gln-Thr-
    Arg-Thr-Asp-Glu-Gly   (SEQ ID NO: 5)

Corresponding "Sense" oligonucleotide:
 5' ATH YTN CAR AAY CAR ATH CAR CAR CAR ACN
    MGN ACN GAY GAR GGN   3' (SEQ ID NO: 6)

Corresponding "Antisense" oligonucleotide:
 5' NCC YTC RTC NGT NCK NGT YTG YTG YTG DAT
    YTG RTT YTG NAR DAT   3' (SEQ ID NO: 7)
```

In the above sense and antisense oligonucleotides the standard single letter designations are used for the individual bases, and the letter N designates degenerate positions. N is A, T, C, G, or I (inosine); R is A or G; Y is C or T; M is A or C; K is G or T; S is C or G; W is A or T; H is A, C, or T; B is C, G, or T; V is A, C, or G; and D is A, G, or T. Fragments of the above oligonucleotides and additional nucleotide replacements known to those skilled in the art constitute further examples. These oligonucleotides can be used in determining nucleic acids encoding GTVap in biological sources.

In an eighth aspect the invention relates to a method for determining a nucleic acid sequence encoding a segment of GTVap in a biological specimen, comprising the following steps: (a) preparing a biological specimen for analysis of nucleic acid material; (b) incubating nucleic acid material of this biological specimen with an oligonucleotide or nucleic acid probe specific for a nucleic acid sequence encoding a segment of GTVap; (c) removing unbound oligonucleotide or nucleic acid probe from the nucleic acid material; and (d) determining oligonucleotide probe bound to a nucleic acid sequence encoding a segment of GTVap.

Regarding the method for determining a nucleic acid sequence encoding a segment of GTVap in a biological specimen, the step of preparing a biological specimen for analysis of nucleic acid material is carried out by lysis in detergent, or in an alkaline medium, or through the use of chaotropic agents. This is followed by purification of the DNA or RNA using affinity chromatography (this is useful for mRNA, and uses oligo-dT to purify mRNA), or by centrifugation in CsCl gradients (useful for both DNA and RNA), or by destruction of contaminating material using proteases (to destroy protein) and specific nucleases (to destroy unwanted DNA or RNA). The material can be directly applied to a membrane, separated by gel electrophoresis, or further analyzed by restriction digestion before gel electrophoresis. The final material is immobilized on a membrane capable of binding nucleic acid. The steps of incubating nucleic acid material from this biological specimen with an oligonucleotide probe specific for a nucleic acid sequence encoding a segment of GTVap, removing unbound oligonucleotide probe from the nucleic acid material, and determining oligonucleotide probe bound to a nucleic acid sequence encoding a segment of GTVap are carried out in the manner known to those skilled in the art.

Figure 20D:
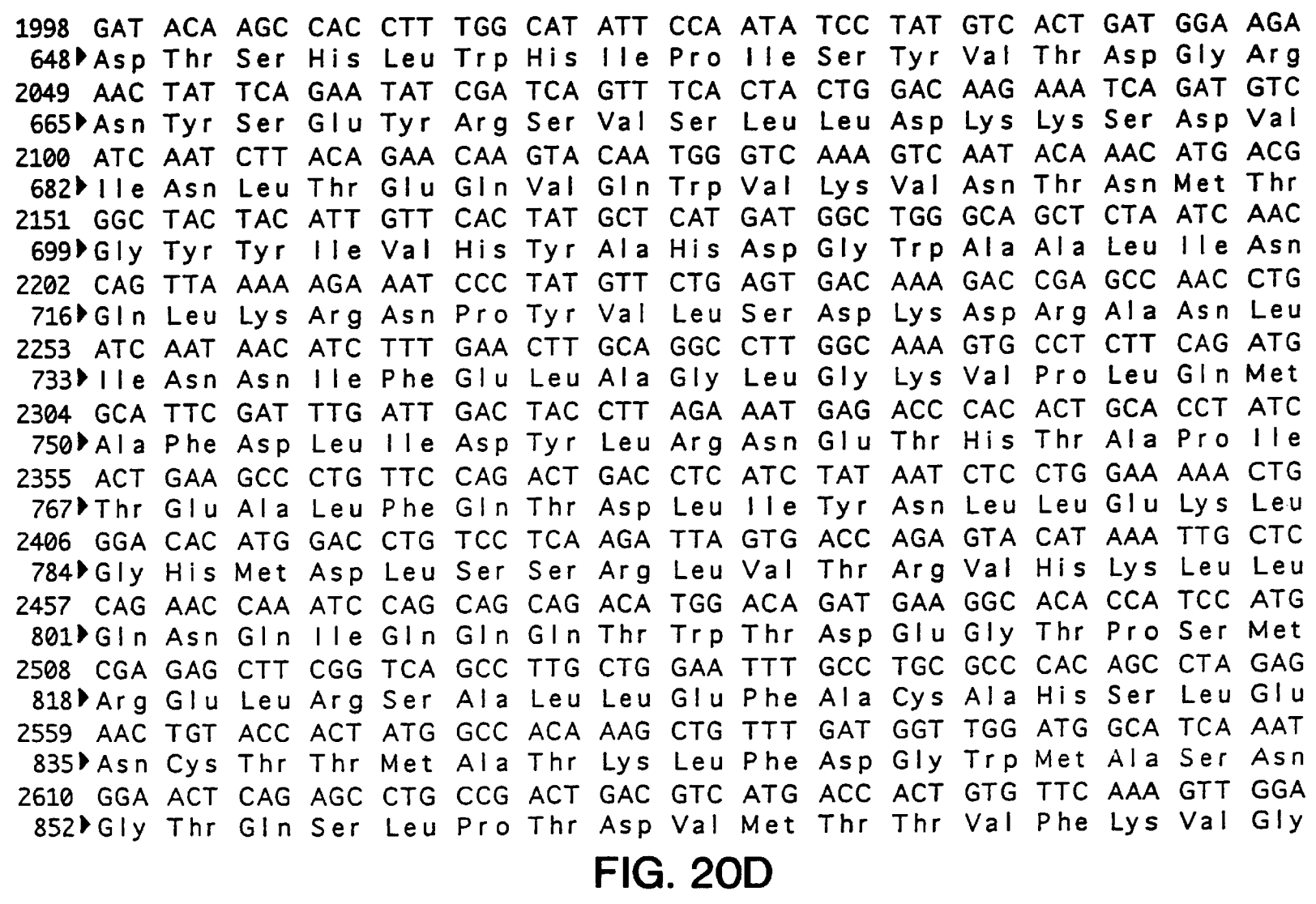

In a ninth aspect, the invention relates to a nucleic acid sequence which encodes GTVap. More particularly, the invention relates to a purified nucleic acid consisting essentially of a nucleic acid encoding a GTVap having the amino acid sequence depicted in Sequence ID NOs 15 and 16, or to a nucleic acid able to hybridize to the complement thereof under stringent conditions and which encodes a GTVap. These are shown in FIG. 20. It should be noted that some DNA clones include an AGC series of nucleotides which is absent in other clones, resulting in a GLN in certain of the resultant predicted proteins; this is shown by the boxes in FIG. 20, and in the sequences identified as SEQ ID NO: 15 (which contains the insert) and SEQ ID NO: 16 (which does not contain the insert), which are the same except for this difference. This nucleic acid sequence may be used to identify or purify nucleic acid sequence encoding GTVap from biological sources using methods known to those skilled in the art. Oligonucleotides derived from a region of this nucleic acid sequence or able to hybridize to this sequence or to its complement, can be used to identify mutations in this sequence that are present in biological sources. The nucleic acid may also be inserted in a vector possessing a heterologous promoter and recombinant protein expressed by inserting this into a cell. The recombinant protein may be full length GTVap or a mutein thereof. The preferred expression system is a homogeneous population of cells, each possessing a cloned nucleic acid encoding a GTVap or a mutein thereof having the amino acid sequence depicted in FIG. 20 (SEQ ID NOs 15 and 16) or a nucleic acid able to hybridize to the complement thereof under stringent conditions and which encodes a GTVap. The preferred cells are mammalian cells stably expressing GTVap protein, although prokaryotic and other eukaryotic cells may be used. A method of producing GTVap comprises the steps of culturing cells possessing a cloned nucleic acid encoding a GTVap as defined above in medium to form a population of cells which expresses GTVap, and purifying GTVap from the cells or from the culture medium. The GTVap may be purified using the method described above or other methods known to those skilled in the art. The recombinant GTVap may be used as a source of enzymatically active aminopeptidase for research or therapeutic purposes.

In a tenth aspect the invention relates to a polypeptide which encodes the retention sequence of a protein, and is selected from the group consisting of a first polypeptide, comprising the following sequence of amino acid residues:- $X^1$aa-Xaa-$(X^1$aa$)_3$-(Xaa$)_{2-3}$-Tyr-Glu-(Xaa$)_{1-3}$-Ser-(Xaa$)_{0-1}$-$X^2$aa-(Xaa$)_{0-4}$-Leu-Leu- (SEQ ID NO: 20), and a second polypeptide, the reverse of the first, comprising the following sequence of amino acid residues: -Leu-Leu-(Xaa$)_{0-4}$-$X^2$aa-(Xaa$)_{0-1}$-Ser-(Xaa$)_{1-3}$-Glu-Tyr-(Xaa$)_{2-3}$-$(X^1$aa$)_3$-Xaa-$X^1$aa- (SEQ ID NO: 21*); wherein Xaa represents any amino acid residue, $X^1$aa represents Pro, Glu, or Asp, and $X^2$aa represents Arg or Lys, and muteins thereof. FIG. 21 shows these GTVap and GLUT4 retention and sorting consensus sequences.

Particular examples of such polypeptides are those in which the retention sequence is His Pro Leu Glu Pro Asp Glu Val Glu Tyr Glu Pro Arg Gly Ser Arg Leu Leu (SEQ. ID NO 17); His Glu Met Asp Glu Asp Glu Glu Asp Tyr Glu Ser Ser Ala Lys Leu Leu (SEQ. ID NO 18); or Leu Leu Glu Gln Glu Val Lys Pro Ser Thr Glu Leu Glu Tyr Leu Gly Pro Asp Glu Asn Glu (SEQ. ID NO 19). The retention sequence represented by sequence ID No. 20 is found in GTVap as sequences ID NOs 17 and 18. That represented by seq. ID NO 21 can be found in GLUT4 as sequence ID NO. 19. These polypeptides (SEQ ID NOs 17–21) may be synthesized by chemical means known to those skilled in the art or expressed by recombinant means, and would serve as useful reagents for identification of modulators of intracellular trafficking.

A method for identifying an insulin sensitive retention sequence of a protein other than GTVap whose sorting is regulated by insulin comprises determining the amino acid sequence of the protein, comparing its sequence with the amino acid sequence of the polypeptide of SEQ ID NO. 20 or 21, and identifying an amino acid sequence of the protein which contains or is homologous to the amino acid sequence of the polypeptide (SEQ ID NOs 20 or 21). Once such retention sequences are identified in such other proteins, these proteins are implicated as materials which sort in the manner of GLUT4 and GTVap, and would thus likely be regulated by insulin.

The invention also relates to a method for identifying an intracellular sorting protein or active fragment thereof which binds to an insulin sensitive retention sequence of a second protein. This method comprises 1) incubating the intracellular sorting protein with the retention sequence under conditions favorable for binding between the sorting protein and the retention sequence, and 2) identifying specifically bound sorting protein. Such a method could involve immobilization of the retention sequence, followed by addition of a cell extract containing the intracellular sorting protein. Nonspecifically bound proteins would be removed, then the intracellular sorting protein would be eluted and analyzed. An alternative method would involve expression of the retention sequence as a bait in the "two-hybrid" system and the screening of a library to identify a DNA encoding a protein that specifically interacts with the sequence. Such a protein would be the intracellular sorting protein. This material, in combination with the retention sequence, will allow for the identification of compounds which disrupt their interaction.

In accordance with the foregoing, a method for identifying a compound capable of altering the intracellular sorting of at least one of GLUT4 and GTVap comprises: a) incubating an intracellular sorting protein or active fragment thereof with the polypeptide retention sequence of sequence ID NOs 20 or 21 under conditions favorable for binding between the sorting protein and the retention sequence in the presence and absence of a test compound; b) quantifying specifically bound complexes of the sorting protein and the retention sequence; and c) comparing the degrees of complex formation in the presence and absence of the test compound. Such compounds would be useful for treating syndromes of insulin resistance.

The method of treating syndromes of insulin resistance relates to treatment of conditions such as diabetes, obesity, impaired glucose tolerance, hyperinsulinemia, and other conditions associated with hyperinsulinemia such as, but not limited to, Syndrome X, hyperlipidemia, and hypertension. Dosages and times of administration would be in accordance with standard protocols, with the therapeutic aim of lowering blood glucose levels, plasma glucose levels, surrogate markers such as glycated proteins such as hemoglobin $A_{1c}$, and insulin levels, such as, for example, (depending on the specific modulator) orally, transcutaneously, or intranasally, or in an injectable form, subcutaneously, intramuscularly, or intravenously, or by other suitable means, and would have an insulin mimetic activity or insulin enhancing activity. The claimed method can be used alone or in combination with other therapies for treatment of insulin resistance and related syndromes.

Further details will be readily apparent without undue experimentation to those skilled in the art.

Material and Methods

The following list of terms, sources, instruments, etc. is provided to aid the reader in understanding and reproducing the experimental work to be presented below.

Abbreviations and Descriptions

Cellular membrane fractions: PM (plasma membrane), HDM (high density microsomes), and LDM (low density microsomes ) are cellular membrane fractions defined by their intrinsic density and sedimentation behavior during centrifugation and by their enrichment of particular enzymes that typify these membranes.

GTVap stands for Glucose Transporter Vesicle amino peptidase.

GTVap1 refers to rabbit polyclonal antibody produced from the peptide Phe-Ala-Ala-Thr-Gln-Phe-Glu-Pro-Leu-Ala-Ala-[Cys] [SEQ ID NO: 8] that react with the different forms of GTVap.

KRBH buffer is 120 mM NaCl, 4 mM $KH_2PO_4$, 1 mM $CaCl_2$, 10 mM $NaHCO_3$ and 30 mM HEPES, and has a pH of 7.4.

RACE is Rapid Amplification of cDNA Ends

TBS (Tris buffered saline) is 10 mM Tris, 150 mM NaCl, 0.01% Thimerosal, pH 8.0.

TBS-TW is TBS with 0.05% Tween-20.

TES (Tris-EDTA-sucrose) buffer is 20 mM Tris, 1 mM EDTA, 250 mM sucrose, pH 7.5.

SDS-PAGE is sodium dodecyl sulfate—polyacrylamide gel electrophoresis.

Reagents

Actinonin was obtained from Sigma Chemical Co., St. Louis, Mo.

Amastatin was obtained from Sigma Chemical Co., St. Louis, Mo.

ω-aminohexyl Sepharose 4B was obtained from Sigma Chemical Co., St. Louis, Mo.

AmpliTaq DNA polymerase was obtained from Perkin Elmer, Norwalk, Conn.

Benzamidine was obtained from Sigma Chemical Co., St. Louis, Mo.

Bestatin was obtained from Sigma Chemical Co., St. Louis, Mo.

BSA (bovine serum albumin-Fraction V) was obtained from Sigma Chemical Co., St. Louis, Mo.

Collagenase was obtained from Worthington, Freehold, N.J.

Coomassie blue G-250 and SDS (sodium dodecyl sulfate) were obtained from BioRad, Hercules, Calif.

Cytochalasin B was obtained from Sigma Chemical Co., St. Louis, Mo.

DFP (diisopropylfluorophosphate) was obtained from Aldrich, Milwaukee, Wis.

EDTA is ethylenediaminetetraacetic acid and was obtained from Sigma Chemical Co., St. Louis, Mo.

Expand DNA thermostable DNA polymerase was obtained from Boehringer Mannheim, Indianapolis, Ind.

HEPES is N-(2-hydroxyethyl)piperazine-N'-(2-ethanesulfonic acid) and is obtained from Sigma Chemical Co., St. Louis Mo.

IAV matrix, Immobilon (AV) membrane was obtained from Millipore Corp., Milford, Mass.

IDAC stands for iminodiacetic acid chelation resin, obtained from Pierce, Rockford, Ill.

Insulin (porcine) was obtained from Eli Lilly, Indianapolis, Ind.

Leupeptin was obtained from Sigma Chemical Co., St. Louis, Mo.

L-leucinethiol was obtained from Sigma Chemical Co., St. Louis, Mo.

Marathon RACE kit was obtained from Clontech, Palo Alto, Calif.

Oligonucleotides were obtained from Midland Certified Reagent Company, Midland, Tex.

Pepstatin A was obtained from Sigma Chemical Co., St. Louis, Mo.

PMSF (phenylmethylsulfonyl fluoride) was obtained from Sigma Chemical Co., St. Louis, Mo.

Problot membranes were obtained from Applied Biosystems, Foster City, Calif.

PVDF membrane is polyvinylidene difluoride, Millipore Corp., Bedford Mass.

Rat heart RACE Ready cDNA (7383-1) was obtained from Clontech, Palo ALto, Calif.

Rat skeletal muscle cDNA library (RL3003b) was obtained from Clontech, Palo Alto, Calif.

Rat skeletal muscle polyA+ RNA was obtained from Clontech, Palo Alto, Calif.

Resource Q anion exchange resin contains quaternary ammonium groups on rigid polystyrene/divinylbenzene beads 15 μm in diameter and was obtained from Pharmacia, Piscataway, N.J.

Retrotherm thermostable RNA and DNA dependent DNA polymerase was obtained from Epicentre Technologies, Madison, Wis.

Sequenase kits were from United States Biochemical, Cleveland, Ohio.

Sinapinic acid (3,5 dimethoxy-4-hydroxycinnamic acid) was obtained from Aldrich, Milwaukee, Wis.

sMBS (m-maleimidobenzoyl-N-hydroxysulfosuccinimide ester) was obtained from Pierce, Rockford, Ill.

Streptavidin was purchased from Zymed Corp., South San Francisco, Calif.

Supelcosil LC-18-DB, 3 μm, 2.1×250 mm columns were obtained from Supelco Corp., Bellefonte, Pa.

TEA (triethylamine) was obtained from Pierce, Rockford, Ill.

3' RACE kit was obtained from Clontech, Palo Alto, Calif.

TFA (trifluoroacetic acid) was obtained from Applied Biosystems, Foster City, Calif.

Thimerosal is sodium ethyl mercurithiol salicylate, available from Sigma Chemical Co., St. Louis, Mo.

Tris stands for tris hydroxyaminomethane.

Triton X-100 was obtained from Sigma Chemical Co., St. Louis, Mo.

Trypsin (modified sequencing grade, porcine) was obtained from Promega, Madison, Wis.

WGA stands for wheat germ lectin-Sepharose 6 MB, which was obtained from Pharmacia, Piscataway, N.J.

Radiolabeled Materials and Scintillation Fluids $^{125}$I-Protein A (2–10 μCi/μg) was used for Western blot analyses.

All isotopes and scintillation fluids (Aquasol) were from New England Nuclear, Boston, Mass. or Amersham Corporation, Arlington Heights, Ill.

General Methods of Peptide Synthesis

All peptides including the COOH-terminal 15 amino acid residues of the rat GLUT4 sequence (495–509; [Cys]-Lys-Pro-Ser-Thr-Glu-Leu-Glu-Tyr-Leu-Gly-Pro-Asp-Glu-Asn-Asp (SEQ ID NO: 9)) and fragments thereof (Lys-Pro-Ser-Thr-Glu-Leu-Glu-[Cys] (SEQ ID NO: 10); Thr-Glu-Leu-Glu-Tyr-Leu-[Cys] (SEQ ID NO: 11); [Cys]-Gly-Pro-Asp-Glu-Asn-Asp (SEQ ID NO: 12); the GTVap peptide (Phe-Ala-Ala-Thr-Gln-Phe-Glu-Pro-Leu-Ala-Ala-[Cys] (SEQ ID NO: 8)) and the insulin-derived peptides were synthesized using solid phase methods on the 430A peptide synthesizer previously described in U.S. Pat. No. 5,225,354 of Knowles and Marchesi. All peptides were synthesized with a cysteine residue at the —NH$_2$ or —COOH terminus identified as [Cys] in the sequence and were covalently attached to ω-aminohexyl Sepharose 4B or to a fluorophore for monitoring the proteolytic cleavage of insulin-derived peptides. The peptides were labeled with sulfhydral-specific fluorescein conjugates. In this procedure a two-fold molar excess of fluorescein-5-maleimide in dimethyl-formamide (40 mg/ml) was added to the peptide (10 mg/ml) in 100 mM sodium phosphate, 5 mM EDTA, pH 7.1 and incubated for 20 hours at room temperature. The resulting peptide-fluorescein conjugate was purified by HPLC chromatography as described by Knowles and Marchesi, U.S. Pat. No. 5,225,354.

Instrumentation

The 477a Protein Sequencer, the 120A Amino acid analyzer and the 430A peptide synthesizer were from Applied Biosystems, Foster City, Calif.

$^{125}$I was measured in a Wallac (LKB) 1272 Clinigamma Counter.

HPLC data acquisition and analysis of the tryptic digests of 155 kD and 165 kD proteins was performed on a Nelson Turbochrome System (Perkin-Elmer Nelson, Norwalk, Conn.)

Mass spectrometry for mass analysis of the synthetic peptides and insulin fragments was performed using a Kratos Maldi 3 laser desorption-time of flight mass spectrometer (LD-TOF-MS), with saturated sinapinic acid, 0.1% TFA, 50% acetonitrile as the matrix.

General Method for Protein Determination

Protein quantities were determined using the bicinchoninic acid method (BCA) as described by the manufacturer (Pierce, Rockford, Ill.)

Immunoaffinity Purification of Anti-Peptide Antibodies

The GLUT4 and GTVap anti-peptide antibodies were purified by immunoaffinity absorption prior to their use in Western blots or for the purification of GLUT4 vesicles. For this purpose, the peptide immunogens containing a single cysteine were coupled to Sepharose, as described by the following method. ω-aminohexyl Sepharose 4B resin was washed with 50 mM Na$_2$PO$_4$, 10 mM EDTA, pH 7.0. The resin was suspended in a 50% slurry and sMBS (2 μmoles/ml resin) added. After 10 minutes at ambient temperature, the derivitized resin was washed in 50 mM Na$_2$PO$_4$, 10 mM EDTA, pH 7.0, and resuspended to a 50% slurry. The cysteine-containing peptide was added (1–2 mg peptide/ml) and reacted overnight at ambient temperature. The resulting peptide-resin conjugate was washed with 0.1M acetic acid and then 50 mM Na$_2$PO$_4$, 10 mM EDTA, pH 7.0 prior to use.

For immunoaffinity purification, polyclonal antisera to the individual peptides were diluted 1:1 with 100 mM NaH$_2$PO$_4$, 150 mM NaCl, pH 7.5 and applied to the corresponding peptide-resin. Following a brief wash with the above buffer, the bound affinity-purified antibody was eluted with 0.1M acetic acid and the pH immediately adjusted to pH 8.0 with 1.0M Tris base. The purified antibody was dialyzed against and stored in 0.1M sodium borate pH 8.0 containing 0.5% sodium azide.

Western Blot Analysis

Prior to Western blot analysis, proteins were electrophoresed on SDS-PAGE gels (Laemmli, Nature, 277, 680–685, 1970) and transferred to PVDF or Problot membranes by the method of Tobin, et al, PNAS, 76, 4350–4354, 1979. For Western blot analysis of GLUT4 and GTVap, rabbit anti-GLUT4 antibody, immunoaffinity-purified as above, was used at a 1:5000 dilution (1 μg/5 ml); GTVap affinity purified antibody was used at 1:1000 (1 μg/ml). For detection of the primary antibody, both Protein A $^{125}$I (1 μCi/ml) and goat anti-rabbit alkaline phosphatase (1:10,000; Promega) were used sequentially. The immunoreactive bands were identified by the colored alkaline phosphatase reaction product and/or by autoradiography of the $^{125}$I-Protein A, and were quantified by $^{125}$I-Protein A counting on a LKB 1272 Clinigamma counter.

Experimental and Results

Generation of GLUT4 Specific Antibodies

GLUT4 rabbit polyclonal antibody was produced using a synthetic peptide corresponding to the COOH-terminal 15 amino acid residues of the rat-GLUT4 sequence, i.e., residues 495–509, [Cys]-Lys-Pro-Ser-Thr-Glu-Leu-Glu-Tyr-Leu-Gly-Pro-Asp-Glu-Asn-Asp (SEQ ID NO: 9). The antibody specificity for GLUT4 was enhanced by absorbing the polyclonal sera with 3 peptides (Lys-Pro-Ser-Thr-Glu-Leu-Glu-[Cys] (SEQ ID NO: 10); Thr-Glu-Leu-Glu-Tyr-Leu-[Cys] (SEQ ID NO: 11); [Cys]-Gly-Pro-Asp-Glu-Asn-Asp (SEQ ID NO: 12) covalently attached to ω-aminohexyl Sepharose 4B using the heterobifunctional reagent sMBS. The nonabsorbed GLUT4 specific antibody was purified on a 495–509 peptide column and then on Protein-A Sepharose. The resulting highly purified and specific GLUT4 antibody was used for Western blotting at a 1:5000 dilution (1 μg protein/5 ml diluent).

Preparation and Isolation of Rat Adipocytes

Epididymal fat pads from 125 g Sprague-Dawley rats were removed and immediately placed in KRBH buffer containing 1% BSA, 2.5 mM glucose and 200 nM adenosine. The fat was minced, collagenase was added to 3 mg/ml, and the mixture was incubated at 37° C. for 45 minutes with shaking. The dissociated adipocytes were filtered through a 250 micron nylon screen and washed 3 times (using mild centrifugation) with KRBH containing 1% BSA and 200 nM adenosine. The cells were resuspended in the wash buffer containing 3% BSA.

Fractionation of Rat Adipocytes

The membrane fractions PM, HDM and LDM were prepared generally according to Simpson et. al., Biochimica et Biophysica Acta, 763, 393–407 (1983). Isolated adipocytes were homogenized in a chilled Wheaton 55 ml teflon pestle homogenizer for ten strokes. The fat layer was removed following a 10,000×g centrifugation and the remaining material was rehomogenized. The PM fraction was pelleted at 16,000×g and the supernatant was recentrifuged to remove any additional PM. The PM were resuspended and rehomogenized then purified away from DNA and mitochondrial organelles by ultracentrifugation through a 1.12M sucrose cushion at 96,000×g. The PM were collected from the interphase of the sucrose cushion. The HDM were pelleted from the initial supernatant at 48,000×g and the resulting supernatant was recentrifuged to remove any remaining HDM. The LDM were collected on a 1.12M sucrose cushion from the HDM supernatant by centrifugation of at 212,000×g. The LDM were collected from the sucrose interphase and this step was repeated three times with LDM pooled from additional tubes to concentrate the LDM and to remove any contaminating cytosolic proteins.

Immunopurification of the GLUT4 Vesicles

Purified GLUT4 specific antibody prepared as above was biotinylated using NHS-biotin in 50 mM NaHCO$_3$, pH 8.2, for 30 minutes at room temperature. Following dialysis against 20 mM Tris, 1 mM EDTA, pH 8.0, the active biotinylated antibody was recovered by affinity purification on [Cys]-Lys-Pro-Ser-Thr-Glu-Leu-Glu-Tyr-Leu-Gly-Pro-Asp-Glu-Asn-Asp (SEQ ID NO: 9)) covalently bound to aminohexyl-Sepharose CL-4B as described above.

Immobilon Affinity Membranes (IAV, 1 cm$^2$) were saturated for 6 hours at room temperature and then overnight at 4° C. with 500 μg of streptavidin in 0.5M KH$_2$PO$_4$, pH 7.5. Residual sites were capped with 0.44M glutamic acid (6 hours, room temperature) and the membranes were washed. Biotinylated anti-GLUT4 antibody (50 μg/cm$^2$) described above was added in 100 mM boric acid, 150 mM NaCl, 1 mM EDTA, pH 7.5, and contact was maintained for 6 hours at room temperature. The resulting antibody-derivitized IAV matrix was washed 3 times (20 minutes/wash) in TBS, 0.1% Tween-20, and then transferred into TES. Control IAV matrix was prepared with streptavidin and capped with glutamic acid.

LDM were added to the GLUT4 or control IAV matrices. Typically, the LDM's from 2.4 rats were added to each 1 cm$^2$ of matrix, and incubated overnight at 4° C. in TES containing 150 mM NaCl, and subsequently washed 3× in the same buffer. Unbound vesicles were recovered by centrifugation at 212,000×g. Bound vesicular protein was recovered by eluting the matrices with 1.0% SDS in 10 mM Tris-HCL, pH 7.4, or in 0.1% Triton X-100 in 20 mM Tris, 1 mM EDTA, pH 7.4. GLUT4 vesicle proteins were frozen in liquid N$_2$ and stored at −80° C. until further use.

For protein analysis, equal volumes of purified GLUT4 vesicles and controls, along with equal protein loads of recovered unbound LDM vesicles were lyophilized and loaded onto 4–20% SDS-PAGE gels, transferred to PVDF membranes, and stained with Coomassie Blue R-250. A protein having a molecular weight of approximately 165 kD was characterized as being specific to the GLUT4 vesicles and was partially to fully depleted from the unbound fraction.

FIG. 1 shows qualitatively by Western Blot autoradiography that the immunoaffinity absorption using GLUT4 antibody-derivitized IAV matrix results in a significant enrichment of GLUT4 vesicles compared to IAV matrix lacking the GLUT4 antibody. Quantitation of the $^{125}$I Protein A indicated an 8-fold enrichment of GLUT4 in the immunoaffinity-purified vesicles. The immunoaffinity-purified GLUT4 vesicle proteins can be solubilized using 0.1% Triton X-100 or low concentrations (<1%) of SDS, leaving the antibody attached to the covalently bound streptavidin, to yield a protein composition much simpler than the total LDM fraction.

Figure 2:
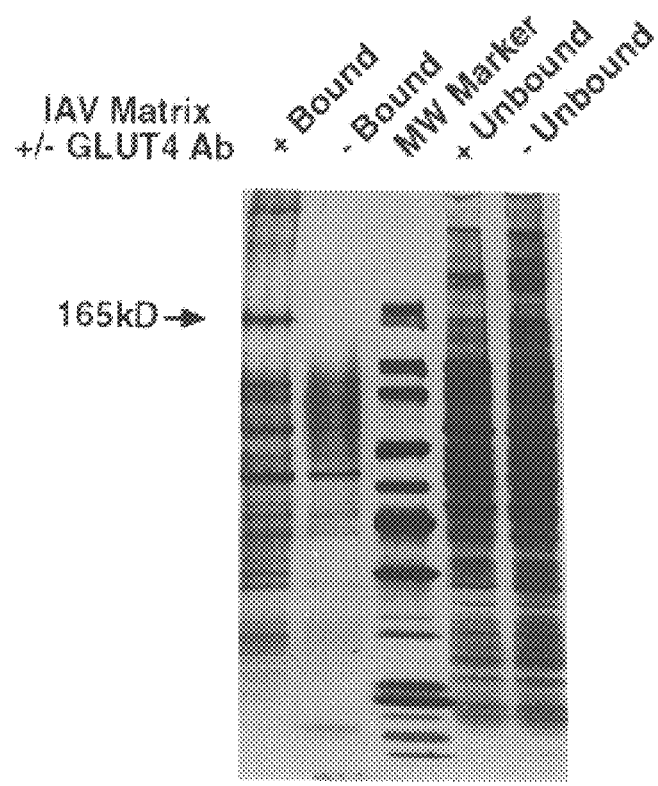
FIG. 2 is a protein stain of immunoaffinity-purified GLUT4 vesicles.

FIG. 2 shows that Coomassie blue staining of the GLUT4 vesicle-associated proteins following SDS-PAGE reveals 165 kD and 155 kD proteins which are uniquely associated with GLUT4 vesicles and which are not found in proteins absorbed onto the IAV matrix lacking the GLUT4 antibodies. Both the 165 kD and 155 kD proteins are depleted from the LDM following adsorption with GLUT4 IAV matrix, but are not depleted after adsorption on the control matrix.

Purification and Sequence Analysis of 165 kD and 155 kD Proteins

GLUT4 vesicle proteins were electrophoretically separated on 20 cm, 7–15% acrylamide, SDS-PAGE gels and transferred to Problot membranes. The 165 kD and 155 kD proteins were identified by Coomassie blue staining. Initial attempts at direct NH$_2$ terminal sequencing from the Problot membrane indicated that the NH$_2$-terminus was blocked. In subsequent experiments the 165 kD and 155 kD proteins were separated and identified as above, and were then digested with trypsin (30:1; substrate/enzyme) according to Fernandez et al., Analyt. Biochem., 201, 255–264 (1992). The resulting peptide products were separated on a Supelcosil LC-18-DB, 3 μm, 2.1×250 mm column using a 3-hour linear gradient of 0.1% TFA to 0.1% TFA, 70% acetonitrile.

The effluent was monitored at 215 nm and selected peaks were subjected to sequencing using an ABI 477a Protein Sequencer operated in the gas phase with an on-line 120A Analyzer and PE Nelson Turbochrome Software.

Figure 3:
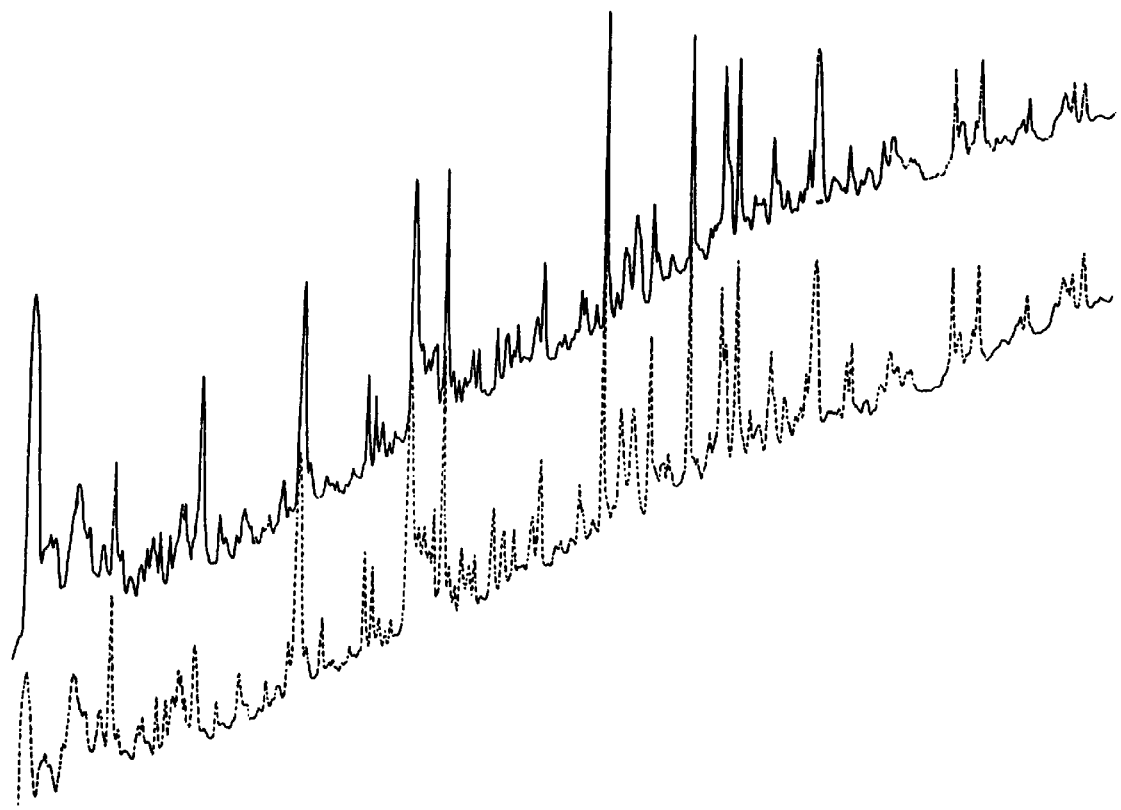
FIG. 3 shows the HPLC profiles of tryptic digests of 165 kD (upper trace) and 155 kD (lower trace) GLUT4 vesicle proteins.

FIG. 3 shows HPLC separations of the tryptic fragments and indicates significant similarity between the two proteins. Selected peptides of moderate hydrophobicity and strong UV absorbance were sequenced. The sequences obtained are shown in Table 1. Both peptides were sequenced from the 165 kD and 155 kD forms and were identical, constituting further evidence of the similarity between these two proteins.

Identification of GLUT4 Vesicle Protein 165 kDa as an Aminopeptidase

The primary sequence obtained was used to search DNA databases including GenBank, EMBL, Nucleic, and GeneSeq, and the Protein databases PIR, PatchX, and SwisSprot. One peptide was found to have 100% homology with a tryptic fragment of a serum aminopeptidase of placental origin in the GeneSeq database. See Table 1.

TABLE 1

Summary of Sequence Data for GTVap-165 and GTVap-155

| Fragment No. | Sequence | Identity |
|---|---|---|
| 1 | Phe-Ala-Ala-Thr-Gln-Phe-Glu-Pro-Leu-Ala-Ala-arg* (SEQ ID NO: 13) | None found |
| 2 | Ile-Leu-Gln-Asn-Gln-Ile-Gln-Gln-Gln-Thr-Arg-Thr-Asp-Glu-Gly-thr-Pro-asn-Met* (SEQ ID NO: 14) | Leucine Amino Peptidase (found in GeneSeq patent database) Accession #GSP:R28142; EP 0 535 241 A1 |

Underlined residues of fragment #1 were used to produce high titered rabbit polyclonal antisera.
Underlined residues of fragment #2 had 100% homology with a previously identified placental leucine aminopeptidase (PLAP).
*Designates same sequence found in both GTVap-165 and GTVap-155
Residues in lower case letter denote less than full confidence, and are assigned the designation Xaa in the claims.

The peptide Phe-Ala-Ala-Thr-Gln-Phe-Glu-Pro-Leu-Ala-Ala-[Cys] (SEQ ID NO: 8) was used to produce rabbit polyclonal antibodies which were subsequently affinity purified as described above. These antibodies are referred to as GTVap1 and were used at a 1:500 dilution for Western blot analysis.

Figure 4:
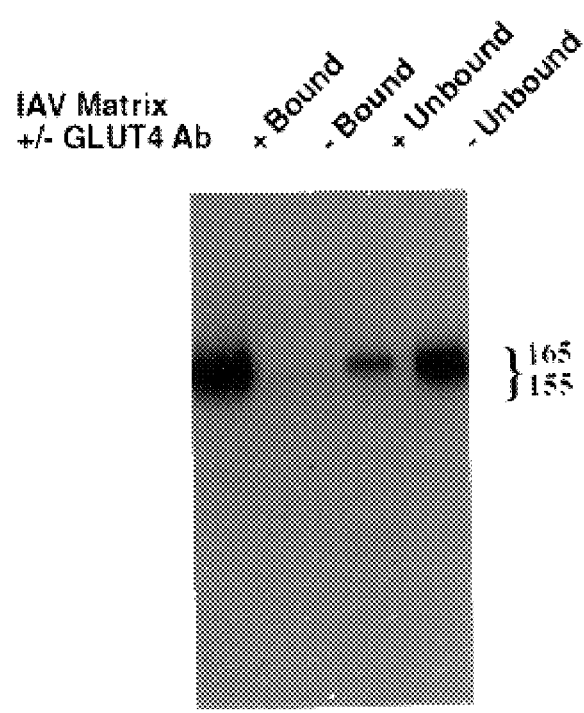
FIG. 4 is a Western blot showing the enrichment of the 165 kD and 155 kD proteins in GLUT4 vesicles.

FIG. 4 shows the affinity purified GTVap1 antibodies in Western blot analysis are specific for the 165 kD and 155 kD proteins on the GLUT4 vesicles and also react with a 120 kD protein which is less abundant than the former two. Relative to the controls, the purified GLUT4 vesicles are significantly enriched in the immunoreactive 165 kD and 155 kD proteins, as measured by Western blot. Quantitation of the $^{125}$I Protein A indicated an 18-fold enrichment of the 165 kD and 155 kD proteins on the immunoaffinity-purified vesicles.

In order to show identity of the 165 kD and 155 kD proteins following removal of the oligosaccharide side chains, LDM was treated with N-glycosidase F. Purified LDM was solubilized in 0.5% SDS and then buffered in 25 mM Hepes, 10 mM EDTA, 1.7% β-octylglucoside, pH 7.5 before being digested with 1 unit of N-Glycosidase F (PNGase F) per sample for 12 or 24 hours at 37° C. Controls (samples lacking the glycosidase) were included for each condition.

Figure 5:
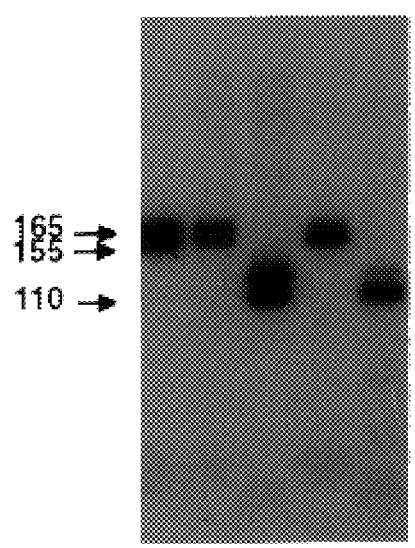
FIG. 5 is a Western blot of the low density microsome (LDM) 165 kD and 155 kD proteins following treatment with N-Glycosidase F.

FIG. 5 indicates that treatment of LDM with N-glycosidase F results in the conversion of both the 165 kD and 155 kD immunoreactive proteins to a single immunoreactive protein of 110 kD. It is therefore likely that both forms are identical at the protein level with differences existing in the number and/or length of oligosaccharide side chains of the glycosylated 165 kD and 155 kD forms.

The 165 kD and 155 kD Proteins have Sequence Homology to a Previously Identified Aminopeptidase, and GLUT4 Vesicles are Enriched in Aminopeptidase Activity As indicated in Table 1, the peptide sequence of fragment #2 had 100% homology with a previously reported plasma aminopeptidase of placental origin (Tsujimoto et al. EPA Pub. #EP 0 535 241 A1).

Figure 6:
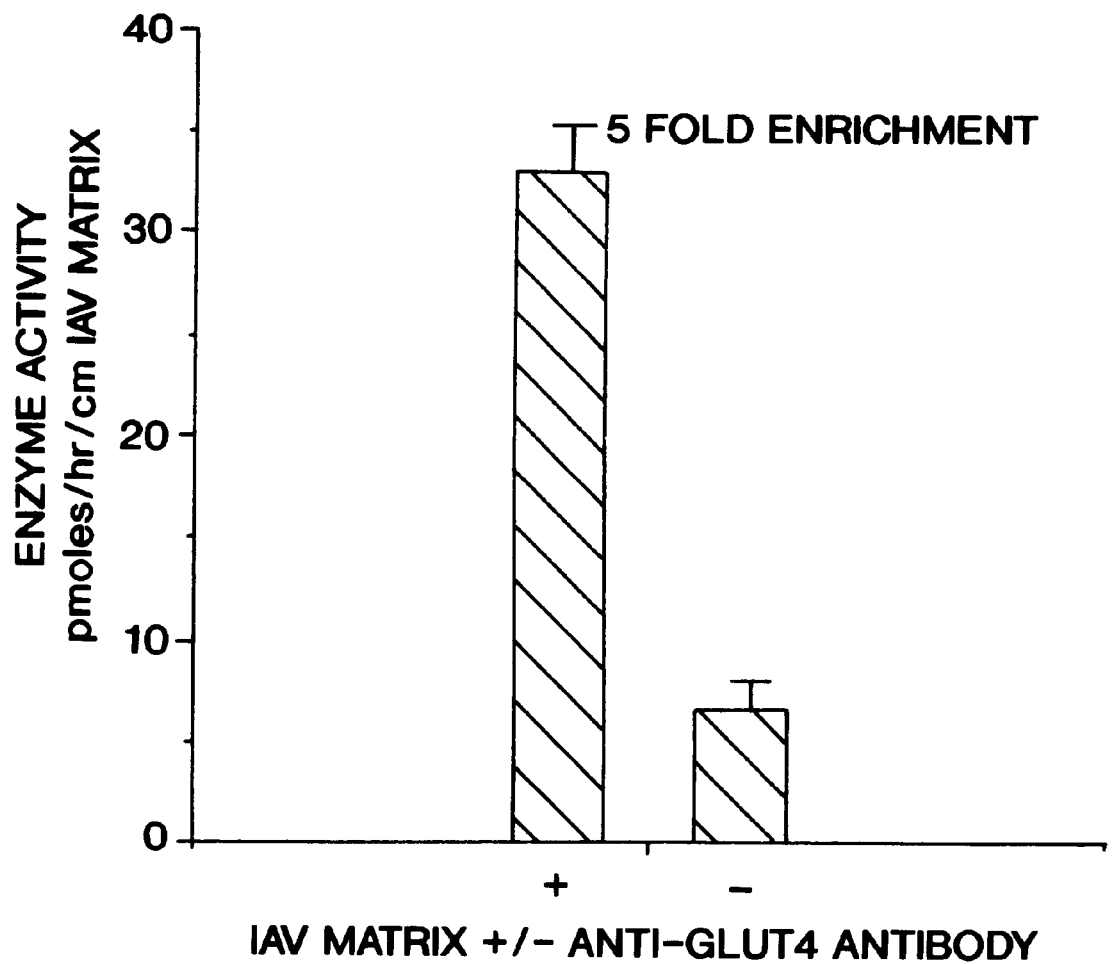
FIG. 6 is a graph showing the quantitative enrichment of aminopeptidase activity in GLUT4 vesicles.

The synthetic substrate leucine p-nitroanilide was used to confirm that aminopeptidase activity was co-purified with GLUT4 vesicles. Immunoaffinity purified GLUT4 vesicles or vesicles bound non-specifically to the control IAV membranes were extracted with 20 mM Tris, 0.1% Triton X-100, pH 7.5. Equal volumes of extract from the two matrices were assayed for aminopeptidase activity using 1.6 mM leu-p-nitroanilide. The results, shown in FIG. 6, indicate that GLUT4 vesicles contain 5-fold more aminopeptidase activity that the control IAV matrix. Therefore, aminopeptidase activity co-purifies with GLUT4 vesicles.

Throughout this application the term Glucose Transporter Vesicle aminopeptidase or GTVap is used to designate the aminopeptidases associated with GLUT4 vesicles.

Identification of GTVaps in PM and HDM Membranes

Figure 7:
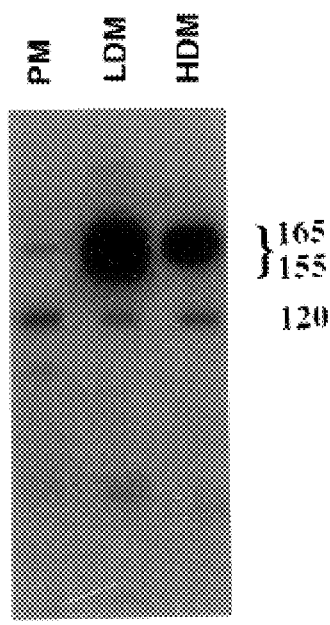
FIG. 7 is a Western blot of the 165 kD, 155 kD and 120 kD proteins in rat adipocyte membrane fractions.

As shown in FIG. 7, the GTVaps are also found in PM and HDM fractions by Western blot analysis using the GTVap1 antibody. The GTVap-165 and GTVap-155 are the predominant forms in the HDM and LDM, whereas in the PM these GTVap's are much less abundant.

Figure 8:
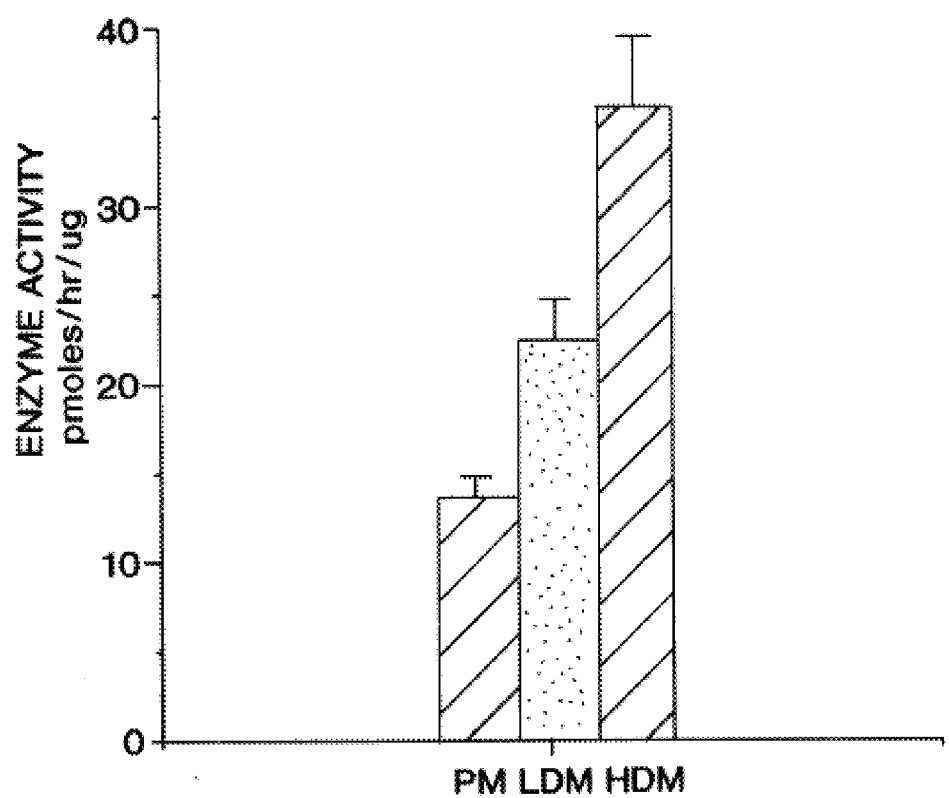
FIG. 8 is the GTVap enzyme activity in rat adipocyte membrane fractions.

General Methods for the Extraction of and Assay of GTVaps from PM, LDM, and HDM Membranes The GTVaps can be maximally extracted (>95%) from the LDM, HDM, and PM membranous compartments using low concentrations of detergents. Unless otherwise indicated, the GTVaps were solubilized from GLUT4 vesicles, LDM, HDM, and PM using 0.1% Triton X-100 in 20 mM Tris, pH 7.5 at 4° C. for 15 minutes. The insoluble material was pelleted at 20,000×g for 20 minutes and discarded. The enzyme extract (10–20 μg protein) was assayed using 1.6 mM leucine p-nitroanilide in 20 mM Tris-HCl, 0.1% Triton X-100, pH 7.5 in 250 μl volume at 37° C. The UV absorbance of the p-nitroanilide product was measured at 405 nm and quantified by comparison to p-nitroanilide standards. The results are reported as pmoles p-nitroanilide produced per μg protein/hour at 37° C. unless otherwise noted. Alternatively, the results are presented as change in OD at 405 nm if the protein was too low to determine (eg column fractions) or a relative comparison was being made. As shown in FIG. 8, the PM, LDM, and HDM contain GTVap activity.

Although the GLUT4 vesicles were shown initially to have aminopeptidase activity, it was necessary to confirm that the 165 kD and 155 kD proteins were indeed the aminopeptidases. Due to the limited amount of protein obtainable from the purified GLUT4 vesicles or LDM, it was necessary to characterize and purify the enzyme from the HDM.

Characterization of the Activity of the GTVap Enzyme

To characterize the relative reactivities of GTVap to different amino acid p-nitroanilide substrates, an HDM extract was prepared as described above and incubated with each substrate at a concentration of 1.6 mM as described above. As shown in Table 2, the relative activity of GTVap to the synthetic amino acid p-nitroanilide substrates are leucine>>proline, alanine>valine, glycine.

To characterize the relative reactivities of GTVap to different amino acid β-napthylamide substrates, a GLUT4 vesicle extract was prepared as described above and incubated with each substrate at a concentration of 200 uM as described above. As shown in Table 2A, the relative activity of GTVap to the synthetic amino acid-β-napthylamide substrates are leucine>lysine>arginine>methionine>alanine>phenylalanine.

Figure 9:
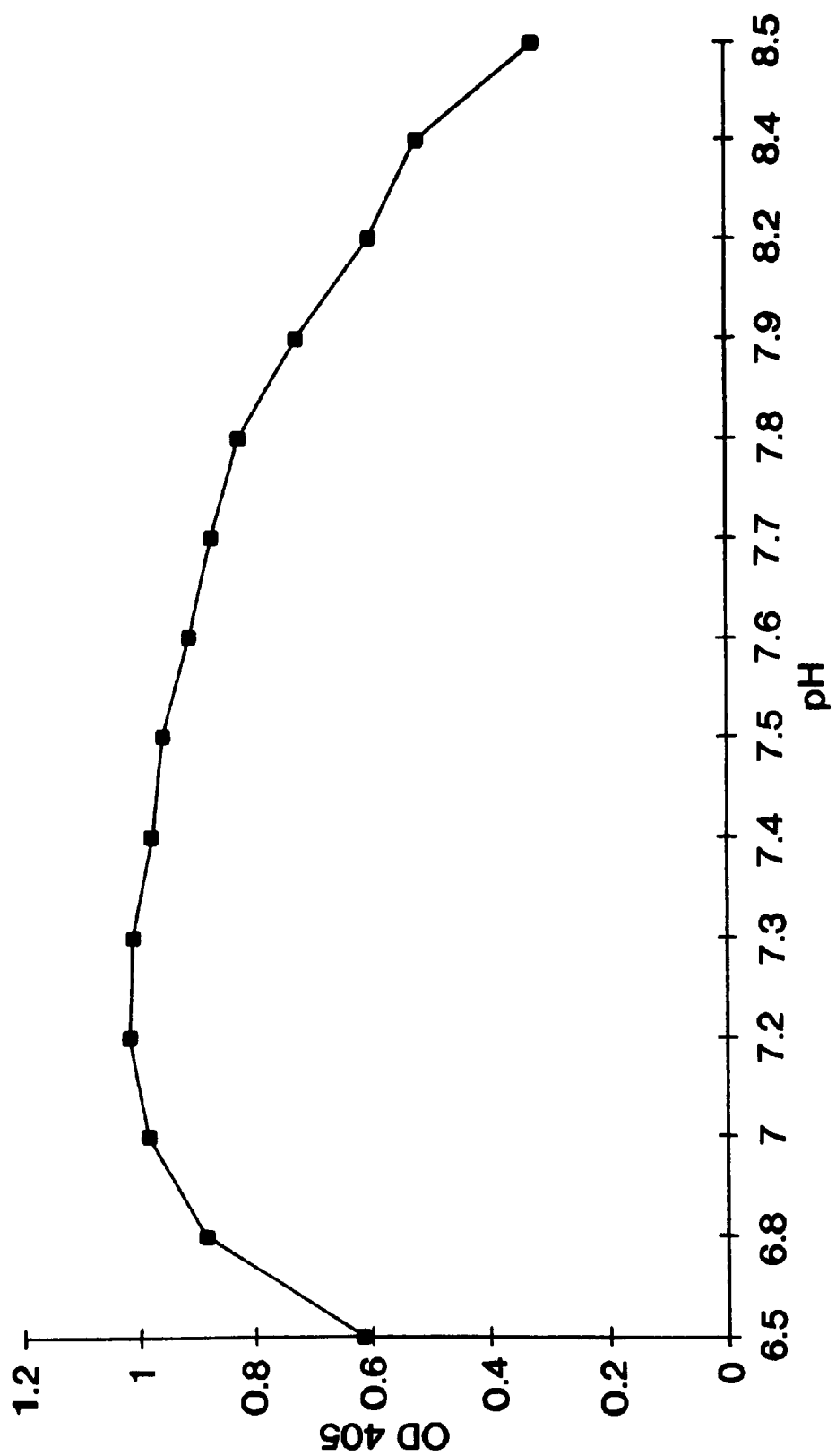
FIG. 9 is a graph showing the pH optimum of GTVap.

To determine the optimal pH of the GTVap activity, an HDM extract was prepared as above and was diluted 1:9 into 100 mM Tris base, 0.1% Triton X-100 which had been previously adjusted to the indicated pH values with HCl. Following incubation for 15 minutes, the leucine p-nitroanilide substrate was added and the enzyme activity determined as above. The results shown in FIG. 9. indicate that the enzyme has a broad neutral pH optimum.

TABLE 2

Relative activity of GTVap with various amino acid-p-nitroanilide substrates

| Amino acid-p-nitroanilide | nmoles/μg protein/hr |
|---|---|
| leucine | 2.9 |
| proline | 0.35 |
| alanine | 0.33 |
| valine | 0.09 |
| glycine | 0.08 |

TABLE 2A

Relative activity of GLUT4 vesicle GTVap with various amino acid-β-napthylamide substrates

| Amino acid-β-napthylamide | nmoles/25 uL extract/hr |
|---|---|
| leucine | 9.5 |
| lysine | 7.9 |
| arginine | 6.5 |
| methionine | 2.9 |
| alanine | 1.3 |
| phenylalanine | 0.9 |

Figure 10:
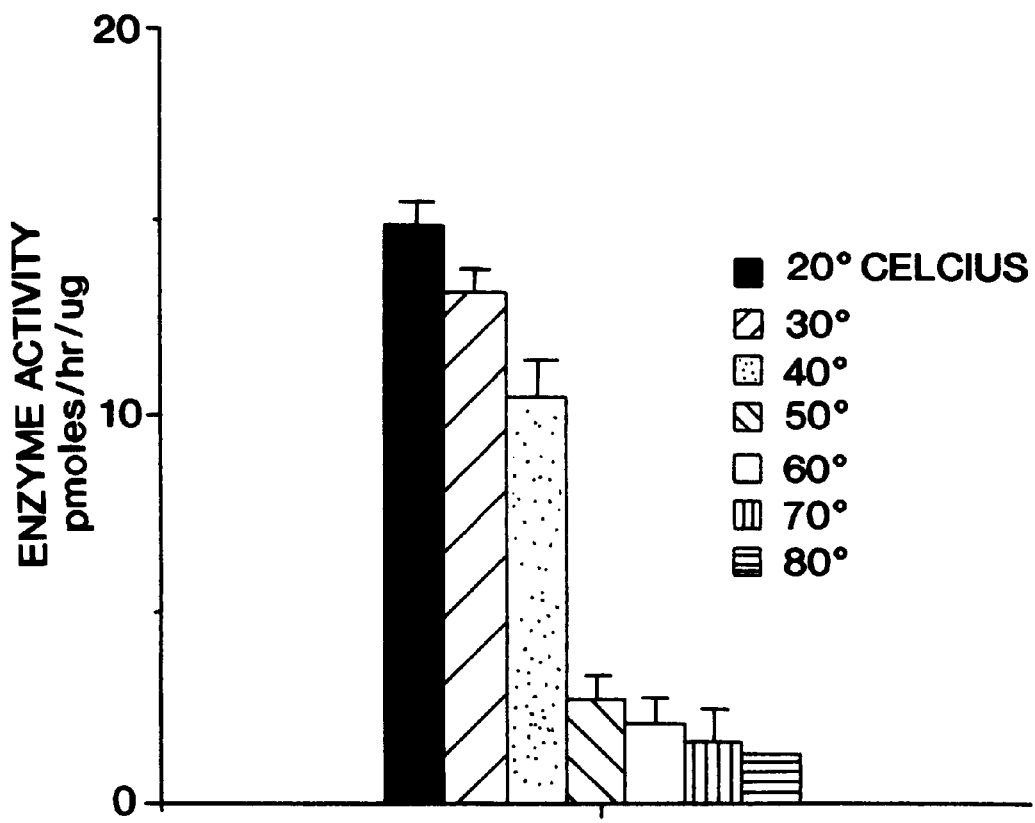
FIG. 10 is a graph showing the temperature stability of GTVap.

To determine the temperature stability of GTVap, HDM extracts were incubated at various temperatures for 20 minutes prior to enzyme analysis as described above. The results shown in FIG. 10 indicate a temperature-dependent inactivation with a 25% reduction in activity between 20° C. and 40° C. Between 40° C. and 50° C. there is a further major drop in activity, resulting in a 75% inhibition compared to the 20° C. incubation.

Figure 11:
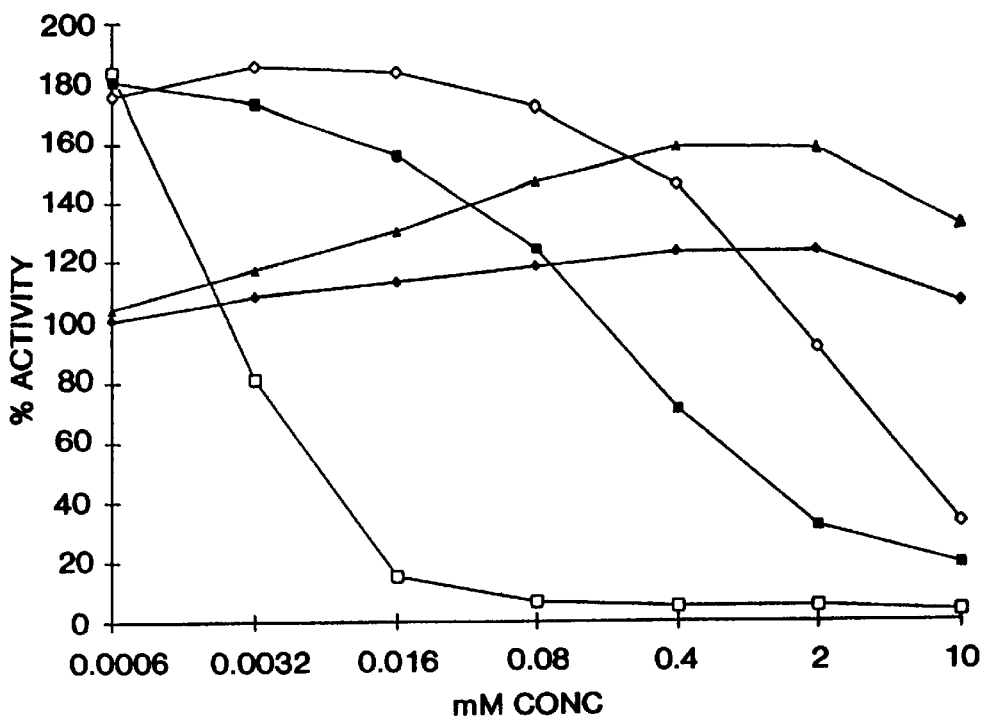
FIG. 11 is a graph of the effect of various ions on GTVap activity: Co (solid squares); Zn (open squares); Mg (solid diamonds); Mn (open diamonds); Ca (solid triangles)

The known aminopeptidases require bound ions for the optimal stabilization of structure and for maximal enzymatic activity. To explore the ion requirements for GTVap, Triton X-100 extracts of HDM were incubated with various ions for 15 minutes at 37° C. before the addition of the leu-p-nitroanilide substrate. The results, shown in FIG. 11, demonstrate that particular ions can both activate and inhibit the enzyme activity. It is also evident that the enzyme has significant activity (approx. 55% of maximal activity) without the addition of divalent cations. Zinc, cobalt and manganese optimally activate at μmolar concentrations and inhibit at mmolar concentrations. Calcium and magnesium also partially activate, but at high μmolar to mmolar ion concentrations. The ions of lithium and potassium have no effect on enzyme activity between 1 μM and 10 mM.

Figure 12:
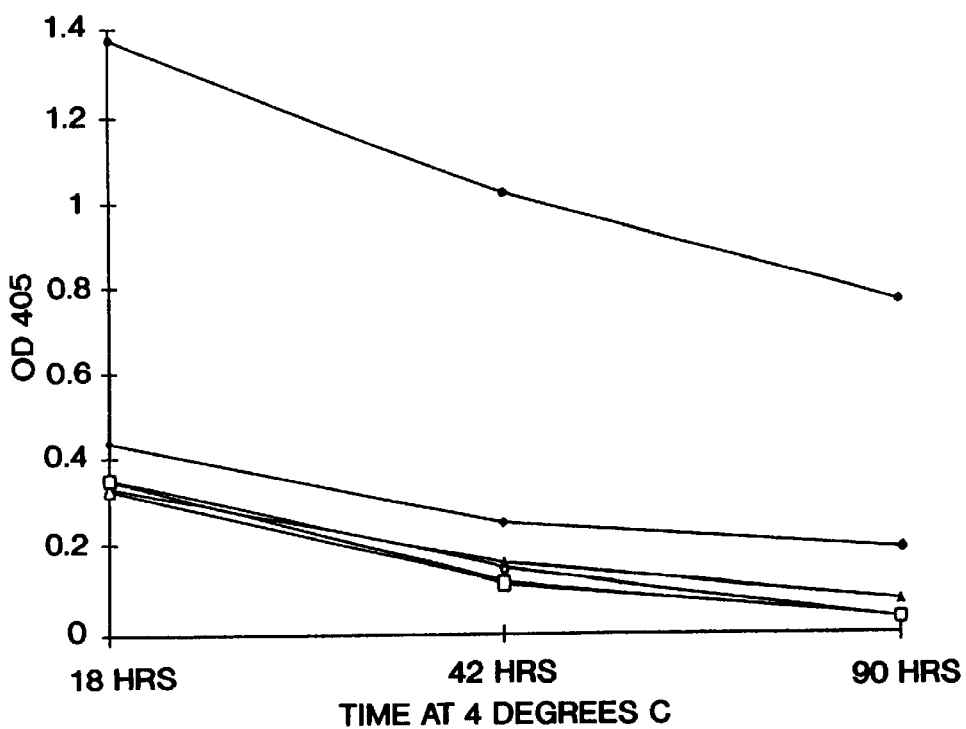
FIG. 12 is a graph of the ion enhancement of GTVap stability: control (open diamonds); 2 mM Mg (solid triangles); 0.02 mM Mn (open triangles); 2 mM Ca (solid circles); 1 μM Zn (solid squares); 1 μM Co (open squares); 0.2 mM DTT (solid diamonds)

It was evident during the initial investigations of GTVap that the Triton X-100 extracts lose enzyme activity over time at 4° C. An attempt was made to stabilize enzyme activity by adding specific ions that were previously shown to activate the enzyme. Immediately following the routine extraction of HDM the extract was diluted into 20 mM Tris-HCl, pH 7.5 containing the ions or DTT at concentrations that were previously shown to enhance enzyme activity. After various times at 4° C. aliquots were removed and GTVap activity determined. The results, shown in FIG. 12, indicate that calcium stabilizes the enzyme activity against the time dependent inactivation. Zinc, cobalt and manganese, which were previously shown to increase activity, do not stabilize the enzyme.

A number of protease inhibitors were studied to examine their inhibitory effects on GTVap. The methods of enzyme determination have been described above with the exception that various concentrations of the inhibitors were added to HDM enzyme extracts 15 minutes prior to the addition of leu-p-nitroanilide substrate. The data is presented relative to the inhibitor-free control which has 100% activity. The following inhibitors, with the maximal concentration tested being shown in parentheses, had no effect on GTVap activity using the leucine-p-nitroanilide substrate: diisopropylfluorophophate (5 mM), PMSF (1 mM), benzamidine (10 mM), leupeptin (5 mM), EDTA (5 mM).

Figure 13:
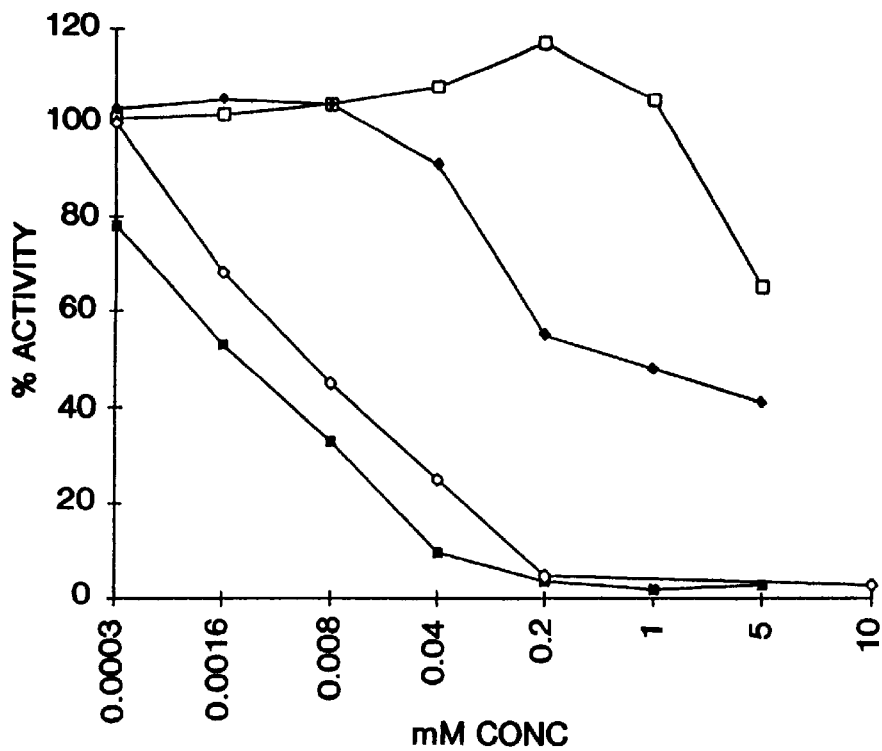
FIG. 13 is a graph of showing the effects of various protease inhibitors on GTVap activity: phenanthroline (solid squares); dithiothreitol (open squares); Leu-Leu-Phe-chloromethylketone (solid diamonds); dipyridyl (open diamonds)

Two zinc chelators, phenanthroline and dipyridyl, were found to be >98% inhibitory at >0.2 mM, as shown in FIG. 13.

Leu-Leu-Phe-chloromethyl ketone (LLPAC), a known inhibitor of calpain, has an GTVap $IC_{50}$ of 1 mM. Dithiothreitol (DTT) has a 30% inhibition at 5 mM but increases enzyme activity 20% at 0.2 mM.

Figure 14:
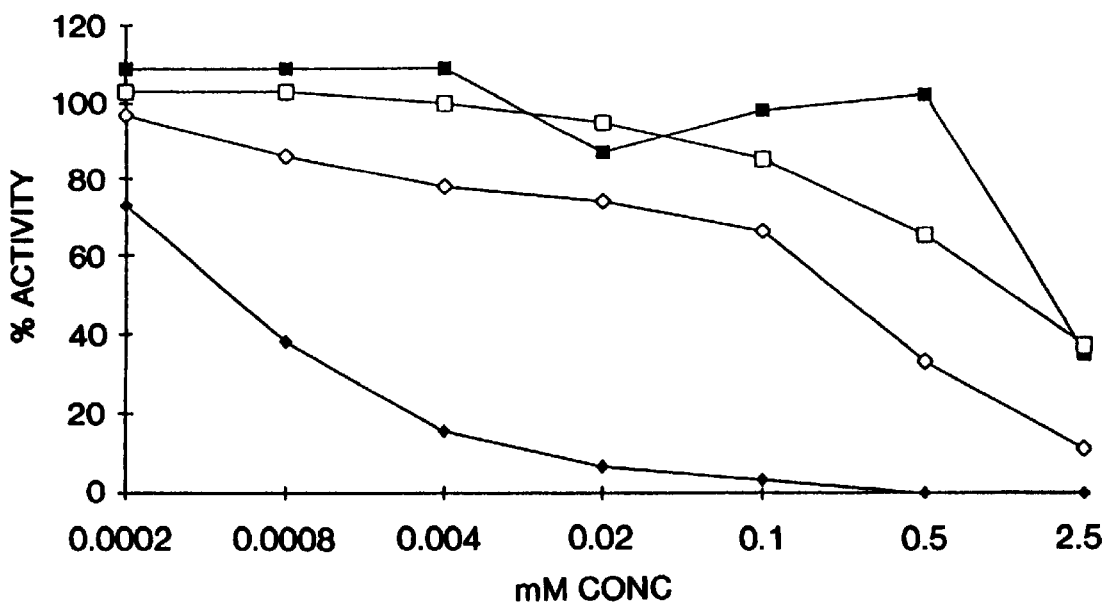
FIG. 14 is a graph of the effects of various aminopeptidase inhibitors on GTVap activity: bestatin (solid squares); actinonin (open squares); leuthiol (solid diamonds); amastatin (open diamonds)

A number of previously identified aminopeptidase inhibitors were tested on GTVap. The most effective inhibitor was leuthiol with an $IC_{50}$ of 2 $\mu$M. Amastatin had an $IC_{50}$ of 0.35 mM and bestatin and actinonin had $IC_{50}$'s of >1 mM, as shown in FIG. 14.

Purification of GTVap 165, 155 and 120 from HDM's

The strategy for the purification of the GTVap enzymes was formulated based on the relatively rapid time-dependent inactivation of the enzyme. The purification scheme employs two affinity purifications (WGA and IDAC) followed by an anion exchange chromatographic separation. Calcium ions were used to maintain optimal stability whenever possible.

Figure 15A:
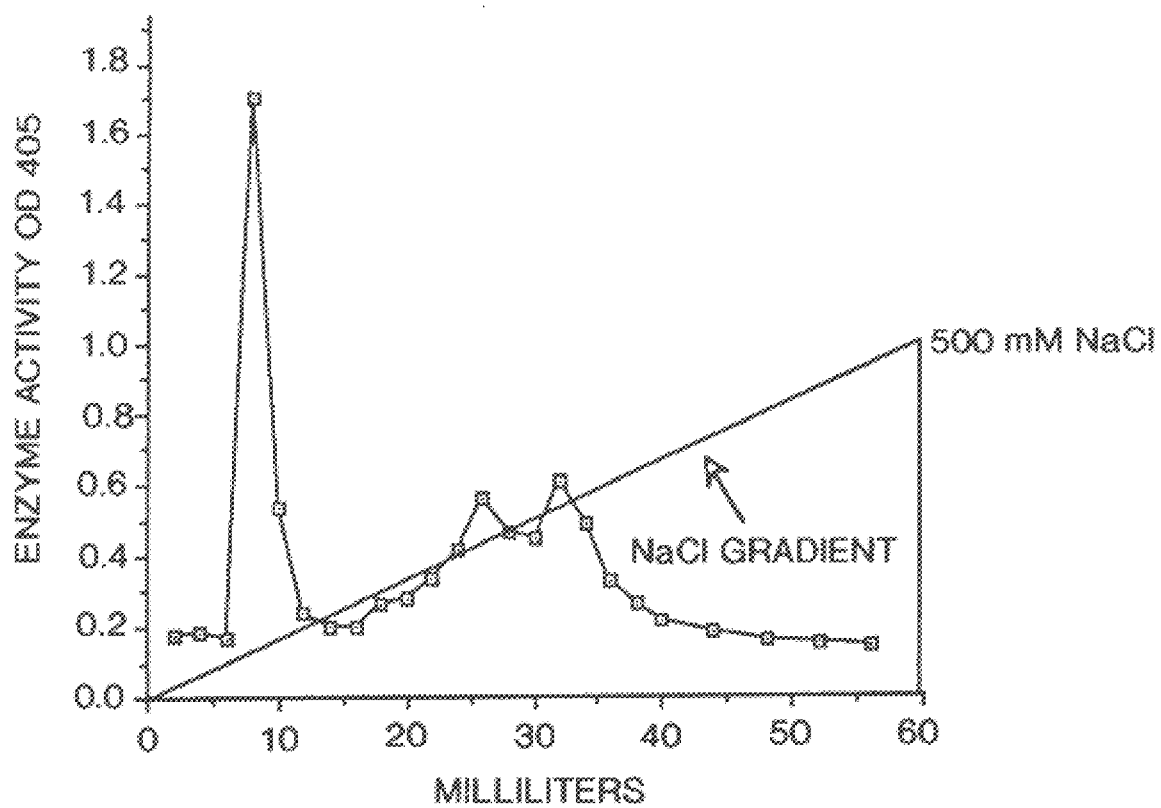
FIG. 15a is a graph of GTVap activity following an anion exchange chromatographic separation of WGA-purified GTVap.
Figure 15B:
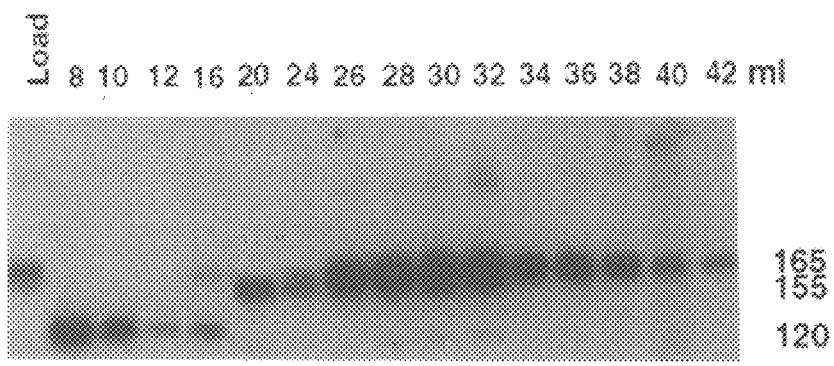
FIG. 15b is a Western blot of GTVap-120, 155 and 165 following an anion exchange chromatographic separation of WGA-purified GTVap.

Purified HDM at a concentration of 1 mg/ml was solubilized in 20 mM Tris-HCl, 0.1% Triton X-100 containing 2 mM $CaCl_2$, 150 $\mu$M PMSF, 1 mM DFP, 1 mM benzamidine, 2 $\mu$M leupeptin, and 1 $\mu$M pepstatin A. This extraction was found to solubilize 96% of the total aminopeptidase activity and 77% of the total protein of HDM fraction. The unsolubilized membrane was pelleted at 48,000×g for 20 minutes and discarded. The solubilized extract was batch incubated with wheat germ agglutinin (WGA)-Sepharose. In particular, one ml of packed wheat germ lectin-Sepharose 6 MB resin, referred to as WGA, was added per 10 mg HDM of protein and rotated overnight at 4° C. The resin was washed with the above buffer without $CaCl_2$ and eluted with 5.0 ml of 0.5M N-acetylglucosamine. Approximately 93% of the total aminopeptidase activity was bound and could be eluted from the WGA column using 0.5M N-acetylglucosamine. The WGA purified fraction could be applied directly to the anion exchange Resource Q column. Typically, the entire WGA purified fraction was applied to a 1 ml Resource Q anion exchange resin column at 4° C. A linear gradient of 0–0.5 M NaCl in 20 mM Tris, 0.1% Triton X-100, pH 7.8 at 4° C. was used for elution. All fractions were assayed for aminopeptidase activity and for Western blot reactivity to the GTVap1 antibody. As shown by FIGS. 15*a* and 15*b*, this ion exchange method separates the 120 kD immunoreactive protein from the GTVap-155 and GTVap-165 kD forms. The Resource Q Western blot profile using GTVap1 antibody identification of the 120 kD protein and GTVap-155 kD and 165 kD proteins shows excellent correlation with aminopeptidase activity. The sharp early eluting peak from the Resource Q column is the GTVap-120 with the later-eluting broad peak being first the GTVap-155, followed closely by GTVap-165.

Alternatively, the WGA purified fraction also could be applied directly to an iminodiacetic acid column preloaded with zinc. In particular, the WGA purified fraction was immediately passed down a 0.5 ml iminodiacetic acid chelation (IDAC) column previously loaded with 10 mM $ZnSO_4$ in 20 mM Tris, 0.1% Triton X-100, pH 7.5, according to the manufacturer's recommendation. After the application of WGA eluate, the column was washed with 10 column volumes of 20 mM Tris, 0.1% Triton X-100, pH 7.5. The column was then eluted with 10 mM EDTA in 20 mM Tris, 0.1% Triton X-100, pH 7.5. Approximately 93% of the aminopeptidase activity was bound to the IDAC and could be eluted with 10 mM EDTA.

Figure 16:
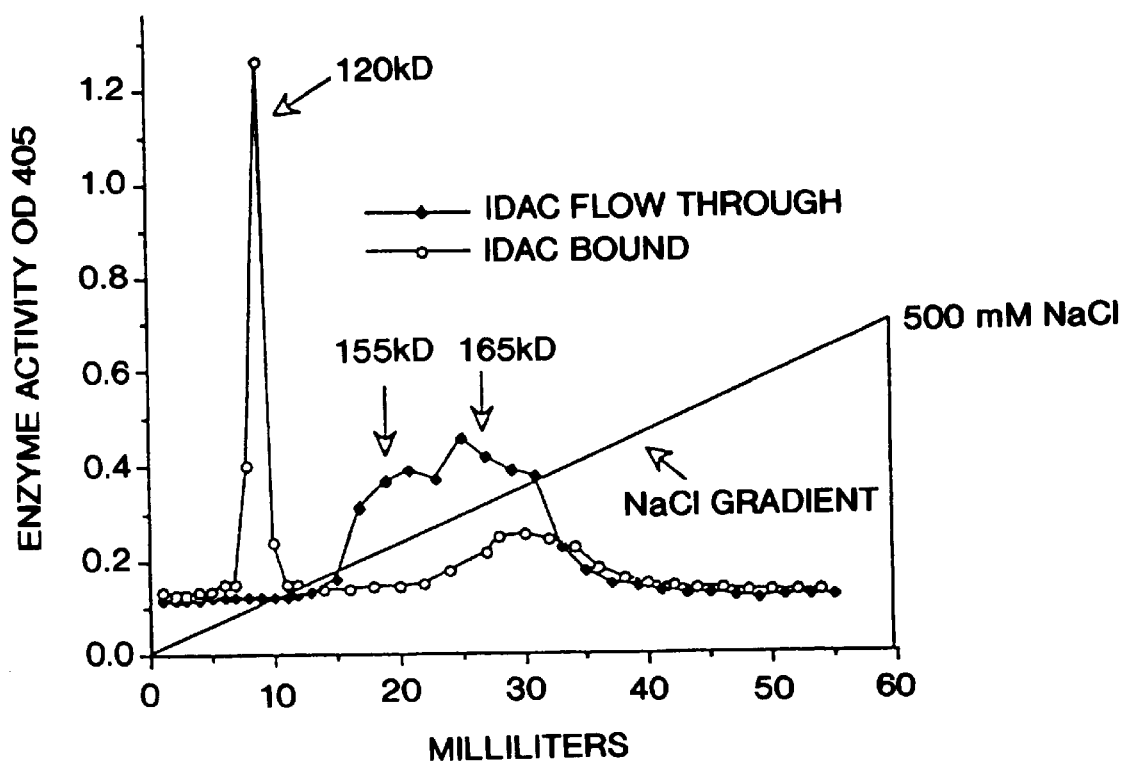
FIG. 16 is a graph of GTVap activity following an anion exchange enzyme activity profile of WGA- and IDAC-purified GTVap: iminodiacetic acid (IDAC) flow through (solid diamonds); IDAC bound (open circles)

The IDAC flow-through and the IDAC bound fractions were separately chromatographed on a 1 ml Resource Q anion exchange resin as described above. The results, shown in FIG. 16, demonstrate that the zinc-loaded IDAC column binds all of the GTVap-120, whereas most of the GTVap-155 and GTVap-165 flow through. This observation is confirmed by Western blot analysis of these fractions (data not shown). Since binding to zinc likely involves the coordination of protein histidyl residues with the bound zinc ions, it may be that the more heavily glycosylated GTVap's may be sterically hindered from binding to immobilized zinc. The fraction of the GTVap-155 and GTVap-165 that does bind to the zinc columns might be dimerized with GTVap-120 and may not interact directly with the zinc. Previous biophysical studies on other aminopeptidase suggest that these enzymes may exist as dimers.

In summary, the GTVap-120, GTVap-155, and GTVap-165 are enzymatically active, all react with the GTVap1 antibody and can be enriched and separated by the purification scheme described above.

GTVap Translocates to the Plasma Membrane in Response to Insulin

Figure 17:
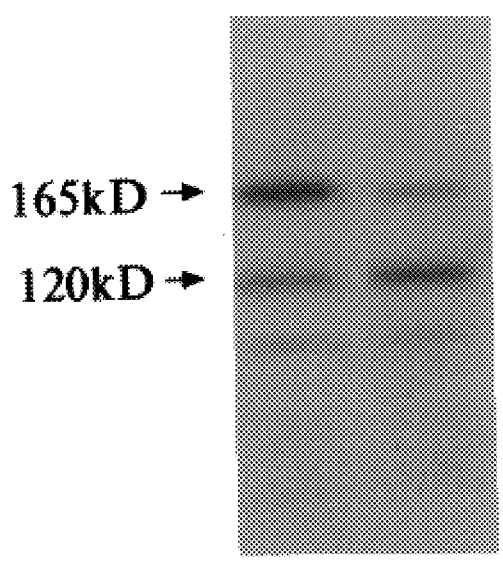
FIG. 17 is a Western blot of GTVap from the plasma membrane fraction prior to and following insulin stimulation.
Figure 18:
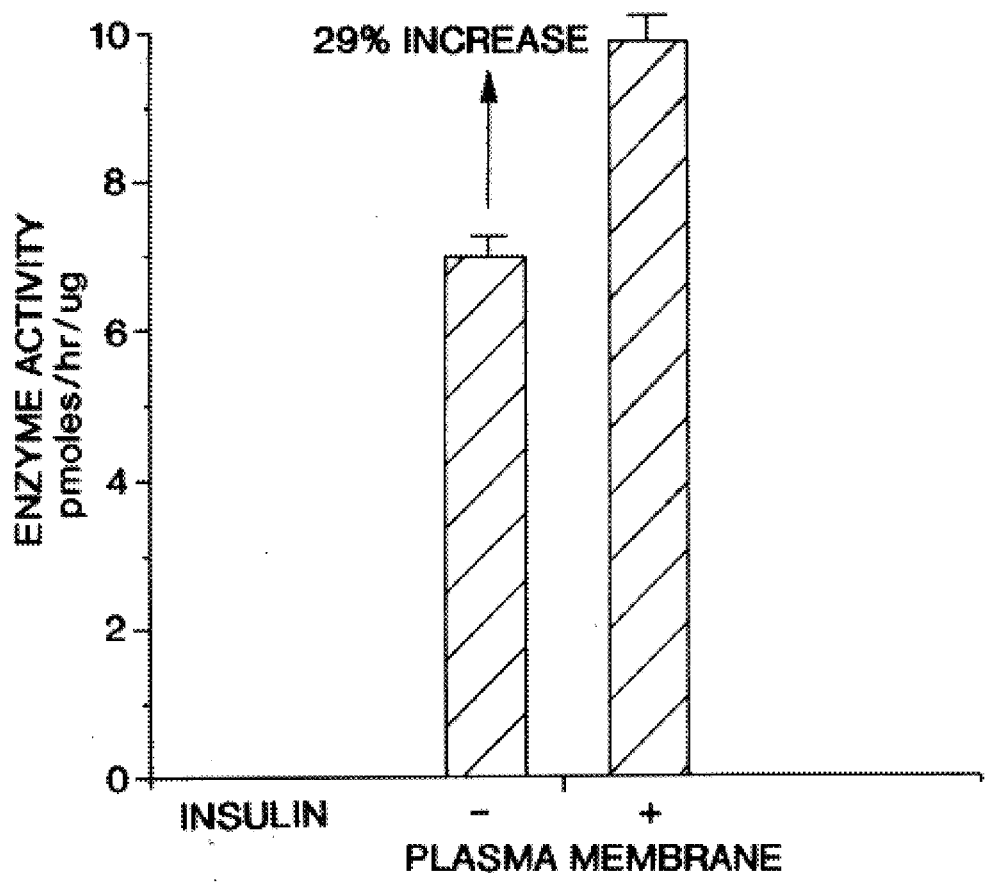
FIG. 18 is a graph of GTVap activity in the plasma membrane prior to and following insulin stimulation.

GLUT4 is known to translocate from an intracellular vesicular compartment to the plasma membrane upon insulin stimulation. In order to determine if GTVap also translocates, adipocytes dissociated from rat epididymal fat pads prepared as described above were stimulated with insulin. Insulin (10 nM) was added to freshly prepared adipocytes which were maintained for 20 minutes at 37° C. The adipocytes were then washed in TES buffer. The insulin stimulated and control adipocytes were fractionated into the subcellular compartments and analyzed for GTVap enzyme and protein (Western blot) as previously described. FIG. 17 indicates that GTVap translocates to the plasma membrane in response to insulin stimulation as evidenced by increased Western blot reactivity. FIG. 18 indicates that GTVap enzyme activity increases 29% in the plasma membrane following insulin stimulation.

GTVap Cleavage of Insulin and Synthetic Peptide Substrates

HDM (1.8 mg/ml) was incubated at 37° C. with 120 $\mu$g/ml porcine insulin in 50 mM sodium borate, pH 7.5, containing the following protease inhibitors that were previously shown to have no inhibitory effect on GTVap: 2 mM benzamidine, 2 $\mu$M leupeptin, 1 $\mu$M pepstatin, 1 mM DFP, and 150 $\mu$M PMSF. The reaction was terminated after various incubation times by centrifugation of aliquots at 200,000×g to remove the HDM. The insulin products were detected by mass spectrometry or were first chromatographed on a 2.1×15 cm Beckman Spherisorb C18 column at 0.25 ml/min. in a 4 hour linear gradient of 27% to 31% acetonitrile in 1% TFA adjusted to pH 3.0 with TEA, prior to mass spectroscopic analysis.

Figure 19A:
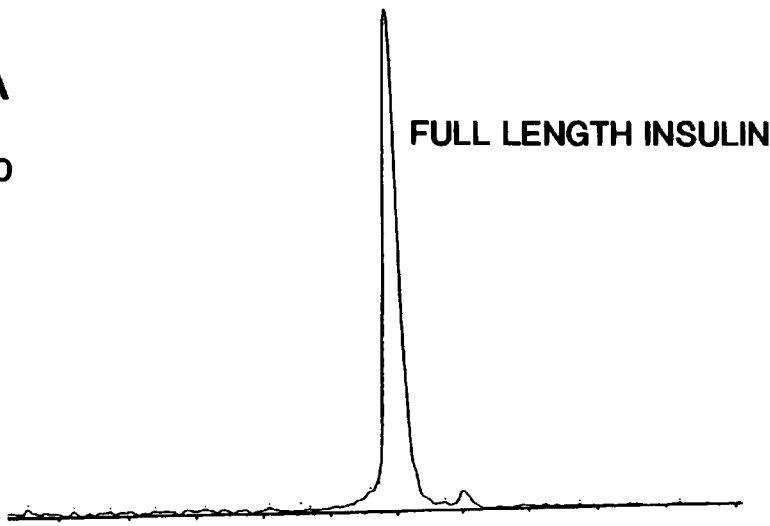
FIG. 19a–19c is a graph of the mass analysis of insulin following digestion with GTVap.
Figure 19B:
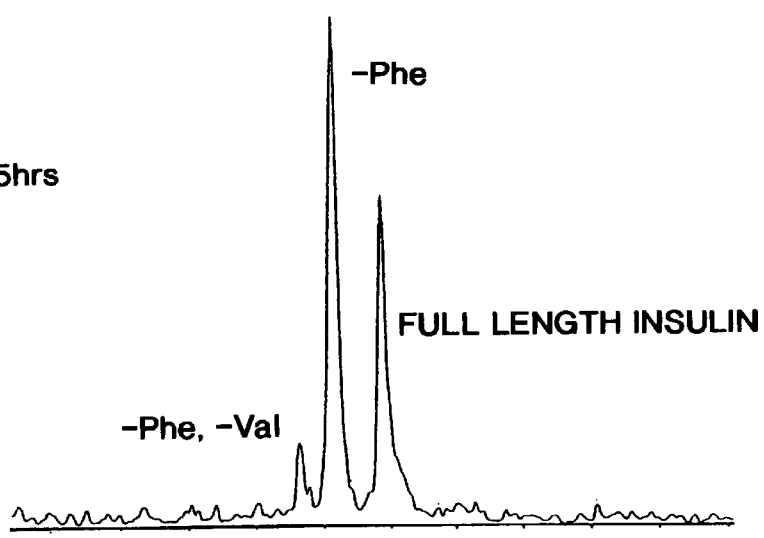
Figure 19C:
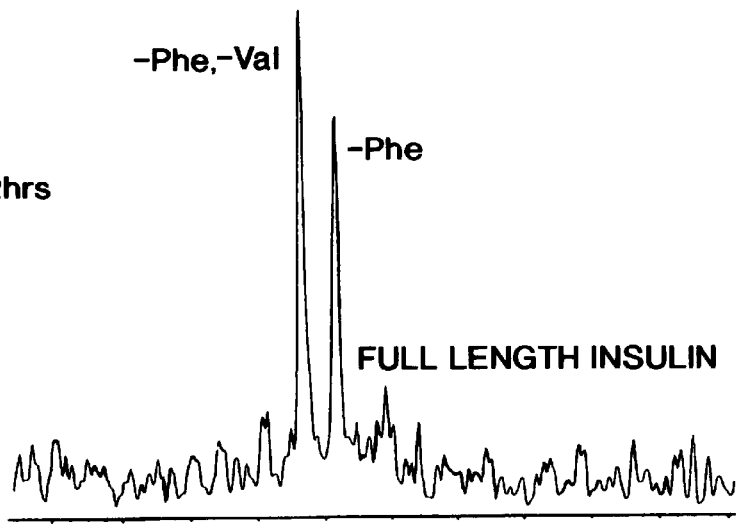

Using this method both intact and Triton X-100 extracted HDM were shown to have aminopeptidase activity towards insulin. As shown in FIG. 19a, b, and c, mass spectroscopic analysis indicated that the N-terminal residues phenylalanine and valine of the B-subunit of insulin were removed sequentially from the intact insulin molecule.

Identification of a Nucleic Acid Sequence Encoding GTVap

A set of two degenerate oligonucleotide pools were obtained, one of which encoded the first 7 amino acids of the peptide and the other of which encoded the reverse complement of the last 7 amino acids. These oligonucleotide pools were used to perform polymerase chain reaction with Ampli-Taq DNA polymerase on rat skeletal muscle cDNA generated from rat skeletal muscle polyA+ RNA using the 3' RACE kit, or by reverse transcription followed by polymerase chain reaction using retrotherm DNA polymerase on rat skeletal muscle polyA+ RNA. From these reactions short regions of unambiguous DNA sequence were obtained which encoded the peptides on which the oligonucleotides were based. Using these unambiguous nucleic acids labelled with $^{32}$P as probes, a lambda gt11 rat skeletal muscle cDNA library was screened and 25 clones encoding GTVap were identified. Three of these, identified as 5.3, 10.1, and 12.1, were sequenced with the final sequence based on the sequence of clone 12.1 as both clones 5.3 and 10.1 contained introns. Based on nucleic acid sequence near the 5' and 3' ends of clone 12.1, additional oligonuceotide probes were designed to perform 3' and 5' RACE using the Marathon RACE kit. Seven reaction products were identified at the 3' end, and two of these, identified as KC44 and KC45, were sequenced to obtain the 3' end of the cDNA described in FIG. 20 (SEQ. ID NOs. 15 and 16). Two reaction products were identified by the 5' Marathon RACE reaction and complete sequence was obtained for clone 334 and partial sequence for clone 331. An additional 5' Marathon RACE reaction was performed based on nucleic acid sequence near the 5' end of clone 334 and using the RACE product from the primary 5' Marathon RACE reaction as template. This resulted in seven additional clones of which three clones, identified as clones 2, 3 and 5, were sequenced. Taken together, these sequences make up the entire nucleic acid sequence of FIG. 20 (SEQ. ID NOs. 15 and 16). Sequencing of all clones was performed using Sequenase with the exception of clone 334 which was sequenced by LARK Sequencing Technologies, Houston, Tex. Sequence was assembled using Assemblylign (Laboratory Research Products, Eastman Kodak Company, New Haven, Conn.) and the Wisconsin Package (Genetics Computer Group, Madison, Wis.)

The initiation codon was identified using the first ATG in the nucleic acid sequence which will allow for initiation of translation [Kozak, J. Cell Biol., 108, 229–241 (1989)]. The long version of mature protein (SEQ ID NO 15) contains 1026 amino acids and has a predicted molecular weight of 117239.

The nucleic acid sequence shows a high degree of similarity with several unidentified expressed sequence tags including accession numbers R47032 and H08895. R47032, which was isolated from rat incisor non-calcified tissue, is identical to GTVap over 90 nucleotides, then diverges at both ends. This is likely to encode either an unspliced or alternately spliced form of GTVap. H08895, which was isolated from human brain, is 88.5% identical to GTVap over 382 nucleotides, the full length of this expressed sequence tag. It is likely that H08895 encodes a part of the human GTVap. The predicted protein is 32.5% identical to rat aminopeptidase N and shows >20% identity to other aminopeptidases. This level of protein identity corresponds to nucleic acid identities of 50% to 60% over more than 1000 nucleotides.

Identification of a Consensus Sequence for an Insulin-Sensitive Retention Sequence Since GTVap and GLUT4 are found in the GLUT4 vesicle and respond to insulin as evidenced by their simultaneous translocation to the plasma membrane, it was considered conceivable that both proteins share a common structural motif (retention sequence). The structural motif that confers this property to these proteins is likely to be found on other proteins that translocate in an insulin-sensitive manner. In an attempt to identify an insulin-sensitive retention sequence, the predicted protein sequence of GTVap was compared to the protein sequences of the cytoplasmic domains of GLUT4 using the Wisconsin Package computer program (Genetics Computer Group, Madison, Wis.). Significant homology was evident in two adjacent segments of the cytoplasmic domain of GTVap (SEQ ID NOs 17 and 18) and with the inverted (reading C—N) cytoplasmic domain of GLUT4 (SEQ ID NO 19). This consensus sequence is shown by the sequence identified as SEQ ID NOs 20 and 21.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A purified nucleic acid sequence which is Seq ID No. 15 or Seq ID No. 16.

2. The purified nucleic acid of claim 1, said nucleic acid being under the transcriptional control of a heterologous promoter.

3. A vector comprising a nucleic acid of claim 1.

4. A transformed cell comprising a vector of claim 1.

5. A cell of claim 4 which is a mammalian cell.

6. A method comprising culturing a transformed cell which comprises a vector comprising nucleic acid Seq ID No. 15 or Seq ID No. 16 in an appropriate medium, permitting the protein encoded by the nucleic acid to be expressed in the culture, and recovering the protein from the culture.

* * * * *